US012582675B2

(12) United States Patent
Monje-Deisseroth et al.

(10) Patent No.: US 12,582,675 B2
(45) **Date of Patent: *Mar. 24, 2026**

(54) METHODS FOR TREATMENT OF CANCERS HARBORING AN H3K27M MUTATION

(71) Applicant: The Board of Trustees of the Leland Stanford Junior University, Stanford, CA (US)

(72) Inventors: Michelle Monje-Deisseroth, Stanford, CA (US); Robbie Majzner, Stanford, CA (US); Crystal Mackall, Stanford, CA (US); Christopher Mount, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 839 days.

This patent is subject to a terminal disclaimer.

(21) Appl. No.: 17/815,056

(22) Filed: Jul. 26, 2022

(65) Prior Publication Data

US 2023/0054466 A1 Feb. 23, 2023

Related U.S. Application Data

(63) Continuation of application No. 16/629,604, filed as application No. PCT/US2018/041839 on Jul. 12, 2018, now Pat. No. 11,433,098.

(60) Provisional application No. 62/651,406, filed on Apr. 2, 2018, provisional application No. 62/531,872, filed on Jul. 12, 2017.

(51) Int. Cl.

| | |
|---|---|
| *A61K 35/17* | (2025.01) |
| *A61K 39/00* | (2006.01) |
| *A61K 40/11* | (2025.01) |
| *A61K 40/31* | (2025.01) |
| *A61K 40/42* | (2025.01) |
| *A61K 45/06* | (2006.01) |
| *A61P 35/00* | (2006.01) |
| *C07K 16/30* | (2006.01) |

(52) U.S. Cl.
CPC .............. *A61K 35/17* (2013.01); *A61K 39/00* (2013.01); *A61K 40/11* (2025.01); *A61K 40/31* (2025.01); *A61K 40/4258* (2025.01); *A61K 45/06* (2013.01); *A61P 35/00* (2018.01); *C07K 16/3084* (2013.01); *A61K 2239/31* (2023.05); *A61K 2239/38* (2023.05)

(58) Field of Classification Search
CPC ........ A61K 35/17; A61K 39/00; A61K 40/11; A61K 40/31; A61K 40/4258; A61K 2039/80; A61P 35/00; C07K 16/3084; C07K 14/7051; C07K 2319/03
See application file for complete search history.

(56) References Cited

U.S. PATENT DOCUMENTS

| | | | |
|---|---|---|---|
| 4,016,043 A | 4/1977 | Schuurs et al. | |
| 4,018,653 A | 4/1977 | Mennen | |
| 4,424,279 A | 1/1984 | Bohn et al. | |
| 6,033,669 A | 3/2000 | Jondal | |
| 2014/0107039 A1 | 4/2014 | Allis et al. | |
| 2017/0027988 A1 | 2/2017 | Brenner et al. | |

FOREIGN PATENT DOCUMENTS

| | | |
|---|---|---|
| WO | WO 2012/033885 | 3/2012 |
| WO | WO 2013/040371 | 3/2012 |
| WO | WO 2013/126733 | 8/2013 |
| WO | WO 2015/164594 | 10/2015 |

OTHER PUBLICATIONS

Ali et al., Xenogeneic graft-versus-host-disease in NOD-scid IL-2Rγnull mice display a T-effector memory phenotype. PLoS One. 2012;7(8):e44219. 10 pages.
Brinkman et al., Easy quantitative assessment of genome editing by sequence trace decomposition. Nucleic Acids Res. Dec. 16, 2014;42(22):e168. 8 pages.
Cooper. T-cell therapy for diffuse pontine glioma. The Dana Foundation. Apr. 5, 2014. 4 pages. url:http://web.archive.org/web/20140405135629/http://dana.org/media/grantsdetails.aspx?id=38777.
Eisenhauer et al., New response evaluation criteria in solid tumours: revised RECIST guideline (version 1.1). Eur J Cancer. Jan. 2009;45(2):228-47.
Extended European Search Report for PCT/US2018/041839. Mailed Apr. 28, 2021. 10 pages.
Grasso et al., Functionally defined therapeutic targets in diffuse intrinsic pontine glioma. Nat Med. Jun. 2015;21(6):555-9.
Haso et al., Anti-CD22-chimeric antigen receptors targeting B-cell precursor acute lymphoblastic leukemia. Blood. Feb. 14, 2013;121(7):1165-74.
Heczey et al., CAR T Cells Administered in Combination with Lymphodepletion and PD-1 Inhibition to Patients with Neuroblastoma. Molecular Therapy, 2017: vol. 25 No 9. 2214-2224. 19 pages.
Hendel et al., Chemically modified guide RNAs enhance CRISPR-Cas genome editing in human primary cells. Nat Biotechnol. Sep. 2015;33(9):985-989.
Hou et al. Novel and shared neoantigen for glioma T chell therapy derived from histone 3 variant h3.3 k27m mutation. Journal for Immuno Therapy of Cancer 2015, 3(Suppl 2): P445. pp. 1-2.
International Search Report and Written Opinion for PCT/US18/41839. Mailed Sep. 27, 2018. 11 pages.
Jena et al., Chimeric antigen receptor (CAR)-specific monoclonal antibody to detect CD19-specific T cells in clinical trials. PLoS One. 2013;8(3):e57838. 12 pages.

(Continued)

*Primary Examiner* — Elly-Gerald Stoica
(74) *Attorney, Agent, or Firm* — Casimir Jones, S.C.; Kelly A. Barton

(57) ABSTRACT

The invention relates to immunotherapeutic treatment of cancer. In particular, the invention relates to methods of treating cancer carrying a histone H3 K27M (H3K27M) mutation (e.g., diffuse midline glioma with H3K27M mutation) using immunotherapeutic compositions comprising immune cells engineered to express GD2-specific chimeric antigen receptors.

19 Claims, 33 Drawing Sheets

Specification includes a Sequence Listing.

(56) References Cited

OTHER PUBLICATIONS

Khuong-Quang et al., K27M mutation in histone H3.3 defines clinically and biologically distinct subgroups of pediatric diffuse intrinsic pontine gliomas. Acta Neuropathol. Sep. 2012;124(3):439-47.

Lin et al., A Protocol for Rapid Post-mortem Cell Culture of Diffuse Intrinsic Pontine Glioma (DIPG). J Vis Exp. Mar. 7, 2017;(121):55360. 8 pages.

Long et al., 4-1BB costimulation ameliorates T cell exhaustion induced by tonic signaling of chimeric antigen receptors. Nat Med. Jun. 2015;21(6):581-90.

Long et al., Reduction of MDSCs with All-trans Retinoic Acid Improves CAR Therapy Efficacy for Sarcomas. Cancer Immunol Res. Oct. 2016;4(10):869-880.

Louis et al., The 2016 World Health Organization Classification of Tumors of the Central Nervous System: a summary. Acta Neuropathol. Jun. 2016;131(6):803-20.

Louveau et al., Structural and functional features of central nervous system lymphatic vessels. Nature. Jul. 16, 2015;523(7560):337-41.

Lynn et al., Targeting of folate receptor β on acute myeloid leukemia blasts with chimeric antigen receptor-expressing T cells. Blood. May 28, 2015;125(22):3466-76.

Majzner et al., Harnessing the Immunotherapy Revolution for the Treatment of Childhood Cancers. Cancer Cell. Apr. 10, 2017;31(4):476-485.

Monje et al., Hedgehog-responsive candidate cell of origin for diffuse intrinsic pontine glioma. Proc Natl Acad Sci U S A. Mar. 15, 2011;108(11):4453-8.

Mount et al., GD2-Directed chimeric antigen receptor T cells as a potent immunotherapy regimen in xenograft models of diffuse intrinsic pontine glioma. Neuro Oncol, Nov. 2017; 19(Suppl 6) vi198. 1 page.

Mount et al., Potent antitumor efficacy of anti-GD2 CAR T cells in H3-K27M + diffuse midline gliomas. Nat Med. May 2018;24(5):572-579.

Nagaraja et al., Transcriptional Dependencies in Diffuse Intrinsic Pontine Glioma. Cancer Cell. May 8, 2017;31(5):635-652.e6.

Perez Horta et al., Anti-GD2 mAbs and next-generation mAb-based agents for cancer therapy. Immunotherapy. Sep. 2016;8(9):1097-117.

Qin et al., Neural Precursor-Derived Pleiotrophin Mediates Subventricular Zone Invasion by Glioma. Cell. Aug. 24, 2017;170(5): 845-859.e19.

Richman et al., High-Affinity GD2-Specific CAR T Cells Induce Fatal Encephalitis in a Preclinical Neuroblastoma Model. Cancer Immunol Res. Jan. 2018;6(1):36-46.

Schwartzentruber et al., Driver mutations in histone H3.3 and chromatin remodelling genes in paediatric glioblastoma. Nature. Jan. 29, 2012;482(7384):226-31.

Sen et al., Induction of IgG antibodies by an anti-idiotype antibody mimicking disialoganglioside GD2. J Immunother. Jan. 1998;21(1):75-83.

Therasse et al., New guidelines to evaluate the response to treatment in solid tumors. European Organization for Research and Treatment of Cancer, National Cancer Institute of the United States, National Cancer Institute of Canada. J Natl Cancer Inst. Feb. 2, 2000;92(3):205-16.

Thomas et al., An Optimized GD2-Targeting Retroviral Cassette for More Potent and Safer Cellular Therapy of Neuroblastoma and Other Cancers. PLoS One. Mar. 31, 2016;11(3):e0152196. 19 pages.

Topalian et al., Safety, activity, and immune correlates of anti-PD-1 antibody in cancer. N Engl J Med. Jun. 28, 2012;366(26):2443-54.

Wolchok et al., Guidelines for the evaluation of immune therapy activity in solid tumors: immune-related response criteria. Clin Cancer Res. Dec. 1, 2009;15(23):7412-20.

Wu et al., Somatic histone H3 alterations in pediatric diffuse intrinsic pontine gliomas and non-brainstem glioblastomas. Nat Genet. Jan. 29, 2012;44(3):251-3.

Yu et al., Anti-GD2 antibody with GM-CSF, interleukin-2, and isotretinoin for neuroblastoma. N Engl J Med. Sep. 30, 2010;363(14): 1324-34.

Chheda et al., (2017). OS09.4 Identification of a novel H3.3. K27M mutation-derived neoantigen epitope and cloning of H3.3 K27M-specific T-cell receptor for T-cell therapy in gliomas. Neuro-Oncology. 19. iii18-iii19. 10.1093/neuonc/nox036.063.

Chheda et al., Novel and shared neoantigen derived from histone 3 variant H3.3K27M mutation for glioma T chell therapy. J Exp Med. Jan. 2, 2018;215(1):141-157.

Furukawa, K & Fukuda, M. (2016) Glycosignals in Cancer: Mechanisms of Malignant Phenotypes. 10.1007/978-4-431-55939-9.

Horta et al., Anti-GD2 mAbs and next-generation and mAb-based agents for cancer therapy. Immunotherapy. Sep. 2016;8(9): 1097-117.

Longee et al., Disialoganglioside GD2 in human neuroectodermal tumor cell lines and gliomas. Acta Neuropathol. 1991;82(1):45-54.

Scutti Jab. Importance of immune monitoring approaches and the use of immune checkpoints for the treatment of diffuse intrinsic pontine glioma: From bench to clinc and vice versa (Review). Int J Oncol. Apr. 2018;52(4):1041-1056.

Seyedin et al. Stratagies for combining immunotherapy with radiation for anticancer therapy. Immunotherapy. 2015;7(9):967-980.

Suzuki and Cheung. Disialoganglioside GD2 as therapeutic target for human diseases. Expert Opin Ther Targets. Mar. 2015;19(3):349-62.

Tai et al. Different fine binding specificites of monoclonal antibodies to disialosylganglioside GD2. J Biochem. Apr. 1988;103(4):682-7.

Office Action for JP App. No. 2020-501539, mailed Aug. 23, 2022, 3 pages.

Cooper, L.J.N. T-Cell Therapy for Diffuse Interstitial Pontine Glioma. https://web.archive.org/web/20140405135629/http://dana.org/Media/GrantsDetails.aspx?id=38777.

Pascual-Pasto, G. et al. Preclinical platform of retinoblastoma xenografts recapitulating human disease and molecular markers of dissemination. Cancer Letters 380 (2016) 10-19.

FIG. 5A
Neuroblastoma
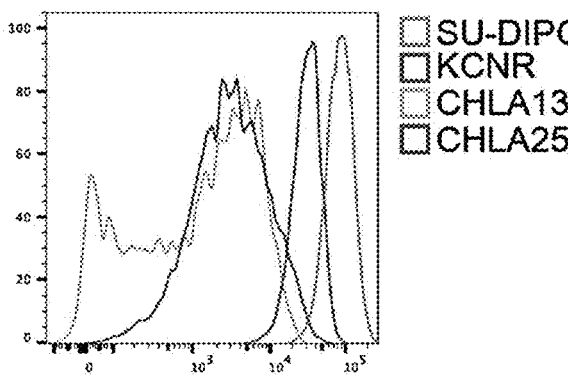
☐ SU-DIPG6
☐ KCNR
☐ CHLA136
☐ CHLA255
FIG. 5A, cont'd
Osteosarcoma
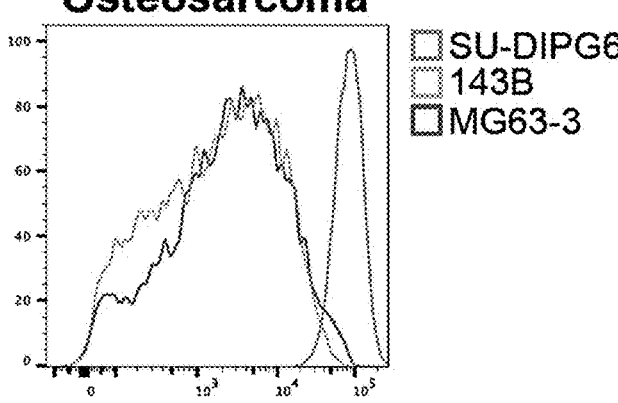
☐ SU-DIPG6
☐ 143B
☐ MG63-3
FIG. 5A, cont'd
Ewing Sarcoma
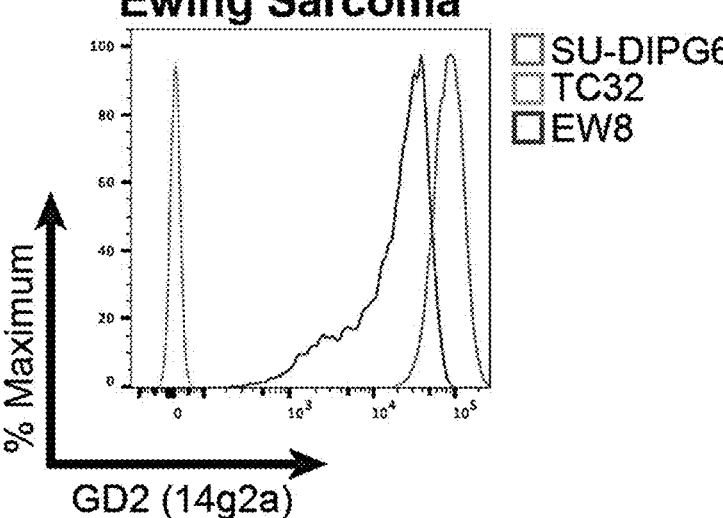
☐ SU-DIPG6
☐ TC32
☐ EW8
% Maximum
GD2 (14g2a)

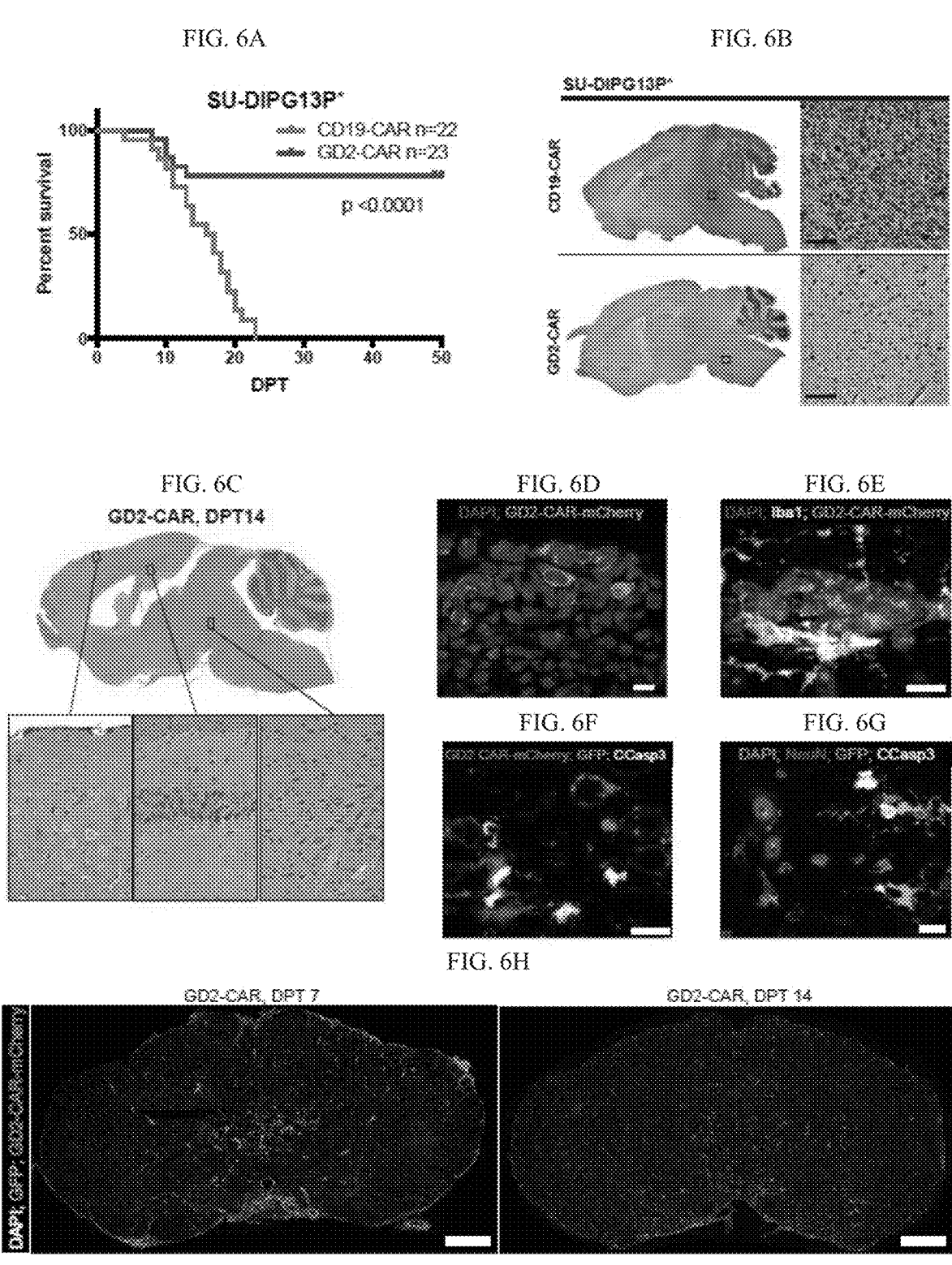

— CD19-CAR
—•— GD2-CAR

SU-DIPG-13P* Cohort 1    SU-DIPG-13P* Cohort 2    SU-DIPG-13P* Cohort 3

FIG. 8A
FIG. 8C
**CD19 CAR,
DPT 20
(endpoint)**
**GD2 CAR,
DPT 20**
**GD2 CAR
DPT 50
(endpoint)**
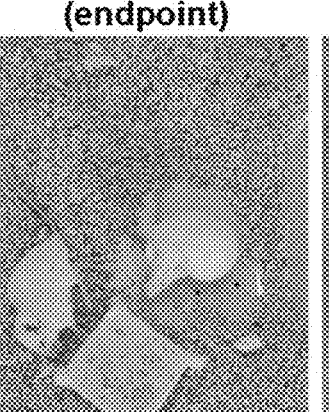
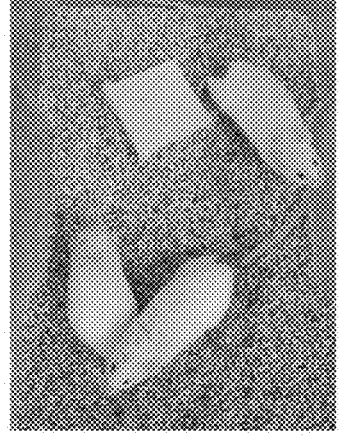
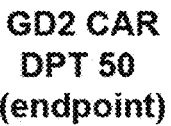
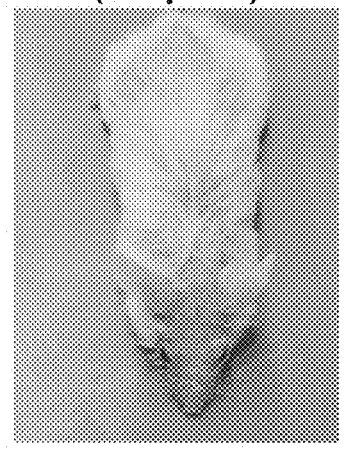
FIG. 8B
CD19 CAR, skin DPT 14
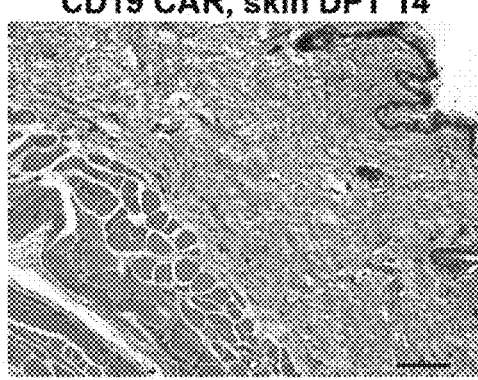
FIG. 8D
GD2 CAR, skin DPT 50
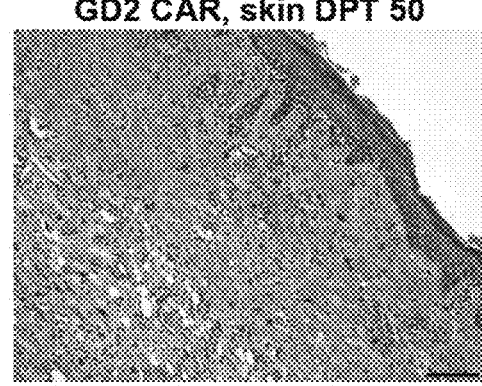

FIG. 10A
DIPG13FL, CD19-CAR, DPT7                    DIPG13FL, GD2-CAR, DPT7
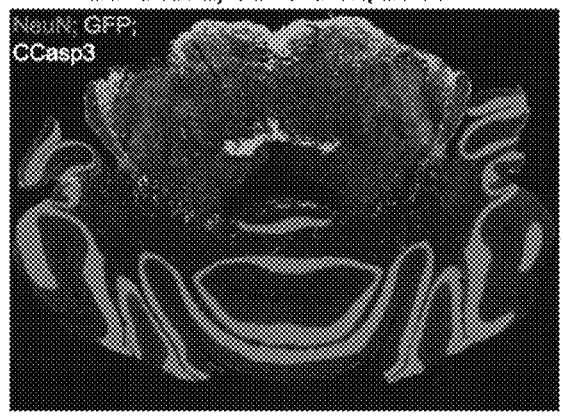 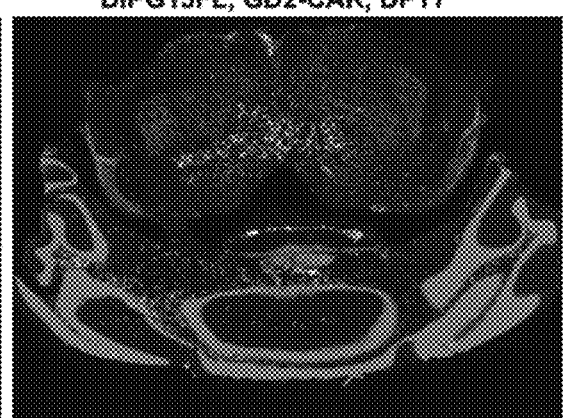
FIG. 10B
DIPG13FL, GD2-CAR, DPT7
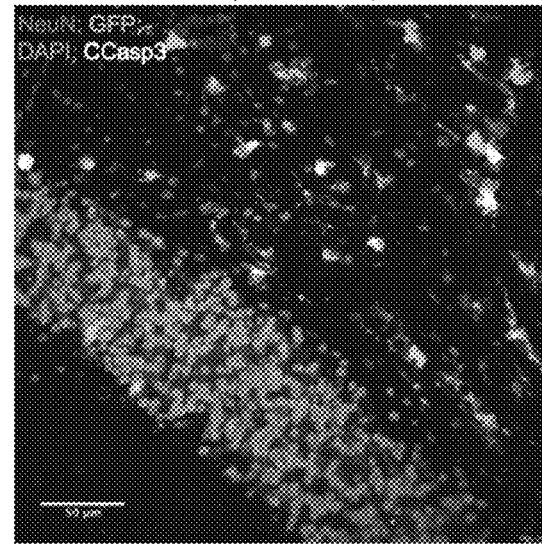
FIG. 10C
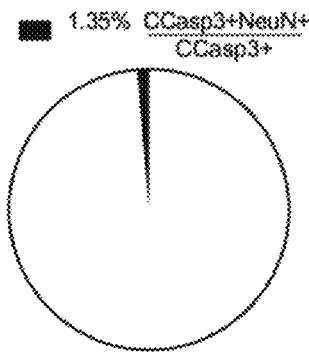
Total≈740 CCasp3+ cells
n=4 animals FIG. 11E                 FIG. 11F
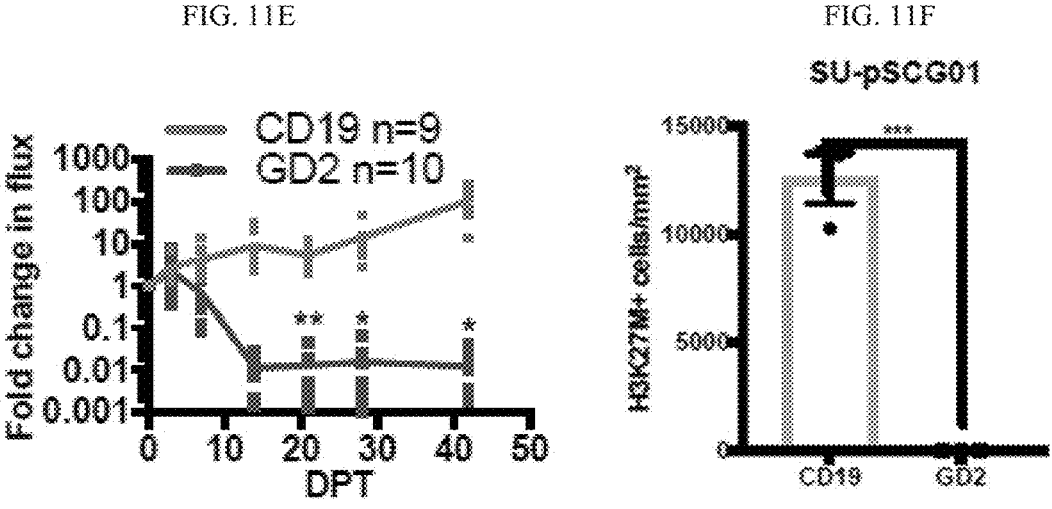
FIG. 11G
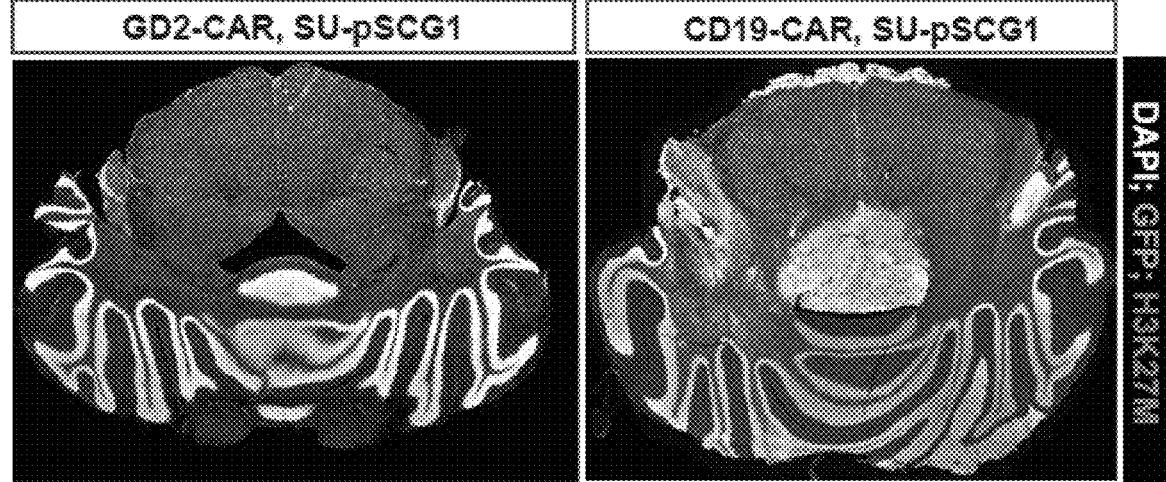

FIG. 11I
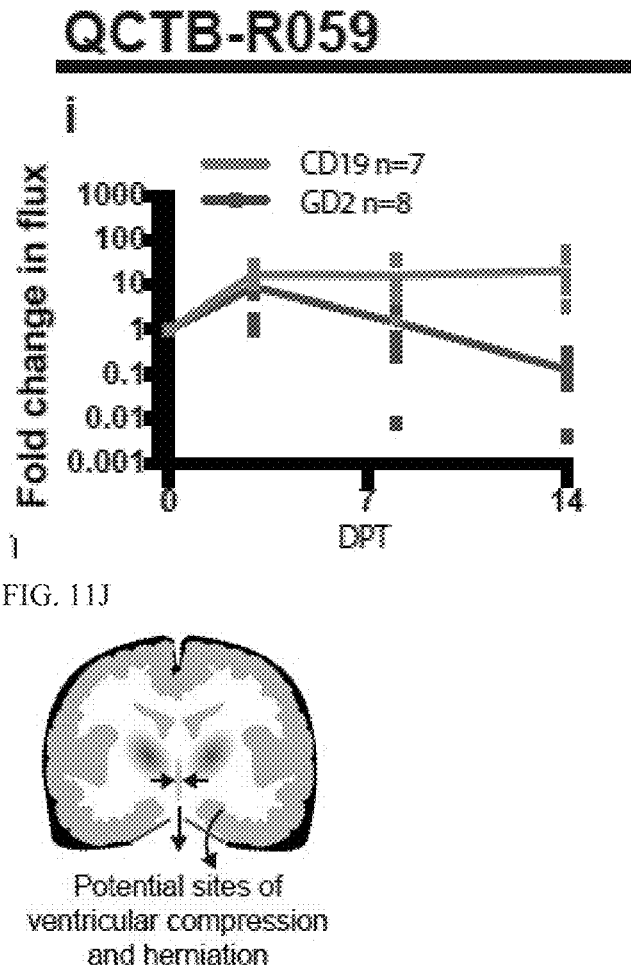
FIG. 11J
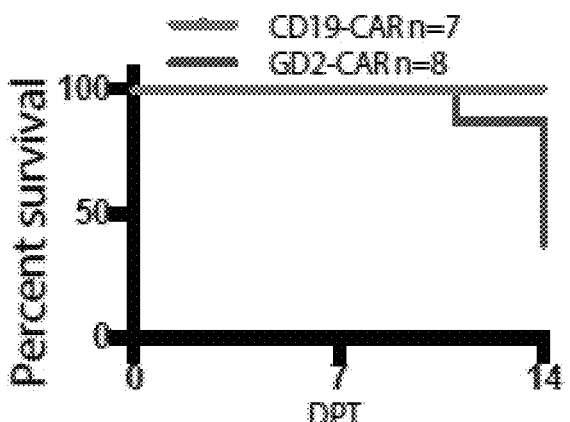
FIG. 11K

FIG. 13

| ID | SU-DIPG13 | SU-DIPG17 | SU-DIPG19 | SU-DIPG27 |
|---|---|---|---|---|
| CD1a | 1.112211221 | 1.147751606 | 0.875305623 | 0.938337802 |
| CD1b | 0.98348835 | 1.248394008 | 0.772618137 | 0.946380697 |
| CD1d | 1.171617162 | 1.220356745 | 1.035894868 | 1.289544236 |
| CD2 | 0.749174917 | 1.017130621 | 0.718381418 | 0.852546017 |
| CD3 | 0.702843377 | 0.971830986 | 1.159010601 | 0.414906832 |
| CD4 | 0.930693069 | 1.12633893 | 0.899785501 | 1.013484826 |
| CD4+4 | 0.96039664 | 1.096159743 | 1.398583007 | 1.066793094 |
| CD5 | 0.871834625 | 1.124748491 | 1.102473498 | 0.41242336 |
| CD6 | 0.856435644 | 1.124197002 | 0.831295844 | 0.854423592 |
| CD7 | 0.968646865 | 1.987152034 | 0.821515893 | 0.895443359 |
| CD8a | 1.318481848 | 1.460385439 | 1.163814181 | 1.284182306 |
| CD8b | 0.724886282 | 0.983903421 | 1.108007067 | 0.423802484 |
| CD9 | 275.6105611 | 63.21199143 | 65.50122249 | 323.0911528 |
| CD10 | 1.369309044 | 1.146681288 | 1.777385159 | 0.85609441 |
| CD11a | 2.338301392 | 3.521126761 | 2.519434629 | 1.267080745 |
| CD11b | 0.968992248 | 0.983783696 | 0.898466431 | 0.407453416 |
| CD11c | 0.98679868 | 1.182012848 | 0.953545232 | 0.946380697 |
| CD13 | 1.930693069 | 6.488222698 | 0.968215159 | 1.703413869 |
| CD14 | 1.393348837 | 2.615694165 | 1.358890459 | 0.940372671 |
| CD15 | 24.6469687 | 10 | 12.13114754 | 17.6427256 |
| CD15s | 0.936026936 | 0.84317032 | 0.355191257 | 0.613259669 |
| CD16 | 0.872937394 | 1.062098501 | 1.656234719 | 0.983914209 |
| CD18 | 1.895709571 | 1.428365325 | 0.918870416 | 1.305838027 |
| CD19 | 0.811081188 | 1.237687366 | 0.736181369 | 1.821447721 |
| CD20 | 1.34595535 | 1.394741379 | 0.97 | 0.767276688 |
| CD21 | 1.199669967 | 1.027837259 | 0.71398643 | 0.927613041 |
| CD22 | 1.094009901 | 1.059457173 | 0.787286064 | 0.967828418 |
| CD23 | 1.811351155 | 1.189207709 | 0.743276284 | 0.96080429 |
| CD24 | 150.7364841 | 11.58953722 | 54.06360428 | 11.38509317 |
| CD25 | 1.069306931 | 1.233404711 | 0.621026895 | 0.854423592 |
| CD26 | 1.293079208 | 10.57815846 | 1.858190709 | 1.117962466 |
| CD27 | 0.97389736 | 1.13490364 | 0.894865526 | 0.90016622 |
| CD28 | 0.922442244 | 1.189207709 | 0.926660367 | 0.855227882 |
| CD29 | 28.39534884 | 19.47686117 | 47.68784452 | 18.16149868 |
| CD30 | 2.01339132 | 16.38115632 | 1.222493888 | 0.852546017 |
| CD31 | 1.247324752 | 3.004382655 | 1.64782176 | 1.72386859 |
| CD32 | 2.203098107 | 1.078741379 | 1.73 | 0.773599129 |
| CD33 | 1.037953795 | 1.222698073 | 0.645476773 | 0.841823056 |

FIG. 13 CONT.

| | | | | |
|---|---|---|---|---|
| CD34 | 8.316831683 | 2.087784433 | 29.83325183 | 20.13404826 |
| CD35 | 0.839933993 | 1.137044968 | 0.758611347 | 0.823737265 |
| CD36 | 1.099326899 | 0.824638573 | 0.577868852 | 0.797421731 |
| CD37 | 1.085888581 | 1.12833833 | 0.958435208 | 0.908847185 |
| CD38 | 1.732673267 | 1.539614561 | 0.843785281 | 1.436997319 |
| CD39 | 1.340791738 | 1.323375882 | 9.733333333 | 3.834422858 |
| CD40 | 5.297029703 | 11.00642398 | 1.009779051 | 1.699731903 |
| CD41a | 1.064956495 | 1.092077088 | 1.080684397 | 1.18788756 |
| CD41b | 1.157119478 | 1.364312288 | 0.975609758 | 0.551324503 |
| CD42a | 1.081650185 | 1.182783726 | 0.838858856 | 1.397587131 |
| CD42b | 1.122312213 | 1.182783726 | 0.792176839 | 0.81786437 |
| CD43 | 0.998164835 | 2.355468385 | 0.929095353 | 1.107238686 |
| CD44 | 136.6385198 | 132.9525862 | 12.16666667 | 186.2963963 |
| CD45 | 1.128712871 | 1.062098581 | 0.738386389 | 1.619303949 |
| CD45RA | 2.874354561 | 1.243534483 | 2.42 | 2.788671034 |
| CD45RB | 0.747524733 | 1.047109288 | 0.745721271 | 0.973190349 |
| CD45RO | 0.740310878 | 1.088319115 | 1.328621608 | 0.534161491 |
| CD46 | 43.15245478 | 79.81770624 | 72.01413428 | 40.57142857 |
| CD47 | 227.9397923 | 52.88513939 | 72.44498778 | 283.6758223 |
| CD48 | 0.885521088 | 0.880269815 | 0.674863388 | 0.926335175 |
| CD49a | 1.622113211 | 20.8351177 | 16.58678707 | 19.14209115 |
| CD49b | 0.947194719 | 13.35446385 | 3.819078085 | 4.399113282 |
| CD49c | 27.97029703 | 89.82869379 | 22.20393399 | 103.1286434 |
| CD49d | 13.15181518 | 28.97216274 | 21.5403423 | 25.14745308 |
| CD49e | 13.51485149 | 32.85567452 | 11.36919315 | 4.71849866 |
| CD50 | 1.755593804 | 1.107758621 | 1.023333333 | 0.958685664 |
| CD51/61 | 38.65816503 | 12.88513939 | 13.80713496 | 34.36997319 |
| CD53 | 1.036105611 | 1.037815846 | 0.826403868 | 1.214477212 |
| CD54 | 131.5498534 | 58.29741379 | 9.611333333 | 74.96196078 |
| CD55 | 9.651162791 | 88.35130785 | 28.68078671 | 15.79186335 |
| CD56 | 138.4818482 | 53.0620985 | 73.44743276 | 481.1360054 |
| CD57 | 285.1515151 | 14.63743676 | 29.08469945 | 343.2412523 |
| CD58 | 77.27399181 | 34.88402814 | 111.4134276 | 66.70867453 |
| CD59 | 374.9234806 | 143.8631791 | 135.4416981 | 413.9583186 |
| CD61 | 42.88778878 | 9.830107066 | 13.71638143 | 33.40482374 |
| CD61E | 0.831683168 | 1.283426124 | 0.738386389 | 1.340482374 |
| CD62L | 1.120463046 | 2.483940043 | 0.731051345 | 1.412868683 |
| CD62P | 0.793079208 | 1.107066381 | 0.635696823 | 1.163538874 |
| CD63 | 67.59073908 | 45.89399786 | 33.14669927 | 171.2608536 |
| CD64 | 0.859735974 | 1.21627489 | 0.640586797 | 1.107238686 |
| CD66 (acde) | 3.15245478 | 32.8772635 | 3.981068071 | 8.711861242 |

FIG. 13 CONT.

| | | | | |
|---|---|---|---|---|
| CD66b | 0.851851852 | 2.259666459 | 0.359286617 | 0.731123389 |
| CD66f | 0.818481848 | 1.182012848 | 0.819870008 | 1.209115282 |
| CD69 | 0.998349835 | 1.283883298 | 1.92208489 | 1.88310992 |
| CD70 | 8.363338789 | 28.81784387 | 7.2899729 | 1.145695364 |
| CD71 | 22.15762274 | 28.38239376 | 35.05300153 | 34.78887453 |
| CD72 | 1.438808451 | 9.504318345 | 8.91 | 0.94335512 |
| CD73 | 82.92079208 | 62.37687166 | 13.69193194 | 48.8310992 |
| CD74 | 1.511627907 | 1.647887324 | 1.94040965 | 0.458385093 |
| CD75 | 1.868688869 | 8.873524452 | 0.454918033 | 0.800368324 |
| CD77 | 1.277777778 | 1.534669983 | 0.549188328 | 0.727440147 |
| CD79b | 1.342574237 | 1.122085675 | 0.889735501 | 1.332439678 |
| CD80 | 1.51986019 | 2.462536767 | 0.821515893 | 3.688965197 |
| CD81 | 398.5313531 | 309.5074046 | 138.0684597 | 334.7809276 |
| CD83 | 1.48349835 | 4.88993576 | 1.893909533 | 2.396782847 |
| CD84 | 1.193069307 | 1.20778779 | 1.2200489 | 1.382949062 |
| CD85 | 1.018327822 | 1.161837931 | 1.333333333 | 0.993464052 |
| CD86 | 1.914391419 | 0.925853533 | 0.848418758 | 0.997319035 |
| CD87 | 0.884488449 | 1.361884368 | 0.682151599 | 0.922252911 |
| CD88 | 1.125412341 | 1.322698073 | 0.7799511 | 2.316991997 |
| CD89 | 1.155113513 | 1.021413276 | 0.860685697 | 1.45844504 |
| CD90 | 334.0429043 | 113.6047109 | 104.9633253 | 488.2344772 |
| CD91 | 15.1680165 | 2.378873662 | 12.65378973 | 19.75871314 |
| CD93 | 4.010327822 | 1.369398532 | 1.83 | 0.938283224 |
| CD94 | 0.848184818 | 0.922913386 | 0.768391198 | 0.949061682 |
| CD95 | 20.56185611 | 18.89293362 | 30.41564792 | 19.49061662 |
| CD97 | 2.706276827 | 14.82564593 | 17.82396688 | 38.18723861 |
| CD98 | 240.7755776 | 96.78680857 | 40.34259839 | 172.5201072 |
| CD99 | 75.14211886 | 60.72434608 | 34.77831863 | 78.27329193 |
| CD98R | 5.757375758 | 8.458684654 | 8.556810929 | 6.003683341 |
| CD100 | 1.090759876 | 1.503211991 | 1.841564793 | 1.184857641 |
| CD102 | 2.842377361 | 12.75653924 | 1.835335689 | 5.689440994 |
| CD103 | 0.9908901 | 0.946466809 | 0.963125183 | 0.983468255 |
| CD105 | 15.18151815 | 16.46680942 | 16.38361858 | 17.72317963 |
| CD106 | 1.46030604 | 3.854389721 | 0.858190709 | 4.932975871 |
| CD107a | 1.9966967 | 2.398286938 | 3.423982885 | 2.045376498 |
| CD107b | 2.640264026 | 1.985738758 | 2.640586797 | 1.45844504 |
| CD108 | 17.23514312 | 4.567404437 | 15.65371833 | 7.80631118 |
| CD109 | 1.537963795 | 3.162740899 | 1.073349633 | 1.664879357 |
| CD112 | 3.894389439 | 2.655346253 | 2.444987775 | 3.866589812 |
| CD114 | 0.920793079 | 1.365524635 | 1.234938875 | 1.337881609 |
| CD116 | 1.041414141 | 0.773716665 | 0.49728776 | 0.615101289 |

FIG. 13 CONT.

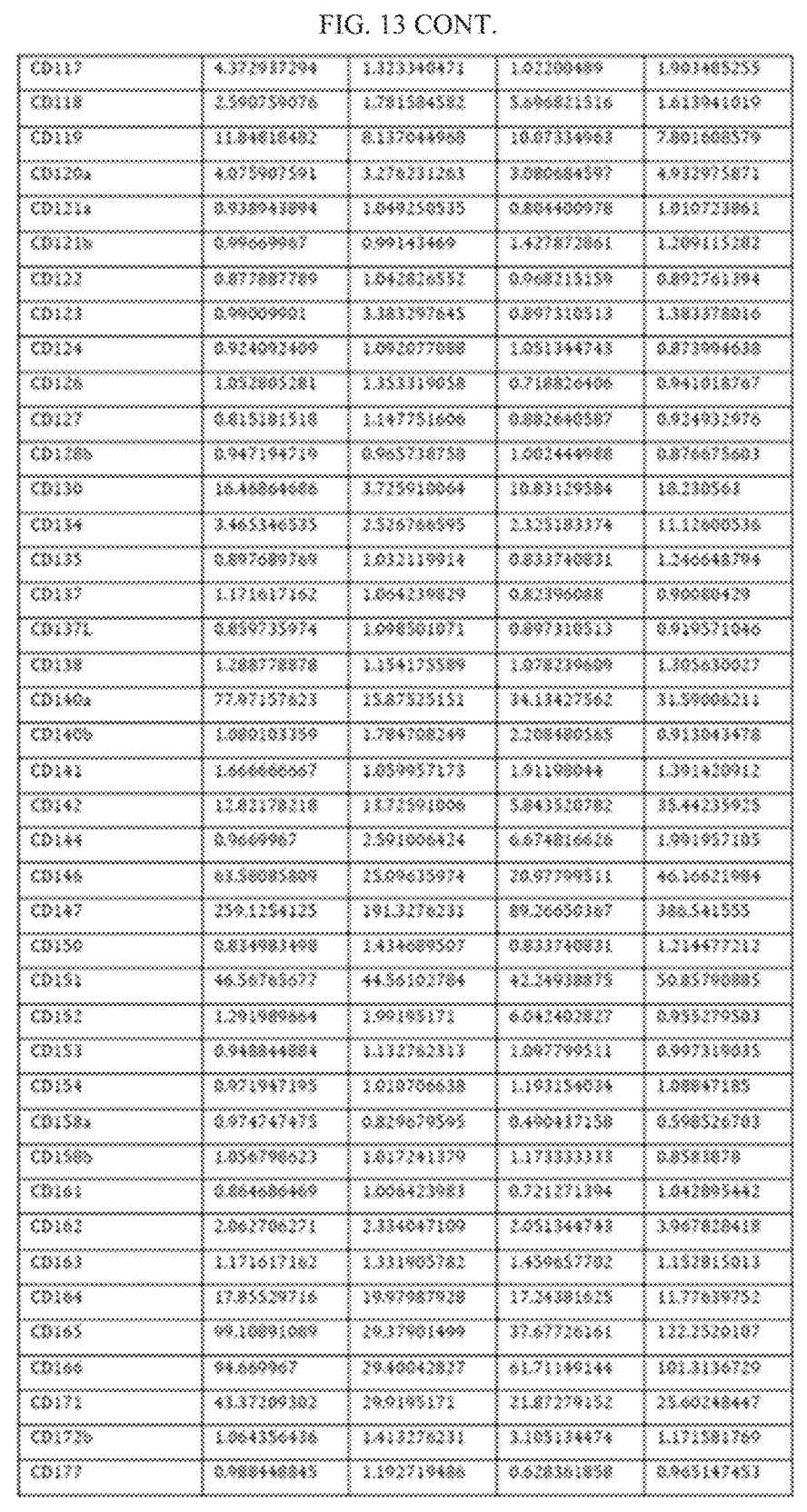

| | | | |
|---|---|---|---|
| CD117 | 4.372987294 | 1.323346471 | 1.02398489 | 1.801485255 |
| CD118 | 2.590759076 | 1.781584582 | 5.696811316 | 1.613941019 |
| CD119 | 11.84818482 | 8.137044968 | 18.87334968 | 7.801668579 |
| CD120a | 4.073907591 | 3.278231283 | 3.080684897 | 4.913975871 |
| CD121a | 0.938943894 | 1.848258535 | 0.804480978 | 1.010723861 |
| CD121b | 0.94669987 | 0.99143469 | 1.427873861 | 1.209115282 |
| CD122 | 0.877887789 | 1.843828552 | 0.968313139 | 0.892761394 |
| CD123 | 0.98009901 | 1.383397845 | 0.897318513 | 1.383378016 |
| CD124 | 0.924093409 | 1.092077888 | 1.051344743 | 0.873994638 |
| CD126 | 1.052885281 | 1.353319058 | 0.718826406 | 0.941018787 |
| CD127 | 0.815181318 | 1.147731606 | 0.882646587 | 0.924032976 |
| CD128b | 0.947194719 | 0.965738758 | 1.062444988 | 0.876675683 |
| CD130 | 16.46864688 | 3.735910064 | 10.83139584 | 18.230563 |
| CD134 | 3.465346535 | 3.536768595 | 2.325183374 | 11.11288053A |
| CD135 | 0.887689789 | 1.032119914 | 0.833740831 | 1.246648794 |
| CD137 | 1.171817162 | 1.864239829 | 0.82396088 | 0.99008429 |
| CD137L | 0.859733974 | 1.99858107L | 0.897318513 | 0.919571086 |
| CD138 | 1.288778878 | 1.154175589 | 1.078339609 | 1.305638037 |
| CD140a | 77.97157823 | 15.87535151 | 34.13427362 | 31.59006211 |
| CD140b | 1.889183359 | 1.784708349 | 2.208480585 | 0.913843478 |
| CD141 | 1.666668667 | 1.839857173 | 1.91198044 | 1.391620912 |
| CD142 | 13.82178218 | 18.73591808 | 5.843518782 | 35.44235925 |
| CD144 | 0.9669987 | 2.391006424 | 6.074816628 | 1.991927105 |
| CD146 | 63.38885809 | 25.09635974 | 20.97799311 | 46.16621984 |
| CD147 | 239.1254123 | 191.3278231 | 89.36650387 | 386.561555 |
| CD150 | 0.834983498 | 1.434689507 | 0.833740831 | 1.214477212 |
| CD151 | 46.36768677 | 44.36103784 | 42.24938873 | 50.85798885 |
| CD152 | 1.291980864 | 1.99185171 | 6.042403827 | 0.835279503 |
| CD153 | 0.948844884 | 1.132782313 | 1.897799511 | 0.997319035 |
| CD154 | 0.971847195 | 1.018766638 | 1.193154034 | 1.88847185 |
| CD158a | 0.974747475 | 0.829679595 | 0.490437138 | 0.598526703 |
| CD158b | 1.856798623 | 1.817241379 | 1.173333333 | 0.858878 |
| CD161 | 0.864686469 | 1.006423983 | 0.721271394 | 1.042895442 |
| CD162 | 2.86278271 | 3.334047109 | 2.051344743 | 3.967828418 |
| CD163 | 1.171617182 | 1.331805782 | 1.459857782 | 1.153815013 |
| CD164 | 17.85529716 | 19.97987928 | 17.34381625 | 11.77839752 |
| CD165 | 99.10891089 | 29.37901409 | 37.67726161 | 132.2520107 |
| CD166 | 94.669987 | 39.46042837 | 61.71149144 | 101.3136739 |
| CD171 | 43.37209302 | 28.9185171 | 21.87279152 | 23.60248447 |
| CD173b | 1.064356436 | 1.413278231 | 3.185134474 | 1.171581769 |
| CD177 | 0.988448845 | 1.192719488 | 0.628361858 | 0.963147453 |

FIG. 13 CONT.

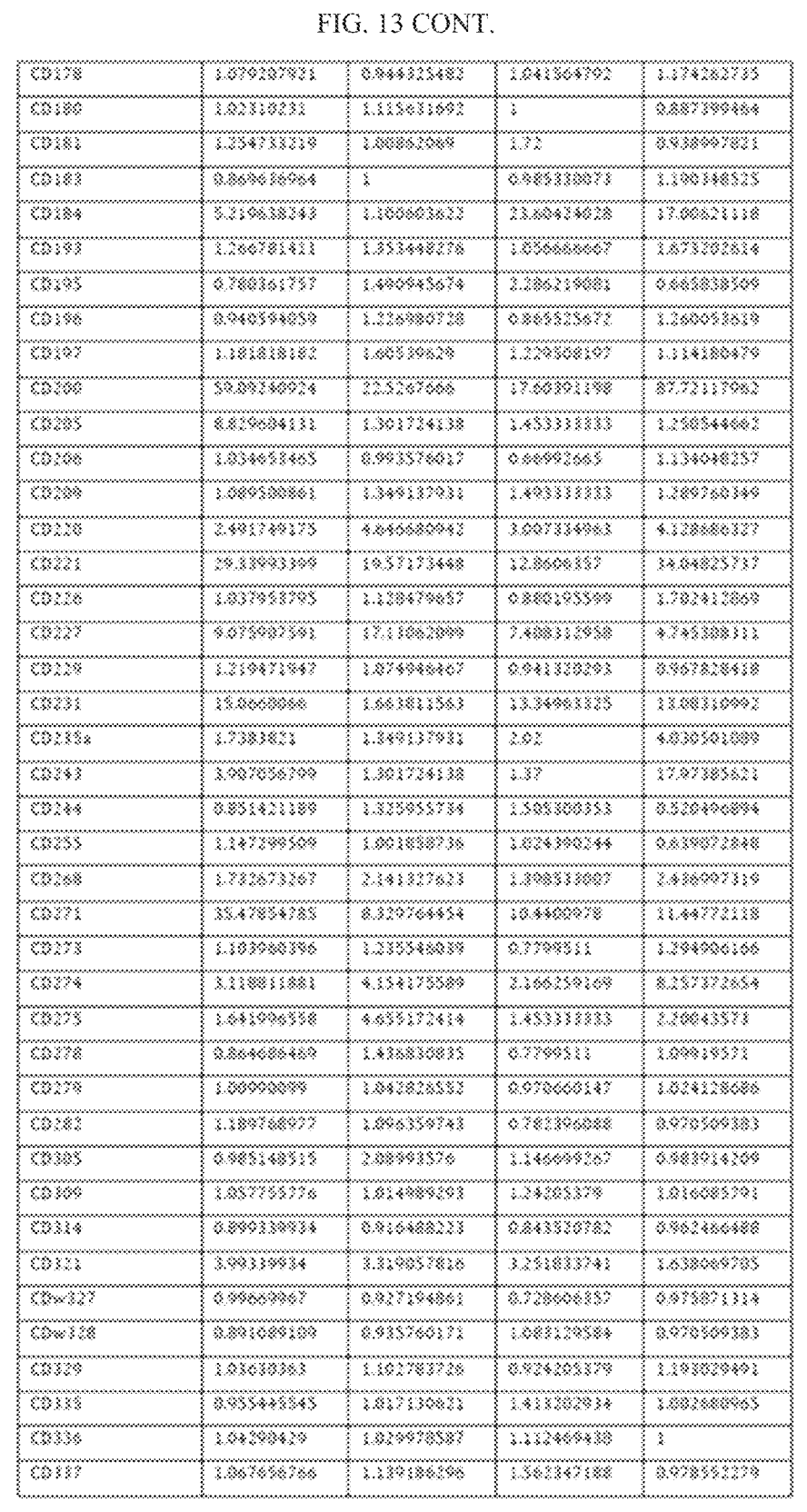

| | | | |
|---|---|---|---|
| CD178 | 1.079207921 | 0.944925483 | 1.041364792 | 1.174282735 |
| CD180 | 1.02310231 | 1.115631692 | 1 | 0.887399464 |
| CD181 | 1.354733319 | 1.00862069 | 1.72 | 0.938447821 |
| CD183 | 0.869618964 | 1 | 0.985338073 | 1.180348525 |
| CD184 | 5.219638343 | 1.180603623 | 23.80434028 | 17.00521138 |
| CD193 | 1.266781411 | 1.353448278 | 1.856886667 | 1.873282814 |
| CD195 | 0.788361737 | 1.480945674 | 2.286219081 | 0.665838509 |
| CD196 | 0.940594059 | 1.226980728 | 0.866525672 | 1.260093619 |
| CD197 | 1.181818182 | 1.66539628 | 1.229508197 | 1.114186479 |
| CD200 | 59.09386924 | 22.5267666 | 17.60391198 | 87.73117982 |
| CD205 | 8.839694131 | 1.301734138 | 1.453333333 | 1.258544462 |
| CD206 | 1.036403465 | 0.993576017 | 0.66992665 | 1.134048257 |
| CD209 | 1.089530861 | 1.349137931 | 1.453333333 | 1.289760369 |
| CD218 | 2.491749175 | 4.64668094 | 3.007334063 | 4.128866337 |
| CD221 | 29.33943399 | 19.57173448 | 12.8606837 | 34.04825737 |
| CD226 | 1.037953795 | 1.128479687 | 0.880193599 | 1.782412869 |
| CD227 | 9.075907591 | 17.1862899 | 7.488312938 | 4.743088311 |
| CD229 | 1.319471947 | 1.87494867 | 0.941323293 | 0.867283418 |
| CD231 | 15.0668066 | 1.661811363 | 13.34963335 | 13.08310992 |
| CD235a | 1.7383821 | 1.349137931 | 2.02 | 4.030501889 |
| CD243 | 3.007656799 | 1.301734138 | 1.37 | 17.97385821 |
| CD244 | 0.851821189 | 1.323955734 | 1.508380353 | 3.328946894 |
| CD255 | 1.147399509 | 1.001888738 | 1.024390244 | 0.639072848 |
| CD268 | 1.732673267 | 2.141327623 | 1.398833007 | 2.438097319 |
| CD271 | 35.47854785 | 8.329764454 | 10.4400978 | 11.44772118 |
| CD273 | 1.103980396 | 1.233548039 | 0.7799511 | 1.394006166 |
| CD274 | 3.118811881 | 4.154175589 | 3.166259169 | 8.257372854 |
| CD275 | 1.641996558 | 4.655172414 | 1.453333333 | 2.28043571 |
| CD278 | 0.864686489 | 1.436830835 | 0.7799511 | 1.09919571 |
| CD279 | 1.50990099 | 1.843828533 | 0.970660147 | 1.824128686 |
| CD282 | 1.189768977 | 1.896359743 | 0.783396088 | 0.970569383 |
| CD285 | 0.983148515 | 2.08993576 | 1.146699267 | 0.683914209 |
| CD309 | 1.057755776 | 1.814889393 | 1.24385379 | 1.016085791 |
| CD314 | 0.899339934 | 0.816488233 | 0.843336782 | 0.962466488 |
| CD321 | 3.99339934 | 3.318057816 | 3.251833741 | 1.638069785 |
| CDw327 | 0.99669967 | 0.927194861 | 0.728606837 | 0.97587131 |
| CDw328 | 0.891689199 | 0.935760171 | 1.088129589 | 0.970569383 |
| CD329 | 1.03630363 | 1.10278372 | 0.924205379 | 1.19382949 |
| CD335 | 0.935445545 | 1.81713082 | 1.41328294 | 1.082680965 |
| CD336 | 1.0429842 | 1.029978587 | 1.112464438 | 1 |
| CD337 | 1.067656766 | 1.139186396 | 1.563347188 | 0.978992279 |

FIG. 13 CONT.

| | | | | |
|---|---|---|---|---|
| CD338 | 6.884681583 | 1.920258621 | 3.14 | 6.993464052 |
| CD304 | 2.04620462 | 2.184154176 | 8.728606857 | 6.648793566 |
| abTCR | 1.393803604 | 1.888781518 | 2.354088361 | 0.979743173 |
| B2microglobulin | 341.0866061 | 18.1618887 | 14.79508197 | 262.2836098 |
| BLTR-1 | 1.074257416 | 1.254817987 | 0.924265379 | 1.371045576 |
| CLIP | 1.227722772 | 2.933618844 | 1.13202934 | 1.00536193 |
| CMRF-44 | 1.008417808 | 1.413153457 | 2.172131148 | 0.845303867 |
| CMRF-56 | 1.05380928 | 0.985010797 | 1.246943765 | 0.97190349 |
| EGF Receptor | 6.540447504 | 7.7588386 | 11.73333333 | 8.888888889 |
| fMLP receptor | 0.95379538 | 0.96359743 | 1.668459658 | 1.304101877 |
| ydTCR | 1.161716173 | 0.931477518 | 1.380953545 | 0.938294904 |
| HPC | 1.541254125 | 2.038543897 | 0.789731031 | 1.705093834 |
| HLA-ABC | 295.9735974 | 286.3381298 | 64.54767726 | 758.2037534 |
| HLA-A2 | 1.287435456 | 1.114224138 | 1.25 | 843.4204793 |
| HLA-DQ | 9.728682171 | 3.796780084 | 16.89043938 | 11.50310559 |
| HLA-DR | 64.68992248 | 1.690148845 | 1.522968198 | 0.785093168 |
| HLA-DR_DP_DQ | 66.25322997 | 1.227384185 | 1.448763231 | 0.857142857 |
| Invariant NK T | 1.188318832 | 1.269807381 | 0.992665037 | 1.168319839 |
| GD2 | 816.9509044 | 71.67243461 | 234.8763231 | 1389.167782 |
| MIC A/B | 6.896840827 | 4.346076459 | 2.795053004 | 1.50310559 |
| NKB1 | 1.021452145 | 1.113490364 | 1.041564792 | 1.731903485 |
| SSEA-3 | 19.29292929 | 6.930868034 | 26.11202186 | 41.58379374 |
| SSEA-4 | 9.623587921 | 1.323429074 | 1.87804878 | 0.971854305 |
| TRA-1-60 | 1.237373737 | 0.937605396 | 0.802622991 | 1.186003883 |
| TRA-1-81 | 1.515151515 | 1.543001686 | 0.504098361 | 1.167587977 |
| VB23 | 1.383838383 | 1.033533191 | 0.851100244 | 1.174263735 |
| VB8 | 1.354561103 | 1.372413793 | 1.146666667 | 1.117647059 |
| CD328 | 2.04620462 | 3.059957173 | 3.69193154 | 1.941018767 |
| CD49f | 10.13962963 | 10.19753086 | 19.82718049 | 54.40056804 |
| CD104 | 1.894366197 | 3.346508364 | 0.599071207 | 1.860006061 |
| CD120b | 2.176058338 | 2.015810277 | 1.018035913 | 1.25 |
| CD132 | 1.323943863 | 1.110671937 | 0.843853251 | 0.687878788 |
| CD201 | 1.018957346 | 2.810086081 | 1.896618357 | 1.084483759 |
| CD210 | 1.549382716 | 0.731461481 | 1.259259259 | 2.264150943 |
| CD212 | 1.611111111 | 0.867283951 | 1.105061728 | 1.367924528 |
| CD267 | 1.461234568 | 0.660329218 | 1.29382716 | 1.662264131 |
| CD294 | 1.197530864 | 0.730452675 | 0.895061728 | 1.286792453 |
| SSEA-3 | 1.326530612 | 0.612359551 | 0.856980892 | 1.84850214 |
| CLA | 1.319387755 | 1.573037708 | 0.617647059 | 0.861626248 |
| Integrin_7 | 1.456790123 | 1.800411523 | 1.930864198 | 2.366037736 |

SEQUENCE LISTING

Sequence total quantity: 17
SEQ ID NO: 1              moltype = DNA   length = 20
FEATURE                   Location/Qualifiers
source                    1..20
                          mol_type = other DNA
                          organism = synthetic construct
SEQUENCE: 1
actggtcact tacagcagcc                                                    20

SEQ ID NO: 2              moltype = DNA   length = 20
FEATURE                   Location/Qualifiers
source                    1..20
                          mol_type = other DNA
                          organism = synthetic construct
SEQUENCE: 2
ggttttgcac agcgaggaag                                                    20

SEQ ID NO: 3              moltype = DNA   length = 20
FEATURE                   Location/Qualifiers
source                    1..20
                          mol_type = other DNA
                          organism = synthetic construct
SEQUENCE: 3
cacaccctga accagttcga                                                    20

SEQ ID NO: 4              moltype = DNA   length = 20
FEATURE                   Location/Qualifiers
source                    1..20
                          mol_type = other DNA
                          organism = synthetic construct
SEQUENCE: 4
agagcatgtg gtatgacggg                                                    20

SEQ ID NO: 5              moltype = DNA   length = 22
FEATURE                   Location/Qualifiers
source                    1..22
                          mol_type = other DNA
                          organism = synthetic construct
SEQUENCE: 5
attaagagag gcctccagtt tg                                                 22

SEQ ID NO: 6              moltype = DNA   length = 20
FEATURE                   Location/Qualifiers
source                    1..20
                          mol_type = other DNA
                          organism = synthetic construct
SEQUENCE: 6
ccatacctcc cctgtccaga                                                    20

SEQ ID NO: 7              moltype = DNA   length = 20
FEATURE                   Location/Qualifiers
source                    1..20
                          mol_type = other DNA
                          organism = synthetic construct
SEQUENCE: 7
gcgggtgtct tatgcggata                                                    20

SEQ ID NO: 8              moltype = DNA   length = 20
FEATURE                   Location/Qualifiers
source                    1..20
                          mol_type = other DNA
                          organism = synthetic construct
SEQUENCE: 8
aggccactgc tcctctgata                                                    20

SEQ ID NO: 9              moltype = DNA   length = 20
FEATURE                   Location/Qualifiers
source                    1..20
                          mol_type = other DNA
                          organism = synthetic construct
SEQUENCE: 9
tcaaggtcag acagtggtgc                                                    20

SEQ ID NO: 10             moltype = DNA   length = 20
FEATURE                   Location/Qualifiers
source                    1..20
                          mol_type = other DNA
                          organism = synthetic construct -continued

```
SEQUENCE: 10
atcccaccat ttcccaccac                                                    20

SEQ ID NO: 11              moltype = DNA   length = 20
FEATURE                    Location/Qualifiers
source                     1..20
                           mol_type = other DNA
                           organism = synthetic construct
SEQUENCE: 11
cctcagctcc aggcatcttg                                                    20

SEQ ID NO: 12              moltype = DNA   length = 19
FEATURE                    Location/Qualifiers
source                     1..19
                           mol_type = other DNA
                           organism = synthetic construct
SEQUENCE: 12
catgaccccc tggctcaat                                                     19

SEQ ID NO: 13              moltype = DNA   length = 20
FEATURE                    Location/Qualifiers
source                     1..20
                           mol_type = other DNA
                           organism = synthetic construct
SEQUENCE: 13
tctcgagcaa gacgttcagt                                                    20

SEQ ID NO: 14              moltype = DNA   length = 20
FEATURE                    Location/Qualifiers
source                     1..20
                           mol_type = other DNA
                           organism = synthetic construct
SEQUENCE: 14
gcgggtgtct tatgcggata                                                    20

SEQ ID NO: 15              moltype = RNA   length = 20
FEATURE                    Location/Qualifiers
source                     1..20
                           mol_type = other RNA
                           organism = synthetic construct
SEQUENCE: 15
cgtcccgggt gctcgcgtac                                                    20

SEQ ID NO: 16              moltype = RNA   length = 20
FEATURE                    Location/Qualifiers
source                     1..20
                           mol_type = other RNA
                           organism = synthetic construct
SEQUENCE: 16
ccggctacct cttgcgccgt                                                    20

SEQ ID NO: 17              moltype = RNA   length = 20
FEATURE                    Location/Qualifiers
source                     1..20
                           mol_type = other RNA
                           organism = synthetic construct
SEQUENCE: 17
ggggccacta gggacaggat                                                    20
```

METHODS FOR TREATMENT OF CANCERS HARBORING AN H3K27M MUTATION

CROSS-REFERENCE TO RELATED APPLICATIONS

This application is a continuation application of U.S. patent application Ser. No. 16/629,604, filed Jan. 9, 2020, which was a U.S. 371 national phase entry of International Patent Application No. PCT/US2018/041839, filed Jul. 12, 2018, which claims priority to U.S. Provisional Patent Application 62/651,406, filed Apr. 2, 2018, and U.S. Provisional Patent Application 62/531,872, filed Jul. 12, 2017, each of which is incorporated by reference in their entireties.

FIELD OF THE INVENTION

The present invention relates to the immunotherapeutic treatment of cancer. In particular, the invention relates to methods of treating cancer carrying a histone H3 K27M (H3K27M) mutation (e.g., glioma with H3K27M mutation) using immunotherapeutic compositions comprising immune cells engineered to express GD2-specific chimeric antigen receptors. Compositions and methods of the invention find use in both clinical and research settings, for example, within the fields of biology, immunology, medicine, and oncology.

SEQUENCE LISTING STATEMENT

The contents of the electronic sequence listing titled STDU2-35343-304.xml (Size: 16,029 bytes; and Date of Creation: Jul. 26, 2022) is herein incorporated by reference in its entirety.

BACKGROUND

Cancer is one of the most devastating diseases both in terms of human life opportunity loss and health care cost. It also presents unmet clinical needs. Cancer is typically treated with surgery, chemotherapy, radiation therapy, or a combination thereof. These treatments, however, often have significant side effects including immune system suppression, destruction of normal cells in the body, autoimmunity, aberrant cellular metabolism, and even metastasis and the onset of secondary cancer.

Diffuse intrinsic pontine glioma (DIPG) and other histone H3 K27M (H3K27M) mutated midline gliomas are examples of extremely aggressive and universally fatal pediatric cancers. While much progress has been achieved characterizing the molecular origins of these tumors, improvements in clinical management have remained elusive, with median survival for DIPG remaining approximately 10 months. Immunotherapy agents including checkpoint inhibitors have provided substantial clinical benefit in numerous adult cancers refractory to traditional therapies, but these agents have not yet demonstrated conclusive benefit in childhood cancers such as DIPG.

SUMMARY

The present invention relates to the immunotherapeutic treatment of cancer. In particular, the invention relates to methods of treating cancers carrying a histone H3 K27M (H3K27M) mutation (e.g., a DIPG with an H3K27M mutation) using immunotherapeutic compositions comprising immune cells engineered to express GD2-specific chimeric antigen receptors (GD2 CARs).

As described herein, new targets and strategies for immunotherapy have been identified for H3K27M mutated cancers (e.g., diffuse gliomas (e.g., diffuse midline glioma and diffuse intrinsic pontine glioma (DIPG))). In particular, the invention identified significant and remarkably high levels of disialoganglioside GD2 expression occurring in the context of diffuse glioma.

Accordingly, in one aspect, a method of treating cancer characterized by an H3K27M mutation is provided, the method comprising administering to an individual (e.g., a patient) having such a cancer an effective amount of immune cells genetically modified to express a chimeric antigen receptor (CAR) specific for GD2. In certain embodiments, the cancer is a glioma. In some embodiments, the glioma is diffuse intrinsic pontine glioma (DIPG). In other embodiments, the cancer is diffuse midline glioma. However, the invention is not so limited. Indeed, any cancer having an H3K27M mutation may be treated with the compositions and methods described herein.

In certain embodiments, the immune cells genetically modified to express a chimeric antigen receptor (CAR) specific for GD2 are T cells. The invention is not limited by the type of T cell so modified. In some embodiments, the T cells are CD3+ T cells (e.g., a combination of CD4+ and CD8+ T cells). In certain embodiments, the T cells are CD8+ T cells. In other embodiments, the T cells are CD4+ T cells. In some embodiments, the T cells are natural killer (NK) T cells. In some embodiments, the T cells are gamma delta T cells. In some embodiments, the T cells are a combination of CD4+ and CD8 T+ cells (e.g., that are CD3+). In certain embodiments, the T cells are memory T cells (e.g., tissue-resident memory T (Trm) cells, stem memory TSCM cells, or virtual memory T cells). In certain embodiments, the T cells are a combination of CD8+ T cells, CD4+ T cells, NK T cells, memory T cells, and/or gamma delta T cells. In some embodiments, the modified immune cells are cytokine-induced killer cells.

In certain embodiments, the CAR expressed in immune cells is any CAR that specifically recognizes GD2 (e.g., that binds with specificity to an epitope of GD2 (e.g., GalNAcβ1-4(NeuAcα2-8NeuAcα2-3)Gal)). The invention is not limited by the type of GD2-specific CAR. Indeed, any CAR that binds with specificity to GD2 may be used to genetically modify (e.g., to be expressed in) immune cells. Exemplary CARs include, but are not limited to, CAR that includes the GD2 binding domain of a GD2-specific antibody such as, but not limited to, 14G2a, ch14.18, hu14.18K322A, m3F8, hu3F8-IgG1, hu3F8-IgG4, HM3F8, and DMAb-20. In certain embodiments, the antigen binding domain is a single-chain variable fragment (scFv) containing heavy and light chain variable regions that recognize or specifically bind an epitope of GD2. In some embodiments, the CAR further comprises a transmembrane domain (e.g., a T cell transmembrane domain (e.g., a CD28 transmembrane domain)) and a signaling domain comprising one or more immunoreceptor tyrosine-based activation motifs (ITAMs)(e.g., a T cell co-receptor signaling domain (e.g., a CD3-zeta chain (CD3ζ)). In some embodiments, the CAR comprises one or more co-stimulatory domains (e.g., domains that provide a second signal to stimulate T cell activation. The invention is not limited by the type of co-stimulatory domain. Indeed, any co-stimulatory domain known in the art may be used including, but not limited to, CD28, OX40/CD134, 4-1BB/CD137/TNFRSF9, FcεRIγ, ICOS/CD278, ILRB/CD122, IL-2RG/CD132, and CD40. In certain embodiments, the co-stimulatory domain is 4-1BB.

In certain embodiments, the present invention provides that exposure of animals (e.g., humans) suffering from cancers characterized by H3K27M-expressing cells (e.g., a DIPG with H3K27M-expressing cells) to therapeutically effective amounts of immunotherapeutic compositions comprising immune cells genetically modified to express GD2-specific CAR inhibits the growth of such H3K27M-expressing cancer cells or supporting cells outright and/or renders such cells as a population more susceptible to other treatments (e.g., the cell death-inducing activity of cancer therapeutic drugs or radiation therapies).

The present invention contemplates that the methods and compositions thereof described herein satisfy a long-felt but unmet medical need for the treatment of pediatric brain cancers, particularly those cancer types characterized by H3K27M-expressing cells, either when administered as a monotherapy (e.g., to kill cancer cells, and/or induce cell growth inhibition, apoptosis and/or cell cycle arrest in cancer cells), or when administered in a temporal relationship with additional agent(s) (e.g., in combination therapies), such as other cell death-inducing or cell cycle-disrupting cancer therapeutic drugs or radiation therapies (e.g., to render a greater proportion of the cancer cells susceptible to executing the apoptosis program compared to the corresponding proportion of cells in an animal treated only with the cancer therapeutic drug or radiation therapy alone).

Accordingly, in certain embodiments, the invention provides methods of treating or delaying the progression of cancer in a patient, wherein the cancer is characterized by a histone H3 K27M (H3K27M) mutation, the methods comprising: obtaining a biological sample comprising cancer cells from the patient; determining the presence or absence of an H3K27M mutation within the cancer cells; and administering to the patient a therapeutically effective amount of a composition comprising T cells genetically modified to express a chimeric antigen receptor (CAR) specific for GD2 if the cancer cells are characterized as having H3K27M mutation. In certain embodiments, the therapeutically effective amount of the genetically modified T cell composition comprising GD2-specific CAR T cells reduces the number of H3K27M positive cancer cells in the patient following such treatment. In certain embodiments, the therapeutically effective amount of the genetically modified T cell composition comprising GD2-specific CAR T cells reduces and/or clears the tumor burden in the patient following such treatment. In certain embodiments, the administering occurs before, at the same time, and/or after the patient receives radiation therapy. In certain embodiments, the method further comprises administering to the patient one or more anticancer agents and/or one or more chemotherapeutic agents. In certain embodiments, combination treatment of a patient with a therapeutically effective amount of T cells genetically modified to express a chimeric antigen receptor (CAR) specific for GD2 and a course of an anticancer agent produces a greater tumor response and clinical benefit in such patient compared to those treated with the modified T cells or anticancer drugs/radiation alone. Since the doses for all approved anticancer drugs and radiation treatments are known, the present invention contemplates the various combinations of them with the modified T cells.

In certain embodiments, the invention provides a therapeutically effective amount of a composition (e.g., an immunotherapeutic composition) comprising T cells genetically modified to express a chimeric antigen receptor (CAR) specific for GD2 (e.g., for use in treating or delaying the progression of cancer in a subject (e.g., wherein the cancer harbors a histone H3 K27M (H3K27M) mutation)). As described herein, the composition may further comprise one or more anticancer agents and/or one or more chemotherapeutic agents. The invention also provides the use of the composition to induce cell cycle arrest and/or apoptosis in H3K27M-expressing cells (e.g., DIPG characterized by H3K27M-expressing cells). The invention also relates to the use of the compositions for sensitizing cells to additional agent(s), such as inducers of apoptosis and/or cell cycle arrest, and chemoprotection of normal cells through the induction of cell cycle arrest prior to treatment with chemotherapeutic agents. Compositions of the invention are useful for the treatment, amelioration, or prevention of disorders, such as any type of cancer characterized by H3K27M-expressing cells (e.g., DIPG characterized by H3K27M-expressing cells) and additionally any cells responsive to induction of apoptotic cell death (e.g., disorders characterized by dysregulation of apoptosis, including hyperproliferative diseases such as cancer). In certain embodiments, the compositions can be used to treat, ameliorate, or prevent a cancer characterized by H3K27M-expressing cells (e.g., DIPG characterized by H3K27M-expressing cells) that additionally is characterized by resistance to cancer therapies (e.g., those cancer cells which are chemoresistant, radiation resistant, hormone resistant, and the like). The invention also provides pharmaceutical compositions comprising the composition (e.g., immunotherapeutic compositions) comprising T cells genetically modified to express a chimeric antigen receptor (CAR) specific for GD2 in a pharmaceutically acceptable carrier.

The invention further provides kits comprising one or more of the described compositions (e.g., immunotherapeutic compositions) comprising T cells genetically modified to express a chimeric antigen receptor (CAR) specific for GD2 for use according to the description provided herein. For example, in certain embodiments, the invention provides kits comprising one or more of the described compositions (e.g., immunotherapeutic compositions) comprising T cells genetically modified to express a chimeric antigen receptor (CAR) specific for GD2 and instructions for administering the composition to an animal (e.g., diagnosed as having an H3K27M cancer). The kits may optionally contain other therapeutic agents, e.g., anticancer agents or apoptosis-modulating agents. In some embodiments, the kit comprises a medicament comprising T cells genetically modified to express a chimeric antigen receptor (CAR) specific for GD2, an optional pharmaceutically acceptable carrier, and a package insert comprising instructions for administration of the medicament for treating or delaying progression of cancer in an individual.

DESCRIPTION OF THE DRAWINGS

FIG. 1A shows flow cytometry-based screening of cell surface antigens in patient-derived DIPG cell cultures. Four independent low-passage (<12) cultures derived from donated post-mortem DIPG patients were expanded under serum-free neurosphere-forming culture conditions, and surface antigens were profiled using a panel of 284 monoclonal antibodies (BD Lyoplate). After gating to remove doublets and dead cells, median fluorescence intensity (MFI) of live cells (viability >80% in all assays) stained with target antigen was divided by the MFI of live cells stained with the corresponding isotype control and Log 10-scaled (See FIGS. 3A-3B). FIG. 1B shows that assessment of hit overlap between screened cultures identified a total of 36 hits present at an MFI of at least 10 times isotype control in all screened cultures. FIG. 1C shows flow cytometry staining of histone H3 WT pediatric high grade glioma cultures VU-DIPG10, diagnosed as a DIPG, and pcGBM2, which arose in cortex, display markedly lower GD2 expression levels compared to histone H3 K27M DIPGs. FIG. 1D shows double immunohistochemistry of primary DIPG tumor specimens utilizing an antibody against mutant H3K27M to identify tumor cells and mouse anti-GD2 (14g2a) revealing extensive local GD2 expression in primary DIPG (scale bar=100 microns). FIG. 1E depicts a schematic of the GD2-directed 14g2a scFv;4-1BB;CD3z CAR T cell and control constructs used to evaluate efficacy against DIPG. FIG. 1F shows incubation of DIPG cells with GD2-CAR T cells achieves potent DIPG cell lysis at low effector:target (E:T) ratios, compared to minimal lysis rates under most conditions in the presence of CD19-CAR T cells. FIG. 1G shows incubation of GD2-CAR T cells with DIPG cultures induced substantial cytokine (IFN-g and IL-2) generation compared to minimal production by CD19-CAR T cells. In contrast, VU-DIPG 10, an H3 WT line not expressing GD2 (see FIG. 1C), did not trigger cytokine production by GD2-CAR T cells. FIG. 1H shows Cas9-mediated deletion of GD2 synthase eliminates GD2 expression in DIPG cultures. FIG. 1H(a) SU-DIPG13 cells electroporated with Cas9-gRNA complexes eliminated GD2 surface expression FIG. 1H(b) following an ~45 bp deletion at the gRNA target site (two-tailed T test of variance-covariance matrix of standard errors between modeled indel traces and parent sequence, implemented in Tracking of Indels by Decomposition webtool). As a control, gRNA targeting the AAVS1 locus were used. FIG. 1H(c) shows that Cell Trace Violet proliferation assay performed on GD2-CAR T cells following in vitro incubation with the GD2-negative line VUMC-10 or GD2-high SU-DIPG13 demonstrated antigen-specific proliferation of GD2-CAR T cells. FIG. 1I shows GD2-CAR T-cells do not produce substantial levels of IFN-gamma or IL-2 following co-culture with H3K27M GD2neg line generated using CRISPR/Cas9 to knockout GD2 synthase compared with unmodified control cells or Cas9 targeting the control AAVS1 locus. FIG. 1J depicts pathway analysis of ganglioside enzyme expression. Transcription of target ganglioside synthesis pathway enzymes was assessed by semi-quantitative RT-PCR. A biosynthesis flow diagram is provided where the average expression value (2-dCt(HPRT) of key pathway enzymes (genes in boldface) across each culture of the given genotype is shown, and the arrow size is scaled to the average expression in H3F3A K27M cultures. Across the majority of H3F3A K27M cultures, expression of ganglioside synthesis enzymes upstream of GD2 was substantially increased compared to H3WT pediatric high-grade glioma (pHGG) cultures. Across all cultures, B3GALT4 expression was minimal compared to upstream genes, indicating potentially limited rates of GD2 to GD1b conversion. A heatmap and bar graph representation of expression values for individual cultures in each H3 genotype category (3 biological replicates each with technical duplicates) is provided. Primers utilized for qPCR expression analysis are shown in Example 1, Table 2.

FIG. 2A depicts bioluminescence imaging of NSG mice xenografted with luciferase expressing SU-DIPG 6 into the pons (map for all images: radiance, min=(5×10⁴), max=(5×10⁶)) and infused intravenously with (1×10⁷) GD2-CAR or CD19-CAR T cells as designated. Transduction efficiency was evaluated by flow cytometry with anti-idiotype antibodies prior to administration and was routinely >70%. Between 14 and 28 days post-treatment (DPT), a dramatic and universal antitumor response was observed in GD2-CAR treated mice, while no spontaneous regression was observed in those treated with CD19-CAR T cells. FIG. 2B shows tumor burden over time expressed as fold change in flux. FIG. 2C shows quantification of H3K27M+ tumor cell density within infiltrated brainstem regions of SU-DIPG6 GD2-CAR vs. CD19-CAR T-cell treated mice. Within GD2-CAR T-cell-treated SU-DIPG6 xenografts, approximately 36 H3K27M+ cells remaining per mouse were identified in the sampled volume, compared with approximately 18,596 cells per mouse in the sampled volume of CD19-CAR T-cell treated controls. FIG. 2D shows a representative immunofluorescence confocal microscopy of CD19-CAR and GD2-CAR treated SU-DIPG6 tumors staining for the mutant histone H3K27M. FIGS. 2E-2I show GD2-CAR activity in a second patient-derived orthotopic xenograft model of DIPG, SU DIPG13FL. FIGS. 2E and 2F show bioluminescent imaging over time as above. FIG. 2G is a representative immunofluorescent confocal microscopy of SU-DIPG13FL xenografts treated with CD19- or GD2-CAR T-cells and shows clearance of H3K27M+ tumor cells. FIG. 2H shows tiled immunofluorescence images across engrafted regions. FIG. 2I shows quantification of H3K27M+ tumor cell density within infiltrated brainstem regions of SU DIPG13FL. In SU-DIPG13FL xenografts, approximately 32 total H3K27M+ cells remained in the sampled volume of each GD2-CAR T-cell treated mouse, compared to approximately 31,953 cells per mouse in the sampled volume of CD19-CAR T-cell treated controls. Data as shown are mean±SEM. **p<0.0001, *p<0.001, **p<0.01, *p<0.05 by unpaired 2-tailed Student's t-test with Holm-Sidak correction for multiple comparisons applied for bioluminescence imaging data. Scale bars=100 microns.

FIG. 3A shows SU-DIPG6 and SU-DIPG13FL xenograft tumor burden monitored by in vivo bioluminescence imaging (as shown in FIGS. 2A-2I). To assess whether tumor clearance was complete by this measure, matched region of interest (ROI) measurements of total flux were made over the tumor-bearing region and an uninvolved area of the animal's flank. Fold change above background was then computed as the ratio of tumor ROI flux to background ROI flux (SU-DIPG6 n=10 CD19-CAR, 11 GD2-CAR; SU-DIPG13-FL n=13 CD19-CAR, 14 GD2-CAR). A ratio of 1 therefore indicated clearance of tumor luminescence signal to background levels, which was achieved in both models by DPT40 (*=p<0.05, =p<0.01, *=p<0.0001, 2-tailed Student's t test with Holm-Sidak correction for multiple comparisons). FIG. 3B shows that no statistically significant difference in initial tumor burden as assessed by in vivo bioluminescence imaging existed between animals in CD19-CAR or GD2-CAR treated cohorts of SU-DIPG6, SU-DIPG13FL, or additional H3K27M+ DMG cultures SU-pSCG1 and QCTB-R059 (two-way ANOVA with Tukey correction for multiple comparisons, n.s. =not significant at α=0.05). Scatter points indicate individual mice, bars indicate mean, and error bars indicate SEM.

FIGS. 5A and 5B show DIPG cultures express GD2 at homogenously high levels relative to other GD2-positive tumor cell lines. FIG. 5A shows flow cytometry staining for GD2 (clone 14g2a) on the surface of DIPG cultures revealed stronger and more uniform expression relative to cells derived from other malignancies under investigation for GD2-targeting immunotherapies, including neuroblastoma (KCNR, CHLA136, CHLA255), osteosarcoma (143B, MG63-3), and Ewing sarcoma (TC32, EW8). FIG. 5B shows quantitative estimates of GD2 surface expression obtained using fluorescent bead standards (Quantibrite, BD) for DIPG and other cancer lines.

FIGS. 6A-6H show that GD2-CAR T-cell therapy improves survival in DIPG orthotopic xenografts. FIG. 6A shows survival analysis of GD2-CAR T-cell treated orthotopic xenografts in SU DIPG-13P*, a particularly aggressive patient-derived xenograft model of DIPG that is lethal within one month of engraftment, revealed a robust survival improvement in GD2-CAR T-cell treated animals (p<0.0001 Log-rank (Mantel-Cox) test, n=22 CD19-CAR and 23 GD2 CAR across 3 independent cohorts (See FIG. 7)). While CD19-CAR T-cell treated xenografts were universally lethal by study endpoint, all GD2-CAR T-cell-treated animals that survived the acute toxicity of therapy survived to study endpoint at which time they manifested GVHD-like symptoms (See FIGS. 8A-8D). FIG. 6B shows hematoxylin-eosin staining of SU-DIPG13P* xenografts at DPT50 demonstrated clearance by GD2-CAR T-cells of highly-infiltrative parenchymal tumor observed throughout the brain in CD19-CAR T-cell-treated controls and normal gross tissue architecture. FIG. 6C shows hematoxylin-eosin staining of SU-DIPG6 GD2-CAR T cell-treated xenograft analyzed at DPT14 demonstrated ventriculomegaly but histologically normal-appearing neurons in cortex, hippocampus, and brainstem (inset images). FIG. 6D shows fluorescence microscopy of DPT7 SU-DIPG13FL xenografts revealed intravenously-administered GD2-CAR-mCherry T-cells infiltrating the engrafted tumor. FIG. 6E shows representative image of infiltrating GD2-CAR-mCherry T cells at DPT14 in a SU-DIPG13FL xenografted medulla demonstrated spatial association with Iba1+ macrophages. FIG. 6F shows representative image of GD2-CAR mCherry T-cell-mediated tumor cell killing with apoptosis of GFP+ tumor cells as evidenced by co-localization with cleaved caspase 3+. FIG. 6G shows tumoricidal activity occurs in proximity to non-apoptotic NeuN+ neurons in the xenografted pons, shown at DPT7 (See FIGS. 10A-10C). FIG. 6H shows representative images of GD2-CAR-mCherry T-cells infiltrating the parenchyma of SU-DIPG13FL xenografts during the period of acute antitumor activity (see FIG. 9).

FIGS. 8A-8D show that onset of xenogeneic graft-versus-host disease limits duration of monitoring in GD2-CAR T cell-treated patient derived xenograft models. Adoptive transfer of human T cells to NSG mice has been shown to result in graft versus host disease. FIG. 8A shows that in SU-DIPG13P* xenografts, mice treated with CD19-CAR T cells display extensive signs of neurological impairment at endpoint consistent with tumor progression, including paralysis and aberrant motor behavior; however, classical signs of GvHD such as hair loss are absent at this timepoint. At this timepoint, animals treated with GD2-CAR T cells appear normal. FIG. 8B shows hematoxylin/eosin staining of skin specimens from CD19 CAR-treated animals at DPT14 appear grossly normal. FIG. 8C shows that by DPT50, GD2-CAR treated animals exhibit extensive hair loss, and FIG. 8D shows hematoxylin/eosin staining of skin specimens reveals extensive lymphocytic infiltrate of dermis and epidermal hyperplasia, consistent with the onset of GvHD. Scale bars for H&E images are 100 um.

FIGS. 10A-10C show cleaved caspase-3 staining of GD2-CAR T cell treated DIPG xenografts. FIG. 10A shows immunofluorescence microscopy of DIPG13-FL xenografts treated with a single intravenous dose of GD2-CAR T cells, euthanized at DPT 7 and stained for the neuronal marker NeuN and the apoptosis marker cleaved caspase 3 (CCasp3). FIG. 10B shows immunofluorescence micrograph of anti-tumor activity in the cerebellum demonstrating intact granule layer neurons in the presence of local antitumor activity. FIG. 10C shows that out of the total population of CCasp3+ cells identified in GD2-CAR T cell-treated xenografts, <2% co-stain for NeuN.

FIGS. 11A-11K show that GD2 CAR T-cell therapy effectively clears multiple types of midline H3K27M mutant pediatric diffuse midline gliomas and is associated with toxicity in thalamic xenografts. FIG. 11A shows anatomic sites of origin of H3K27M+ DMGs. FIGS. 11B and 11C show that patient-derived culture models of H3K27M mutant tumors that arose in the thalamus (QCTB-R059) and spinal cord (SU-pSCG1) highly and uniformly express GD2 as assessed by flowcytometry (FIG. 11B) and induce antigen-dependent secretion of IFNγ and IL-2 when incubated with GD2 or CD19-CAR T-cells in vitro (FIG. 11C). FIGS. 11D and 11E show SU-pSCG1 cells stably transduced to express GFP and luciferase were engrafted into the medulla of NSG mice and treated with intravenous infusion of $1 \times 107$ GD2-CAR T-cells or CD19-CAR T-cells, and substantial clearance of engrafted tumor was observed by DPT14. FIG. 11F shows quantification of H3K27M+ cells remaining in SU-pSCG1 xenografts at study endpoint revealed near complete clearance of engrafted tumor in GD2-CAR T cell treated animals compared to CD19-CAR T-cell controls. FIG. 11G shows tiled immunofluorescence images across affected regions (GFP, H3K27M, and DAPI). FIGS. 11H and 11I show the H3K27M mutant patient-derived cell culture QCTB-R059 was orthotopically engrafted into the thalamus of NSG mice and treated by systemic administration of GD2 or CD19-CAR T-cells as described for SU-pSCG1. Tumor burden over time as determined by bioluminescence imaging illustrated marked reduction by DPT 14, and histological clearance in surviving animals at DPT 30 (see FIG. 12). FIG. 11J provides a diagram showing the risk for 3rd ventricular compression and herniation through the tentorium cerebelli accompanying inflammation in the thalamus. FIG. 11K shows GD2-CAR T-cell therapy-associated deaths in mice with thalamic xenografts observed by DPT14 indicating a potential hazard of immunotherapy for midline tumors. Data as shown are mean±SEM. ***$p<0.001$, *$p<0.05$ by unpaired 2-tailed Student's t-test with Holm-Sidak correction for multiple comparisons.

FIG. 13 shows cell surface antigens screened in patient-derived DIPG cultures. The surface marker expression from BD Lyoplate panel (median fluorescence intensity over isotype control) is shown.

DEFINITIONS

Figure 1A:
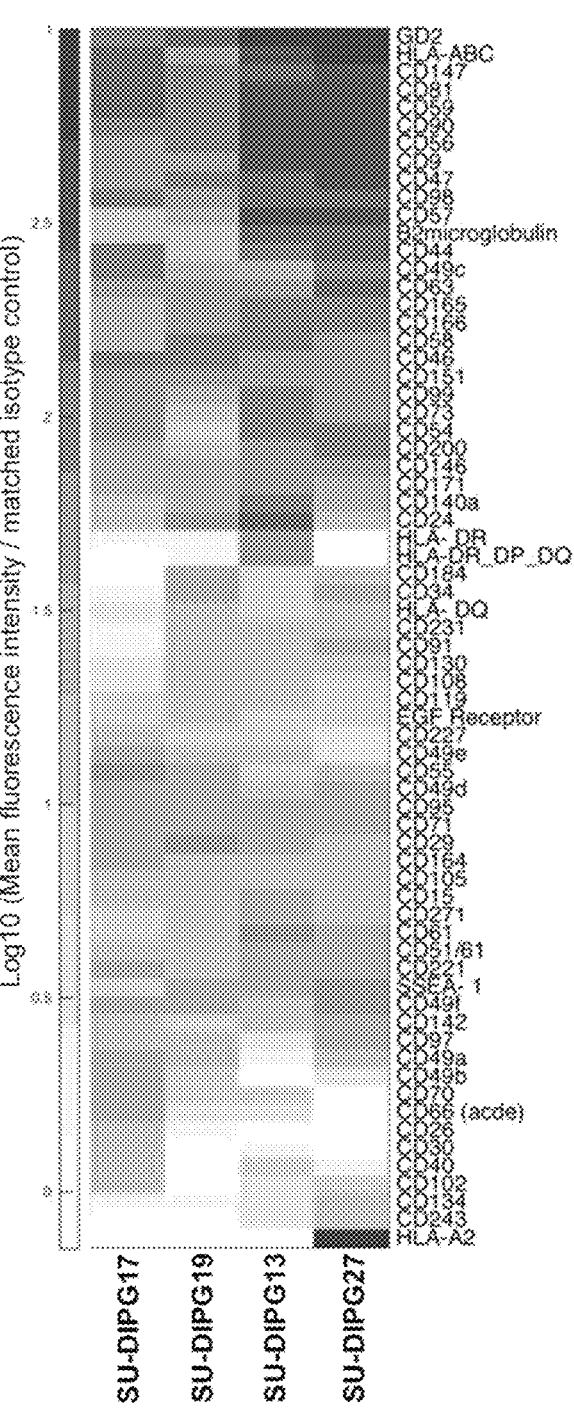
FIGS. 1A-1J show the identification of GD2 overexpression in DIPG.

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., malnutrition, industrial hazards, and/or climate), may be responsive to an inherent or latent defect in the organism (e.g., genetic anomalies) or to combinations of these and other factors.

The terms "host," "subject," or "patient" are used interchangeably herein to refer to an individual to be treated by (e.g., administered) the compositions and methods of the present invention. Subjects include, but are not limited to, mammals (e.g., murines, simians, equines, bovines, porcines, canines, felines, and the like), and most preferably includes humans. In the context of the invention, the term "subject" generally refers to an individual who will be administered or who has been administered one or more compositions of the present invention (e.g., genetically modified immune cells described herein).

The terms "buffer" or "buffering agents" refer to materials that when added to a solution cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution (i.e., two more protons than electrons).

The terms "chelator" or "chelating agent" refer to any materials having more than one atom with a lone pair of electrons that are available to bond to a metal ion.

The term "solution" refers to an aqueous or non-aqueous mixture.

A "disorder" is any condition or disease that would benefit from treatment with a composition or method of the invention. This includes chronic and acute disorders including those pathological conditions which predispose the mammal to the disorder in question. Non-limiting examples of disorders to be treated herein include conditions such as cancer.

The terms "cell proliferative disorder," and "proliferative disorder" refer to disorders that are associated with some degree of abnormal cell proliferation. For example, a "hyperproliferative disorder or disease" is a disease or disorder caused by excessive growth of cells. In one embodiment, the cell proliferative disorder is cancer.

As used herein, the terms "cancer" and "tumor" refer to a cell that exhibits a loss of growth control or tissue of uncontrolled growth or proliferation of cells. Cancer and tumor cells generally are characterized by a loss of contact inhibition, may be invasive, and may display the ability to metastasize. The present invention is not limited by the type of cancer or the type of treatment (e.g., prophylactically and/or therapeutically treated). Indeed, a variety of cancers may be treated with compositions and methods described herein including, but not limited to, brain cancer or other cancers of the central nervous system (e.g., diffuse midline glioma or diffuse intrinsic pontine glioma (DIPG, a highly aggressive glial tumor found at the base of the brain, see, e.g., Louis et al., Acta Neuropathol (2016) 131:803-820), melanomas, lymphomas, epithelial cancer, breast cancer, ovarian cancer, endometrial cancer, colorectal cancer, lung cancer, renal cancer, melanoma, kidney cancer, prostate cancer, sarcomas, carcinomas, and/or a combination thereof.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The term "anticancer agent" as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals, e.g., in humans).

An "effective amount" refers to an amount effective, at dosages and for periods of time necessary, to achieve a desired therapeutic or prophylactic result.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth (e.g., reduces and/or clears tumor burden in the patient (e.g., reduces the number of H3K27M positive cancer cells in a patient)), decreases tumor mass, decreases the number of metastases, decreases tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent, an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 450%, or at least about 500% over the response in the absence of the first agent.

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the terms "administration" and "administering" refer to the act of giving a composition of the present invention to a subject. Exemplary routes of administration to the human body include, but are not limited to, through the eyes (ophthalmic), mouth (oral), skin (transdermal), nose (nasal), lungs (inhalant), oral mucosa (buccal), ear, rectal, by injection (e.g., intravenously, subcutaneously, intraperitoneally, intratumorally, etc.), topically, and the like.

As used herein, the terms "co-administration" and "co-administering" refer to the administration of at least two agent(s) (e.g., genetically modified immune cells and one or more other agents—e.g., anti-cancer agents) or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

The terms "pharmaceutically acceptable" or "pharmacologically acceptable," as used herein, refer to compositions that do not substantially produce adverse reactions (e.g., toxic, allergic or other immunologic reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintegrants (e.g., potato starch or sodium starch glycolate), polyethylene glycol, and the like. The compositions also can include stabilizers and preservatives. Examples of carriers, stabilizers and adjuvants have been described and are known in the art (see, e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts. Examples of bases include, but are not limited to, alkali metal (e.g., sodium) hydroxides, alkaline earth metal (e.g., magnesium) hydroxides, ammonia, and compounds of formula NW4+, wherein W is C1-4 alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as Na+, NH4+, and NW4+(wherein W is a C1-4 alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the term "at risk for disease" refers to a subject that is predisposed to experiencing a particular disease. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk (e.g., a subject may be "at risk for disease" simply by being exposed to and interacting with other people), nor is it intended that the present invention be limited to any particular disease (e.g., cancer).

As used herein, the term "kit" refers to any delivery system for delivering materials. In the context of immunotherapeutic agents, such delivery systems include systems that allow for the storage, transport, or delivery of immunogenic agents and/or supporting materials (e.g., written instructions for using the materials, etc.) from one location to another. For example, kits include one or more enclosures (e.g., boxes) containing the relevant immunotherapeutic agents (e.g., genetically modified immune cells and/or supporting materials). As used herein, the term "fragmented kit" refers to delivery systems comprising two or more separate containers that each contain a subportion of the total kit components. The containers may be delivered to the intended recipient together or separately. For example, a first container may contain a composition comprising an immunotherapeutic composition for a particular use, while a second container contains a second agent (e.g., a chemotherapeutic agent). Indeed, any delivery system comprising two or more separate containers that each contains a subportion of the total kit components are included in the term "fragmented kit." In contrast, a "combined kit" refers to a delivery system containing all of the components of an immunogenic agent needed for a particular use in a single container (e.g., in a single box housing each of the desired components). The term "kit" includes both fragmented and combined kits.

As used herein, the term "immunoglobulin" or "antibody" refer to proteins that bind a specific antigen. Immunoglobulins include, but are not limited to, polyclonal, monoclonal, chimeric, and humanized antibodies, as well as Fab fragments and F(ab')2 fragments of the following classes: IgG, IgA, IgM, IgD, IgE, and secreted immunoglobulins (sIg). Immunoglobulins generally comprise two identical heavy chains and two light chains. However, the terms "antibody" and "immunoglobulin" also encompass single chain antibodies and two chain antibodies.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthun, in The Pharmacology of Monoclonal Antibodies, vol. 113, Rosenburg and Moore eds., (Springer-Verlag, New York, 1994), pp. 269-315.

As used herein, the term "antigen-binding protein" refers to proteins that bind to a specific antigen. "Antigen-binding proteins" include, but are not limited to, immunoglobulins, including polyclonal, monoclonal, chimeric, and humanized antibodies; Fab fragments, F(ab')2 fragments, and Fab expression libraries; and single chain antibodies.

The term "epitope" as used herein refers to that portion of an antigen that makes contact with a particular immunoglobulin.

The terms "specific binding" or "specifically binding" when used in reference to the interaction of an antibody (or a portion thereof (e.g., scFv) and a protein or peptide means that the interaction is dependent upon the presence of a particular structure (e.g., the antigenic determinant or epitope) on the protein; in other words the antibody (or a portion thereof (e.g., scFv) is recognizing and binding to a specific protein structure rather than to proteins in general. For example, if an antibody is specific for epitope "A," the presence of a protein containing epitope A (or free, unlabeled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors for developing cancer. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the type and/or stage of cancer is not known. The term further includes people who previously had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, etc.

As used herein, the term "post-surgical tumor tissue" refers to cancerous tissue (e.g., organ tissue) that has been removed from a subject (e.g., during surgery).

As used herein, the term "subject at risk for cancer" refers to a subject with one or more risk factors for developing a specific cancer. Risk factors include, but are not limited to, gender, age, genetic predisposition, environmental exposure, and previous incidents of cancer, preexisting non-cancer diseases, and lifestyle.

As used herein, the term "characterizing cancer in a subject" refers to the identification of one or more properties of a cancer sample in a subject, including but not limited to, the presence of benign, pre-cancerous or cancerous tissue and the stage of the cancer.

As used herein, the term "characterizing tissue in a subject" refers to the identification of one or more properties of a tissue sample (e.g., including but not limited to, the presence of cancerous tissue, the presence of pre-cancerous tissue that is likely to become cancerous, and the presence of cancerous tissue that is likely to metastasize).

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "primary tumor cell" refers to a cancer cell that is isolated from a tumor in a mammal and has not been extensively cultured in vitro.

As used herein, the terms "treatment", "therapeutic use", or "medicinal use" refer to any and all uses of compositions and methods of the invention that remedy a disease state or symptoms, or otherwise prevent, hinder, retard, or reverse the progression of disease or other undesirable symptoms in any way whatsoever. For example, the terms "treatment of cancer" or "treatment of tumor" or grammatical equivalents herein are meant the suppression, regression, or partial or complete disappearance of a pre-existing cancer or tumor. The definition is meant to include any diminution in the size, aggressiveness, or growth rate of a pre-existing cancer or tumor.

As used herein, the terms "improved therapeutic outcome" and "enhanced therapeutic efficacy," relative to cancer refers to a slowing or diminution of the growth of cancer cells or a solid tumor, or a reduction in the total number of cancer cells or total tumor burden. An "improved therapeutic outcome" or "enhanced therapeutic efficacy" means there is an improvement in the condition of the individual according to any clinically acceptable criteria, including reversal of an established tumor, an increase in life expectancy or an improvement in quality of life.

As used herein, the term "gene transfer system" refers to any means of delivering a composition comprising a nucleic acid sequence to a cell or tissue. For example, gene transfer systems include, but are not limited to, vectors (e.g., retroviral, adenoviral, lentiviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. Non-limiting examples of viral gene transfer systems useful in the compositions and methods of the invention are lentiviral- and retroviral-gene transfer systems.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)-uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2 thiocytosine, 5-methyl-2 thiouracil, 2-thiouracil, 4-thiouracil, 5-methyluracil, N-uracil oxyacetic acid methylester, and 2,6-diaminopurine.

The term "gene" refers to a nucleic acid (e.g., DNA) sequence that comprises coding sequences necessary for the production of a polypeptide, precursor, or RNA (e.g., mRNA, rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length gene product or fragment thereof are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA specifies the sequence or order of amino acids in a nascent polypeptide during translation (e.g., protein synthesis).

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc.). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated poly-nucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neigh-boring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucle-otide is to be utilized to express a protein, the oligonucle-otide or polynucleotide will contain at a minimum the sense or coding strand (i.e., the oligonucleotide or polynucleotide may be single-stranded), but may contain both the sense and anti-sense strands (i.e., the oligonucleotide or polynucle-otide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immuno-globulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Lentiviral vectors or retroviral vectors may be used (e.g., to introduce DNA encoding CAR constructs into cells (e.g., T cells)). Other vectors (e.g., non-episomal mammalian vec-tors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector. Non-limiting examples of vectors useful in the compositions and methods of the invention include lentiviral and retroviral vectors. Lentiviral vectors include, but are not limited to, human, simian, and feline immunodeficiency virus (HIV, SIV, and FIV, respectively) vectors.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA. The term "transient transfection" or "transiently transfected" refers to the introduction of foreign DNA into a cell where the foreign DNA fails to integrate into the genome of the transfected cell. The foreign DNA persists in the nucleus of the transfected cell (e.g., for several days). During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient; in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside-3'-phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk-negative (tk⁻) cell lines, the CAD gene that is used in conjunction with CAD-deficient cells and the mammalian hypoxanthine-guanine phosphoribosyl transferase (hprt) gene that is used in conjunction with hprt-negative (hprr) cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present invention.

DETAILED DESCRIPTION OF EMBODIMENTS

Histone H3 is one of the five main histone proteins involved in the structure of chromatin in eukaryotic cells. Featuring a main globular domain and a long N-terminal tail, H3 is involved with the structure of the nucleosomes of the "beads on a string" structure. The N-terminal tail of histone H3 protrudes from the globular nucleosome core and can undergo several different types of epigenetic modifications that influence cellular processes. These modifications include the covalent attachment of methyl or acetyl groups to lysine and arginine amino acids and the phosphorylation of serine or threonine. Histone variant H3.3 is typically enriched in active chromatin.

Tumors with histone H3 K27M (H3K27M) mutations are highly lethal. They predominantly occur in children and present as midline brain tumors or spinal tumors. Despite dozens of clinical trials over the last 30 years, standard therapy is limited to radiation therapy and the vast majority of patients die of their disease within 18 months of diagnosis. Thus, currently available treatments for H3K27M tumors are unsatisfactory. Except for radiation therapy, no other antineoplastic therapy has demonstrated benefit in these diseases.

For example, diffuse intrinsic pontine glioma (DIPG) and other histone H3 K27M (H3K27M) mutated midline gliomas are extremely aggressive and universally fatal. While much progress has been achieved characterizing the molecular origins of these tumors, improvements in clinical management have remained elusive, with median survival for DIPG remaining approximately 10 months. Immunotherapy agents including checkpoint inhibitors have produced substantial benefit in numerous adult cancers refractory to traditional therapies, but these agents have not yet demonstrated conclusive benefit in sporadic childhood cancers, likely due to the paucity of non-synonymous somatic mutations in these diseases (see, e.g., Majzner et al., Cancer Cell, 2017. 31(4): p. 476-485. Adoptive cell transfer of chimeric antigen receptor-expressing (CAR-expressing) T cells has demonstrated activity in B cell malignancies and central nervous system (CNS) malignancies.

Historically, pediatric diffuse gliomas were grouped with their adult counterparts, despite known differences in behavior between pediatric and adult gliomas with similar histological appearances. Information on the distinct underlying genetic abnormalities in pediatric diffuse gliomas is beginning to allow the separation of some entities from histologically similar adult counterparts. One narrowly defined group of tumors primarily occurring in children is characterized by K27M mutations in the histone H3 gene H3F3A, or less commonly in the related HIST1H3B gene, a diffuse growth pattern, and a midline location (e.g., thalamus, brain stem, and spinal cord). This newly defined entity is termed diffuse midline glioma, H3K27M-mutant and includes tumors previously referred to as diffuse intrinsic pontine glioma (DIPG).

GD2 is a disialoganglioside highly expressed in several pediatric and adult cancers, including neuroblastoma. GD2 is widely expressed during fetal development but among normal post-natal tissues its expression is limited to low levels of expression on osteoprogenitors, brain, peripheral nerves and skin melanocytes. Because of its high surface expression on tumor cells and low expression on normal tissues, GD2 has been a target for the development of immunotherapeutic monoclonal antibodies. Starting from these encouraging clinical results, anti-GD2 antibody therapy is included in many frontline protocols for neuroblastoma. GD2-based monoclonal antibody (mAb) therapies are unlikely to benefit patients with H3K27M tumors because mAbs do not efficiently traffic into the CNS.

Experiments were conducted during development of embodiments of the invention in an effort to identify new targets and strategies for immunotherapy in DIPG and other histone H3 K27M (H3K27M) mutated cancers (e.g., midline gliomas). Cell surface antigens in patient-derived DIPG cultures were screened for potential immunotherapeutic targets (see, e.g., Examples 1 and 2). Significant overlap between independent patient-derived cultures identified a core group of surface markers conserved across DIPG patients (see, e.g., Example 2 and FIGS. 1A and 1B). From these common targets, the disialoganglioside GD2 was identified as commonly expressed at significantly higher levels on each of the patient-derived DIPG cultures screened. Additional experiments identified that significant and remarkably high levels of GD2 expression occurred in all H3K27M gliomas examined, as well as those with the less common HIST1H3B K27M mutant, whereas pediatric high grade gliomas (pHGG) harboring wild type histone H3 displayed significantly lower GD2 expression (see, e.g., Examples 1 and 2 and FIG. 1C).

Further experiments were performed in an effort to determine whether transcriptional perturbations resulting from the H3K27M mutation might be linked to increased GD2 expression. Expression of ganglioside synthesis enzymes in a panel of patient-derived DIPG and pHGG cultures identified consistently higher expression of upstream ganglioside synthesis enzymes in cultures bearing the H3K27M mutation (see, e.g., Example 2 and FIG. 1J). Thus, in one embodiment, the invention provides that GD2 overexpression results from upregulation of ganglioside synthesis pathway component genes in H3K27M mutant tumor relative to H3 WT pHGGs.

Figure 1B:
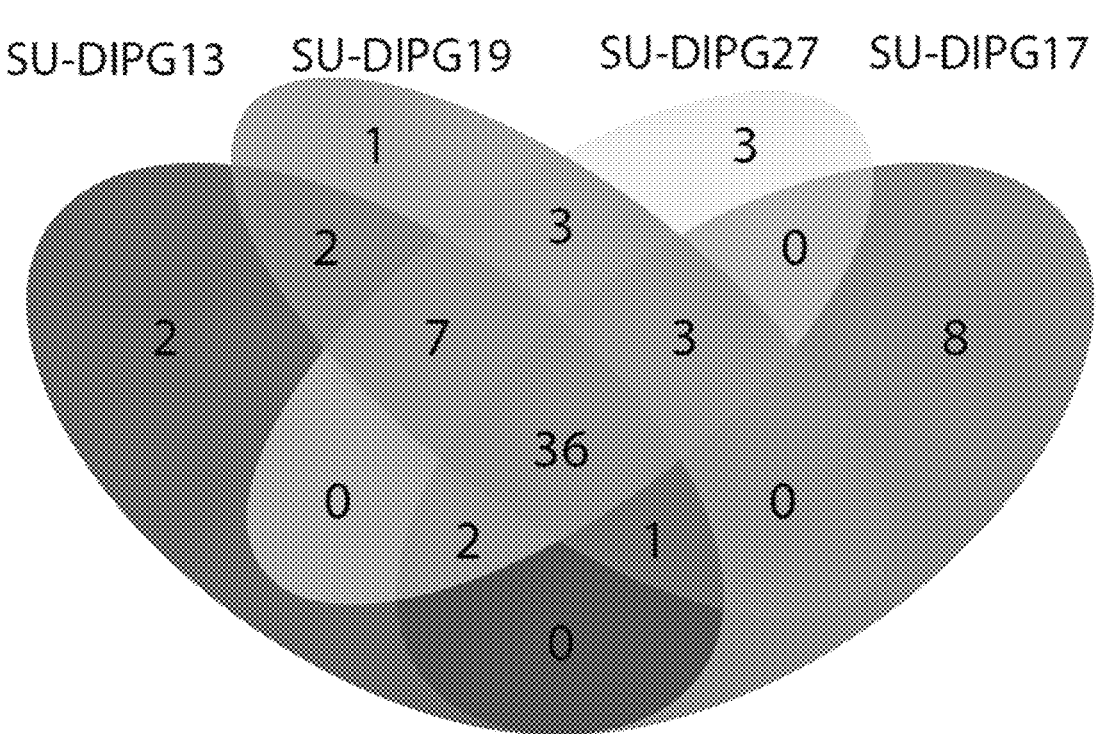
Figure 1C:
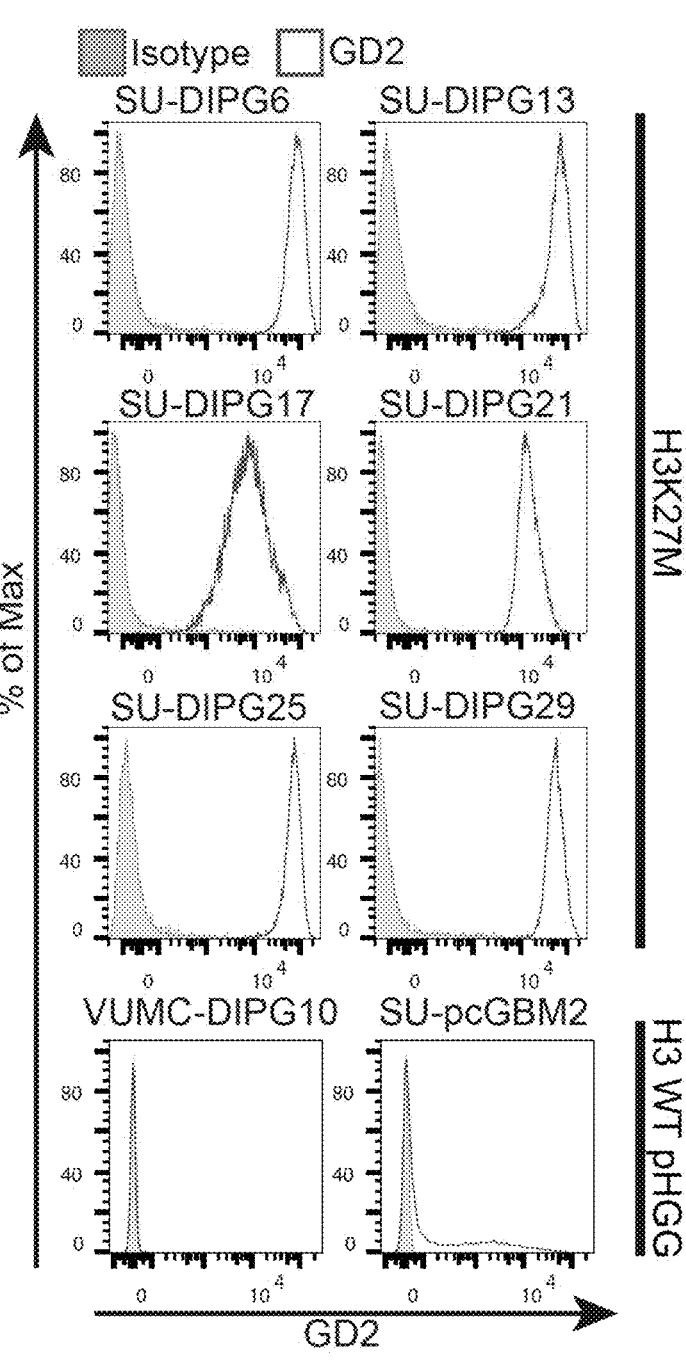
Figure 1D:
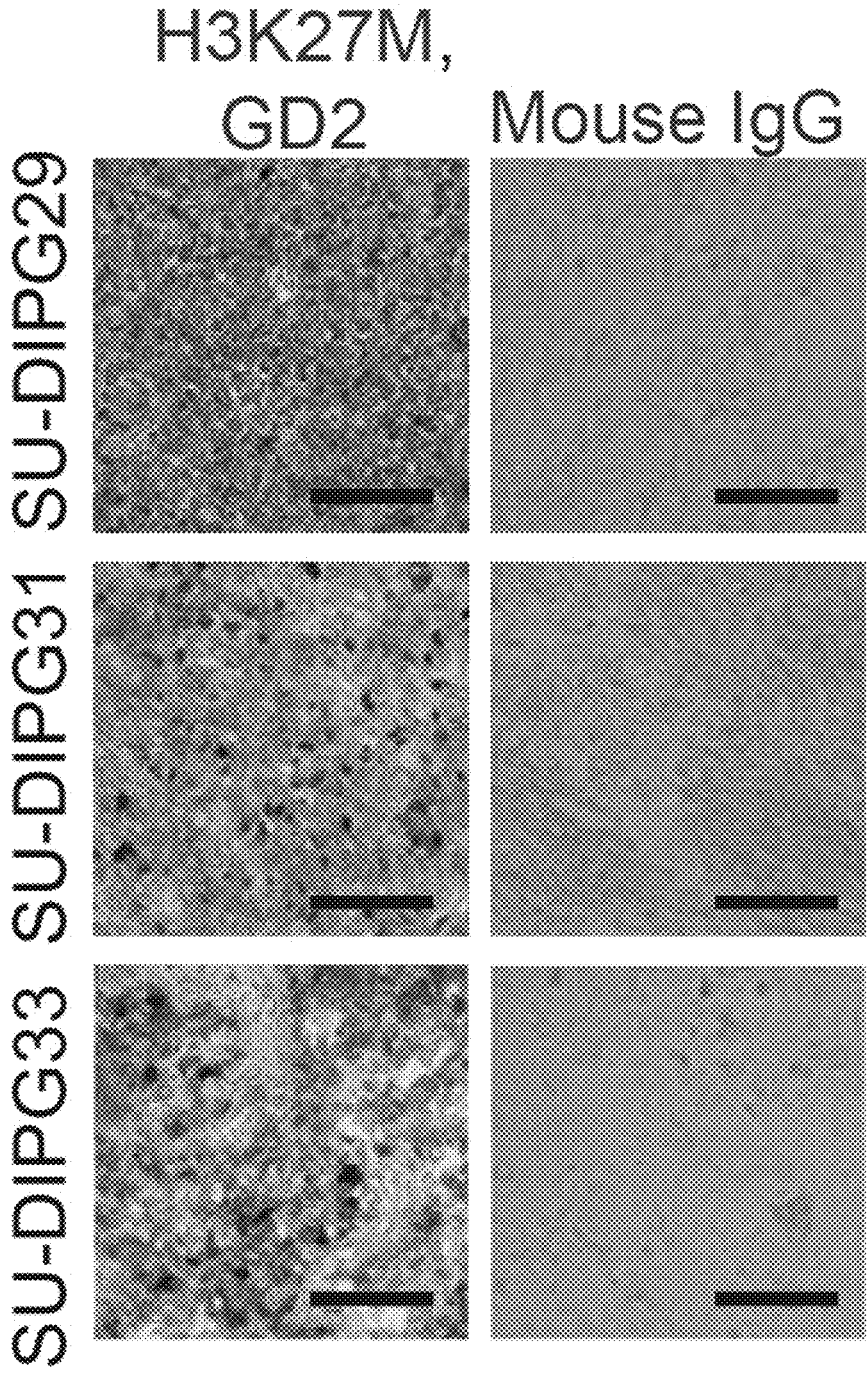

Additionally, double immunostaining of primary human DIPG tissue for H3K27M to identify infiltrating malignant cells and GD2 identified local expression of GD2 in the native tumor context (see, e.g., Example 2 and FIG. 1D).

Accordingly, in one embodiment, the invention provides the identification of a heretofore unknown target for therapeutic intervention of H3K27M tumors (e.g., GD2).

GD2-targeting immunotherapies are currently under clinical and preclinical investigation in several diseases, including neuroblastoma, osteosarcoma, and melanoma (see, e.g., Thomas et al., PLoS One, 2016. 11(3): p. e0152196; Long et al., Nature Medicine, 2015. 21(6): p. 581-590; Long et al., Cancer Immunology Research, 2016. 4(10): p. 869-880; Yu et al., N Engl J Med, 2010. 363(14): p. 1324-34; Perez Horta et al., Immunotherapy, 2016. 8(9): p. 1097-117; Heczey et al, Molecular Therapy). Unlike mAbs which do not efficiently cross the blood-brain barrier, activated CAR T cells efficiently infiltrate the CNS following adoptive transfer.

Further experiments were conducted during development of embodiments of the invention in an effort to assess and characterize the ability GD2-targeted, engineered immune cells as a potential therapeutic intervention for H3K27M tumors (see, e.g., Examples 3-5). Human GD2-targeting chimeric antigen receptor (CAR) T cells were generated and tested. GD2-dependent cell killing and cytokine secretion was observed upon exposure to patient-derived DIPG cultures relative to Mock or CD19-directed CAR T cells (see, e.g., Example 3). Moreover, potent antitumor efficacy was observed using GD2-directed CAR T cells delivered by adoptive cell transfer in patient-derived DIPG orthotopic xenografts (see, e.g., Example 4).

CAR T-cell therapy effectively cleared multiple types of midline H3K27M mutant pediatric diffuse midline gliomas (see, e.g., Example 5). Clearance of the gliomas was associated with toxicity in thalamic xenografts.

In one aspect, the invention provides novel methods for the treatment of H3K27M-positive (H3K27M+) cancers/tumors using modified immune cells engineered to express a CAR targeting GD2. In various aspects of the invention, methods of treating a H3K27M cancer/tumors are provided, the methods comprising administering to a patient having such a cancer or tumor an effective amount of immune cells engineered to express a CAR targeting GD2. In certain embodiments, the H3K27M cancer is DIPG. In another embodiment, the H3K27M cancer is diffuse midline glioma.

In certain embodiments, the presence of significantly elevated levels of GD2 present on the surface of H3K27M cancers/tumors results in efficacious treatment (e.g., killing and/or inhibition of progression) of H3K27M cancers/tumors with GD2-directed CAR T cells. For example, the efficacy of the GD2 CAR in H3K27M cancers/tumors appeared to be driven largely by the homogeneously high expression of the target antigen in H3K27M mutant DIPG (See FIG. 1C), which was consistently higher than that present on GD2+ neuroblastoma and sarcoma cell lines. Although an understanding of a mechanism is not needed to practice the present invention and while the present invention is not limited to any particular mechanism, homogeneously high expression of the target GD2 antigen on H3K27M cancers/tumors is related to the efficacy of treatment of H3K27M cancer/tumors with GD2-specific CAR T cells.

In certain embodiments, the invention provides methods of treating (e.g., inhibiting growth of and/or killing) H3K27M tumors using immune cells (e.g., T cells (e.g., CD3+ T cells)) genetically engineered to express a receptor that recognizes GD2 (e.g., on the surface of the H3K27M gliomas) and transmit a signal that activates the immune cell to induce expansion of the immune cell and/or tumor killing. A non-limiting example of a receptor is a chimeric antigen receptor (CAR) that incorporates an scFv derived from a mAb that recognizes GD2, as well as a transmembrane domain, and one or more intracellular signaling domains. The CAR may be further engineered to incorporate other signaling elements that facilitate expansion of the engineered cells following encounter with the GD2 antigen as well elements that enable long-term persistence of the engineered cells. The invention further provides compositions comprising the genetically engineered cells (e.g., immunotherapeutic compositions produced and administered in sufficient quantity to reach the H3K27M tumors in the central nervous system).

Compositions and methods described herein find use in treating any cancer/tumor harboring a somatic mutation of the histone H3 (H3) gene H3F3A at lysine 27 (e.g., Lys27Met or K27M (H3K27M)). Examples of cancers harboring H3K27M mutations that may be treated with the compositions and methods of the present invention include, but are not limited to, diffuse intrinsic pontine glioma (DIPG) and/or diffuse midline glioma.

GD2 Specific Chimeric Antigen Receptor (CAR) Construction and Expression.

Chimeric antigen receptors (CARs) are recombinant receptor constructs comprising an extracellular antigen-binding domain (e.g., a single-chain variable fragment (scFv) derived from an antibody) joined to a hinge/spacer peptide, a transmembrane domain, and further linked to an intracellular signaling domain (e.g., an intracellular T cell signaling domain of a T cell receptor). Immune cells (e.g., T cells) genetically modified to express CARs display the specificity of an antibody (e.g., they are not MHC/HLA-restricted) with the functionality of effector cells (e.g., cytotoxic and/or memory functions of T cells).

The invention is not limited by the chimeric antigen receptor (CAR) specific for GD2 expressed in immune cells (e.g., the CAR construct used in methods of the invention). In one embodiment, the CAR comprises a fusion protein of the variable regions of the heavy (VH) and light chains (VL) (e.g., a single chain variable fragment (scFv)) of an immunoglobulin that binds with specificity to GD2. In a further embodiment, the immunoglobulin binds with specificity to the GD2 epitope GalNAcβ1-4(NeuAcα2-8NeuAcα2-3)Gal. Those of ordinary skill in the art know that scFv is a fusion protein of the variable regions of the heavy (VH) and light chains (VL) of immunoglobulins, connected with a linker peptide (e.g., of about 10 to about 25 amino acids). The invention is not limited by the type of linker. In some embodiments, the linker is rich in glycine (e.g., for flexibility). In some embodiments, the linker comprises serine and/or threonine (e.g., for solubility). In some embodiments, the linker comprises a portion rich in glycine and a portion comprising serine and/or threonine.

Any antibody/immunoglobulin that binds with specificity to GD2 may be used to construct a CAR (e.g., using VH and VL regions to construct a fusion protein, scFv) for expression in immune cells (e.g., used in therapeutic methods of the invention). Examples of such antibodies/immunoglobulins include, but are not limited to, 14G2a, ch14.18, hu14.18K322A, m3F8, hu3F8-IgG1, hu3F8-IgG4, HM3F8, UNITUXIN, DMAb-20 or any other antibody that binds with specificity to GD2 (e.g., known or described in the art, or yet to be identified). In one embodiment, the CAR comprises a 14g2a scFv. A GD2 CAR may comprise a receptor incorporating variants within scFv of an anti-GD2 antibody (e.g., 14g2a scFv) generated to enhance affinity and/or diminish tonic signaling. The GD2 CAR may incorporate variable lengths of the hinge regions (e.g., between the scFv and the signaling domains) and/or varying transmembrane domains. The invention is not limited by the transmembrane domain used. Indeed, any transmembrane domain may be used including, but not limited to, all or part of the transmembrane domain of CD3-zeta chain (CD3ζ), CD28, OX40/CD134, 4-1BB/CD137/TNFRSF9, FcεRIγ, ICOS/CD278, ILRB/CD122, IL-2RG/CD132, or CD40.

A CAR construct of the invention may include an intracellular signaling domain (e.g., CD3 zeta of a native T cell receptor complex and/or other signaling domain (e.g., a MyD88 signaling domain)) that transduces the event of ligand binding to an intracellular signal (e.g., that activates (e.g., partially) the immune cell (e.g., T lymphocyte)). Absent co-stimulatory signals, receptor-ligand biding is often insufficient for full activation and proliferation of the immune cell (e.g., T cell). Thus, a CAR construct may include one or more co-stimulatory domains (e.g., that provide a second signal to stimulate full immune cell (e.g., T cell) activation). In one embodiment, a co-stimulatory domain is used that increases CAR immune T cell cytokine production. In another embodiment, a co-stimulatory domain is used that facilitates immune cell (e.g., T cell) replication. In still another embodiment, a co-stimulatory domain is used that prevents CAR immune cell (e.g., T cell) exhaustion. In another embodiment, a co-stimulatory domain is used that increases immune cell (e.g., T cell) antitumor activity. In still a further embodiment, a co-stimulatory domain is used that enhances survival of CAR immune cells (e.g., T cells) (e.g., post-infusion into patients). Exemplary co-stimulatory domains include, but are not limited to, all or part of (e.g., the endodomain portion of) the co-stimulatory molecules of B7-1/CD80; CD28; B7-2/CD86; CTLA-4; B7-H1/PD-L1; ICOS/CD278; ILRB/CD122; IL-2RG/CD132; B7-H2; PD-1; B7-H3; PD-L2; B7-H4; PDCD6; BTLA; 4-1BB/TNFRSF9/CD137; FcεRIγ; CD40 Ligand/TNFSF5; 4-1BB Ligand/TNFSF9; GITR/TN-FRSF18; BAFF/BLyS/TNFSF13B; GITR Ligand/TNFSF18; BAFF R/TNFRSF13C; HVEM/TNFRSF14; CD27/TNFRSF7; LIGHT/TNFSF14; CD27 Ligand/TNFSF7; OX40/TNFRSF4; CD30/TNFRSF8; OX40 Ligand/TNFSF4; CD30 Ligand/TNFSF8; TAC1/TNFRSF13B; CD40/TNFRSF5; 2B4/CD244/SLAMF4; CD84/SLAMF5; BLAME/SLAMF8; CD229/SLAMF3; CD2 CRACC/SLAMF7; CD2F-10/SLAMF9; NTB-A/SLAMF6; CD48/SLAMF2; SLAM/CD150; CD58/LFA-3; CD2; Ikaros; CD53; Integrin alpha 4/CD49d; CD82/Kai-1; Integrin alpha 4 beta 1; CD90/Thy1; Integrin alpha 4 beta 7/LPAM-1; CD96; LAG-3; CD160; LMIR1/CD300A; CRTAM; TCL1A; DAP12; TIM-1/KIM-1/HAVCR; Dectin-1/CLEC7A; TIM-4; DPPIV/CD26; TSLP; EphB6; TSLP R; and HLA-DR. In one embodiment, a CAR construct expressed in immune cells used in methods of the invention includes a CD28 endodomain, a 4-1BB endodomain, and/or an OX40 endodomain. In certain embodiments, a CAR construct specific for GD2 of the invention comprises an scFv of an antibody that binds with specificity to GD2 (e.g., 14g2a), a transmembrane domain (e.g., of CD8), T cell receptor intracellular signaling domain (e.g., CD3 zeta) and at least one co-stimulatory domain (e.g., 4-1BB).

The invention is not limited by the type of immune cells genetically modified to express GD2-specific CARs. Exemplary immune cells include, but are not limited to, T cells, NK cells, effector cells such as gamma delta T cells, memory T cells, macrophages, and cytokine induced killer cells. In one embodiment, the immune cells are CD4+ and/or CD 8+ T cells (e.g., that are CD3+).

The invention is not limited by the means of genetically expressing CARs in immune cells. Indeed, any means known in the art and/or described herein may be used. Non-limiting examples of methods of genetically engineering immune cells include, but are not limited to, retrovirus- or lentivirus-mediated transduction, transduction with transposase-based systems for gene integration, CRISPR/Cas9-mediated gene integration, non-integrating vectors such as RNA or adeno-associated viruses, or other methods described herein. The engineered immune cells product may incorporate unselected T cells or other immune cells, or T cell subsets selected for greater expansion or persistence capacity. In order to diminish toxicity, incorporation of elements that allow killing of cells engineered to express the GD2 targeted signaling molecule may be incorporated. In order to diminish toxicity and/or enhance efficacy, incorporation of elements that allow regulation of protein expression in engineered cells may be included.

Therapeutic Methods, Compositions, and Combination Therapy.

In certain embodiments, the invention also provides methods for treating or delaying the progression of cancer in an individual comprising administering to the individual an effective amount of immune cells genetically modified to express GD2-specific CARs (e.g., GD2 CAR T cells). In some embodiments, the treatment results in a sustained response in the individual after cessation of the treatment. The methods described herein may find use in treating conditions where enhanced immunogenicity is desired such as increasing tumor immunogenicity for the treatment of cancer. Also provided herein are methods of enhancing immune function in an individual having cancer comprising administering to the individual an effective amount of immune cells genetically modified to express GD2-specific CARs (e.g., GD2 CAR T cells). Any immune cell (e.g., any T cell (e.g., a CD3+ T cell)) genetically modified to express a GD2-specific CAR known in the art or described herein may be used in these methods. In some embodiments, the individual is a human.

In some embodiments, the individual has cancer that is resistant (e.g., has been demonstrated to be resistant) to one or more other forms of anti-cancer treatment (e.g., chemotherapy, immunotherapy, etc.). In some embodiments, resistance includes recurrence of cancer or refractory cancer. Recurrence may refer to the reappearance of cancer, in the original site or a new site, after treatment. In some embodiments, resistance includes progression of the cancer during treatment with chemotherapy. In some embodiments, resistance includes cancer that does not respond to traditional or conventional treatment with a chemotherapeutic agent. The cancer may be resistant at the beginning of treatment or it may become resistant during treatment. In some embodiments, the cancer is at early stage or at late stage.

In certain embodiments, the invention provides that exposure of animals (e.g., humans) suffering from cancers/tumors characterized by H3K27M-expressing cells (e.g., DIPG characterized by H3K27M-expressing cells) to therapeutically effective amounts of immunotherapeutic compositions comprising immune cells genetically modified to express GD2-specific CARs (e.g., that target and kill GD2 expressing tumors) inhibits the growth of such H3K27M-expressing cancer cells outright and/or renders such cells as a population more susceptible to cancer therapeutic drugs or radiation therapies (e.g., to the cell death-inducing activity thereof). The immunotherapeutic compositions and methods of the invention can be used for the treatment, amelioration, or prevention of disorders, such as any type of cancer characterized by H3K27M-expressing cells (e.g., DIPG characterized by H3K27M-expressing cells).

In certain embodiments, immunotherapeutic compositions comprising immune cells genetically modified to express GD2-specific CARs are used to treat, ameliorate, or prevent a cancer characterized by H3K27M-expressing cells (e.g., DIPG characterized by H3K27M-expressing cells) that additionally is characterized by resistance to one or more conventional cancer therapies (e.g., those cancer cells which are chemoresistant, radiation resistant, hormone resistant, and the like). In certain embodiments, the cancer is DIPG. In other embodiments, the cancer is a diffuse midline glioma. As described herein, any immune cell genetically modified to express a GD2-specific CAR may be used in the immunotherapeutic compositions and methods of the invention.

Immunotherapeutic compositions (e.g., comprising immune cells genetically modified to express GD2-specific CARs) and methods of the invention may be used to induce cytotoxic activities against tumor cells and/or to promote cell survival and function (e.g., survival and function of the modified immune cells). For example, immunotherapeutic compositions and methods of the invention can be used to induce interleukin-2 (IL-2) to promote T cell survival; to induce Fas Ligand (FasL) and/or tumor necrosis factor-related apoptosis inducing ligand (TRAIL) (e.g., to induce tumor cell apoptosis); and/or to induce interferon (IFN)-gamma (e.g., to activate the innate immune response (e.g., against cancer)). In some embodiments, compositions and methods of the invention are used to induce cell cycle arrest and/or apoptosis and also to potentiate the induction of cell cycle arrest and/or apoptosis either alone or in response to additional apoptosis induction signals. In some embodiments, immune cells genetically modified to express GD2-specific CARs sensitize H3K27M-expressing cancer cells to induction of cell cycle arrest and/or apoptosis, including cells that are normally resistant to such inducing stimuli. In other embodiments, immune cells genetically modified to express GD2-specific CARs are used to induce apoptosis in any disorder characterized by the presence of H3K27M-expressing cancer cells (e.g., DIPG and/or diffuse midline glioma characterized by the presence of H3K27M cancer cells) that can be treated, ameliorated, or prevented by the induction of apoptosis.

In some embodiments, the compositions and methods of the present invention are used to treat diseased cells, tissues, organs, or pathological conditions and/or disease states in an animal (e.g., a mammalian patient including, but not limited to, humans and companion animals). In this regard, various diseases and pathologies characterized by the presence of H3K27M cells are amenable to treatment or prophylaxis using the present methods and compositions. In some embodiments, cancer cells being treated are metastatic. In other embodiments, the cancer cells being treated are resistant to anticancer agents. In other embodiments, the disorder is any disorder having cells characterized by the presence of the H3K27M mutation.

Some embodiments of the present invention provide methods for administering an effective amount of immune cells genetically modified to express GD2-specific CARs and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is an anticancer agent. For example, although significant tumor clearance was achieved using the immunotherapeutic compositions and methods of the invention, persistence of small numbers of tumor cells negative for GD2 expression (e.g., by immunofluorescence staining) indicated that in addition to the immunotherapeutic T cell compositions of the invention, in some embodiments, multimodal or combination therapy using any one or more cancer treatments described herein may be useful together with immunotherapeutic T cell compositions of the invention in order to reduce and/or avoid antigen escape (see, for example, FIG. 4).

A number of suitable anticancer agents are contemplated for use in, or in combination with, the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC®)); antisense molecules; antibodies (e.g., HERCEPTIN®, RITUXAN®, ZEVALIN®, and AVASTIN®); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON®, DELTASONE®, dexamethasone, dexamethasone intensol, DEXONE, HEXADROL®, hydroxychloroquine, METICORTEN®, ORADEXON®, ORASONE, oxyphenbutazone, PEDIAPRED®, phenylbutazone, PLAQUENIL®, prednisolone, prednisone, PRELONE®, and TANDEARIL); and cancer chemotherapeutic drugs (e.g., irinotecan (CAMPTOSAR®), CPT-11, fludarabine (FLUDARA®), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE® or TAXOL®); cellular signaling molecules; ceramides and cytokines; staurosporine, and the like.

In still other embodiments, the compositions and methods of the present invention are used together with at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VBL), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context may also be used in the compositions and methods of the present invention. For example, the U.S. Food and Drug Administration maintains a formulary of oncolytic agents approved for use in the United States. International counterpart agencies to the U.S. F.D.A. maintain similar formularies.

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724, 714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering compositions and methods of the invention with (e.g., before, during, or after) radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy, (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, immune cells (e.g., T cells (e.g., CD8 and/or CD4 T cells)) genetically modified to express GD2-specific CARs and one or more therapeutic agents or anticancer agents are administered to an animal under one or more of the following conditions: at different periodicities, at different durations, at different concentrations, by different administration routes, etc. In some embodiments, immune cells (e.g., T cells (e.g., CD8 and/or CD4 T cells)) genetically modified to express GD2-specific CARs are administered prior to the therapeutic or anticancer agent, e.g., 0.5, 1, 2, 3, 4, 5, 10, 12, 18 hours or more, 1, 2, 3, 4, 5, 6 or more days, or 1, 2, 3, 4, 5, 6 or more weeks prior to the administration of the therapeutic or anticancer agent. In some embodiments, immune cells (e.g., T cells (e.g., CD8 and/or CD4 T cells)) genetically modified to express GD2-specific CARs are administered after the therapeutic or anticancer agent, e.g., 0.5, 1, 2, 3, 4, 5, 10, 12, 18 or more hours, 1, 2, 3, 4, 5, 6 or more days, or 1, 2, 3, 4, 5, 6, or more weeks after the administration of the anticancer agent. In some embodiments, immune cells (e.g., T cells (e.g., CD8 and/or CD4 T cells)) genetically modified to express GD2-specific CARs and the therapeutic or anticancer agent are administered concurrently but on different schedules, e.g., modified immune cells are administered daily while the therapeutic or anticancer agent is administered once a week, once every two weeks, once every three weeks, once every four weeks, or more. In other embodiments, modified immune cells are administered once a week while the therapeutic or anticancer agent is administered daily, once a week, once every two weeks, once every three weeks, once every four weeks, or more.

Compositions within the scope of this invention include all compositions wherein the immune cells (e.g., T cells (e.g., CD8 and/or CD4 T cells)) genetically modified to express GD2-specific CARs are contained in an amount which is effective to achieve its intended purpose. While individual needs vary, determination of optimal ranges of effective amounts of each component is within the skill of the art. In one non-limiting example, immune cells (e.g., T cells (e.g., CD8 and/or CD4 T cells)) genetically modified to express GD2-specific CARs may be administered to mammals, e.g. humans, in order to provide the human between 1000 and $10^{10}$ modified immune cells per day (e.g., for treating cancer). In another embodiment, between 1000 and $10^{10}$ modified immune cells are administered to treat, ameliorate, or prevent cancer (e.g., prevent metastasis, recurrence, and/or progression of cancer). The unit dose may be administered in one or more administrations one or more times daily (e.g., for 1, 2, 3, 4, 5, 6, or more days or weeks).

Modified immune cells may be administered as part of a pharmaceutical preparation containing suitable pharmaceutically acceptable carriers comprising excipients and auxiliaries which facilitate processing and/or administration of the modified cells into preparations which can be used pharmaceutically. Modified immune cells and/or pharmaceutical preparations containing the same, or other treatments used in concurrently therewith, may be administered intravenously, intramuscularly, subcutaneously, intratumorally, intraperitoneally, intrathecally, or intraventricularly. An effective amount of modified immune cells and/or pharmaceutical preparations containing the same may be administered for prevention or treatment of disease. The appropriate dosage may be determined based on the type of disease to be treated, the type of modified immune cell, the severity and course of the disease, the clinical condition of the individual, the individual's clinical history and response to the treatment, and the discretion of the attending physician.

The efficacy of any of the methods described herein (e.g., treatment with immune cells engineered to express a CAR targeting GD2 alone in in combination with one or more chemotherapeutic agents described herein) may be tested in various models known in the art, such as clinical or preclinical models. Suitable pre-clinical models are exemplified herein. Other models of H3K27M mutant cancers/tumors may be used. For any exemplary model, after developing tumors, mice are randomly recruited into treatment groups receiving treatment or control treatment. Tumor size (e.g., tumor volume) is measured during the course of treatment, and overall survival rate is also monitored.

In some embodiments, a sample is obtained prior to treatment with immune cells engineered to express a CAR targeting GD2 (e.g., alone or in combination with another therapy described herein). In some embodiments, the sample is a tissue sample (e.g., formalin-fixed and paraffin-embedded (FFPE), archival, fresh or frozen). In some embodiments, the sample is whole blood. In some embodiments, the whole blood comprises immune cells, circulating tumor cells and any combinations thereof.

In some embodiments, presence of the H3K27M mutation is evaluated in a tumor or tumor sample. As used herein, a tumor or tumor sample may encompass part or all of the tumor area occupied by tumor cells. In some embodiments, a tumor or tumor sample may further encompass tumor area occupied by tumor associated intratumoral cells and/or tumor associated stroma (e.g., contiguous peri-tumoral desmoplastic stroma). Tumor-associated intratumoral cells and/or tumor associated stroma may include areas of immune infiltrates immediately adjacent to and/or contiguous with the main tumor mass.

Presence and/or expression levels/amount of a biomarker (e.g., H3K27M) can be determined qualitatively and/or quantitatively based on any suitable criterion known in the art, including but not limited to DNA, mRNA, cDNA, proteins, protein fragments and/or gene copy number. In certain embodiments, presence and/or expression levels/amount of a biomarker in a first sample is increased or elevated as compared to presence/absence and/or expression levels/amount in a second sample. In certain embodiments, presence/absence and/or expression levels/amount of a biomarker in a first sample is decreased or reduced as compared to presence and/or expression levels/amount in a second sample. In certain embodiments, the second sample is a reference sample, reference cell, reference tissue, control sample, control cell, or control tissue. Additional disclosures for determining presence/absence and/or expression levels/amount of a gene are described herein.

Presence and/or expression level/amount of various biomarkers in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (as for example serum ELISA), biochemical enzymatic activity assays, in situ hybridization, Southern analysis, Northern analysis, whole genome sequencing, polymerase chain reaction ("PCR") including quantitative real time PCR ("qRT-PCR") and other amplification type detection methods, such as, for example, branched DNA, SISBA, TMA and the like), RNA-Seq, FISH, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

In alternative methods, the sample may be contacted with an antibody specific for biomarker under conditions sufficient for an antibody-biomarker complex to form, and then detecting said complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

Presence and/or expression level/amount of a selected biomarker in a tissue or cell sample may also be examined by way of functional or activity-based assays. For instance, if the biomarker is an enzyme, one may conduct assays known in the art to determine or detect the presence of the given enzymatic activity in the tissue or cell sample.

In certain embodiments, the samples are normalized for both differences in the amount of the biomarker assayed and variability in the quality of the samples used, and variability between assay runs. Such normalization may be accomplished by detecting and incorporating the expression of certain normalizing biomarkers, including well known housekeeping genes. Alternatively, normalization can be based on the mean or median signal of all of the assayed genes or a large subset thereof (global normalization approach). On a gene-by-gene basis, measured normalized amount of a subject tumor mRNA or protein is compared to the amount found in a reference set. Normalized expression levels for each mRNA or protein per tested tumor per subject can be expressed as a percentage of the expression level measured in the reference set. The presence and/or expression level/amount measured in a particular subject sample to be analyzed will fall at some percentile within this range, which can be determined by methods well known in the art.

In one embodiment, the sample is a clinical sample. In another embodiment, the sample is used in a diagnostic assay. In some embodiments, the sample is obtained from a primary or metastatic tumor. Tissue biopsy is often used to obtain a representative piece of tumor tissue. Alternatively, tumor cells can be obtained indirectly in the form of tissues or fluids that are known or thought to contain the tumor cells of interest. Genes or gene products can be detected from cancer or tumor tissue or from other body samples such as urine, sputum, serum or plasma. The same techniques discussed above for detection of target genes or gene products in cancerous samples can be applied to other body samples. Cancer cells may be sloughed off from cancer lesions and appear in such body samples. By screening such body samples, a simple early diagnosis can be achieved for these cancers. In addition, the progress of therapy can be monitored more easily by testing such body samples for target genes (biomarker) or gene products.

In certain embodiments, a reference sample, reference cell, reference tissue, control sample, control cell, or control tissue is a single sample or combined multiple samples from the same subject or individual that are obtained at one or more different time points than when the test sample is obtained. For example, a reference sample, reference cell, reference tissue, control sample, control cell, or control tissue is obtained at an earlier time point from the same subject or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain embodiments, a reference sample, reference cell, reference tissue, control sample, control cell, or control tissue is a combined multiple samples from one or more healthy individuals who are not the subject or individual. In certain embodiments, a reference sample, reference cell, reference tissue, control sample, control cell, or control tissue is a combined multiple samples from one or more individuals with a disease or disorder (e.g., cancer) who are not the subject or individual. In certain embodiments, a reference sample, reference cell, reference tissue, control sample, control cell, or control tissue is pooled RNA samples from normal tissues or pooled plasma or serum samples from one or more individuals who are not the subject or individual. In certain embodiments, a reference sample, reference cell, reference tissue, control sample, control cell, or control tissue is pooled RNA samples from tumor tissues or pooled plasma or serum samples from one or more individuals with a disease or disorder (e.g., cancer) who are not the subject or individual.

In some embodiments, the sample is a tissue sample from the individual. In some embodiments, the tissue sample is a tumor tissue sample (e.g., biopsy tissue). In some embodiments, the tissue sample is CNS tissue. In some embodiments, the tissue sample is brain tissue (e.g., glial tissue).

A tumor sample may be obtained from a subject by any method known in the art, including without limitation a biopsy, endoscopy, or surgical procedure. In some embodiments, a tumor sample may be prepared by methods such as freezing, fixation (e.g., by using formalin or a similar fixative), and/or embedding in paraffin wax. In some embodiments, a tumor sample may be sectioned. In some embodiments, a fresh tumor sample (i.e., one that has not been prepared by the methods described above) may be used. In some embodiments, a tumor sample may be prepared by incubation in a solution to preserve mRNA and/or protein integrity.

In some embodiments, responsiveness to treatment may refer to any one or more of: extending survival (including overall survival and progression free survival); resulting in an objective response (including a complete response or a partial response); or improving signs or symptoms of cancer. In some embodiments, responsiveness may refer to improvement of one or more factors according to the published set of RECIST guidelines for determining the status of a tumor in a cancer patient, i.e., responding, stabilizing, or progressing. For a more detailed discussion of these guidelines, see Eisenhauer et al., Eur J Cancer 2009; 45: 228-47; Topalian et al., N Engl J Med 2012; 366:2443-54; Wolchok et al., Clin Can Res 2009; 15:7412-20; and Therasse, P., et al. J. Natl. Cancer Inst. 92:205-16 (2000). A responsive subject may refer to a subject whose cancer(s) show improvement, e.g., according to one or more factors based on RECIST criteria. A non-responsive subject may refer to a subject whose cancer(s) do not show improvement, e.g., according to one or more factors based on RECIST criteria.

Conventional response criteria may not be adequate to characterize the anti-tumor activity of immunotherapeutic agents, which can produce delayed responses that may be preceded by initial apparent radiological progression, including the appearance of new lesions. Therefore, modified response criteria have been developed that account for the possible appearance of new lesions and allow radiological progression to be confirmed at a subsequent assessment. Accordingly, in some embodiments, responsiveness may refer to improvement of one of more factors according to immune-related response criteria2 (irRC). See, e.g., Wolchok et al., Clin Can Res 2009; 15:7412-20. In some embodiments, new lesions are added into the defined tumor burden and followed, e.g., for radiological progression at a subsequent assessment. In some embodiments, presence of non-target lesions are included in assessment of complete response and not included in assessment of radiological progression. In some embodiments, radiological progression may be determined only on the basis of measurable disease and/or may be confirmed by a consecutive assessment >4 weeks from the date first documented.

Therapy utilizing modified immune cells of the invention, e.g., CAR T-cells, effectively cleared multiple types of midline H3K27M mutant pediatric diffuse midline gliomas. However, in some instances, the robustness of the immune response leading to reduction and/or clearance of tumor/cancer may be associated with subsequent neuroinflammation in neuroanatomical locations intolerant of swelling (see, e.g., Richman et al., Cancer Immunol. Res. (2018) 6(1); published online Nov. 27, 2017). For example, the thalamus, located just above the cerebellum tentorial notch, is a precarious location for edema, particularly when already expanded by tumor, and swelling in this location can precipitate hydrocephalus from third ventricular compression, increased intracranial pressure and lethal transtentorial herniation.

Accordingly, in some embodiments, clinical monitoring and/or neurointensive management of edema is utilized together with immunotherapeutic compositions and methods of the invention in order to achieve successful clinical results. The invention is not limited by the type of monitoring or the type of management utilized. Indeed, any means of monitoring cranial inflammation and/or swelling may be used. In like manner, any means of managing cranial inflammation and/or swelling may be used. In one non-limiting example, monitoring for hydrocephalus and/or signs of increased intracranial pressure is performed during inpatient monitoring with frequent neurological and fundoscopic exams and/or neuroimaging. In some embodiments, neurosurgical interventions, such as intraventricular shunt placement for relief of hydrocephalus or even craniectomy for decompression, is utilized to support patients through tumoricidal neuroinflammation.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example 1

Materials and Methods

DIPG/DMG cultures. Patient-derived glioma cell cultures were generated as previously described (see, e.g., Lin and Monje, J Vis Exp, 2017(121)). Briefly, postmortem tumor tissue was dissociated mechanically and enzymatically (Liberase DH, Roche) prior to separation of myelin and debris by sucrose centrifugation. Neurosphere-generating cultures were maintained in serum-free media supplemented with B27 (ThermoFisher), EGF, FGF, PDGF-AA, PDGF-BB (Shenandoah Biotechnology), and Heparin (StemCell Technologies). All cultures were validated and monitored by STR-fingerprinting (See Table 1, below) and verified to be mycoplasma-free within the previous 6 months (MycoAlert Plus, Lonza).

TABLE 1

| Cell line STR fingerprinting | | | | | | | | | | | |
|---|---|---|---|---|---|---|---|---|---|---|---|
| Cell | Histone | STR Fingerprint | | | | | | | | | |
| Culture | Status | AMEL | CSF1PO1 | D13S317 | D15S539 | D21S11 | D5S818 | D7S820 | TH01 | TPOX | vWA |
| SU-DIPG6 | H3F3A K27M | X/X | 10/11 | 11/ | 8/13 | 29/31 | 10/12 | 8/9 | 7/8 | 8/11 | 17/18 |
| SU-DIPG13 | H3F3A K27M | X/X | 9/10 | 11/12 | 11/12 | 30/OL (overload) | 12/12 | 9/9 | 6/7 | OL/8 | 13/18 |
| SU-DIPG17 | H3F3A K27M | X/Y | 13/13 | 9/9 | 9/12 | 28/29 | 11/11 | 8/9 | 7/7 | 8/11 | 18/19 |
| SU-DIPG19 | H3F3A K27M | X/Y | 10/11 | 13/14 | 9/13 | 30/30 | 11/12 | 10/10 | 9.3/9.3 | 8/11 | 17/18 |
| SU-DIPG21 | HIST1H3B K27M | X/Y | 11/12 | 8/13 | 10/10 | 30/32 | 10/11 | 8/9 | 6/6 | 8/12 | 16/19 |
| SU-DIPG25 | H3F3A K27M | X, X | 12, 12 | 8, 11 | 12, 13 | 30, 35 | 11, 13 | 10, 12 | 9, 9 | 7, 8 | 14, 18 |

TABLE 1-continued

Cell line STR fingerprinting

| Cell | Histone | STR Fingerprint | | | | | | | | | |
|------|---------|------|--------|---------|---------|--------|--------|--------|------|------|------|
| Culture | Status | AMEL | CSF1PO1 | D13S317 | D15S539 | D21S11 | D5S818 | D7S820 | TH01 | TPOX | vWA |
| SU-DIPG27 | H3F3A K27M | X, Y | 11, 12 | 9, 12 | 10, 12 | 30, 33.2 | 11, 11 | 9, 12 | 6, 6 | 8, 11 | 16, 17 |
| SU-DIPG33 | HIST1H3B K27M | X, Y | 11, 12 | 8, 10 | 10, 12 | 30, 30 | 10, 12 | 10, 12 | 8, 9 | 8, 11 | 14, 14 |
| SU-DIPG35 | H3F3A K27M | X, X | 10, 12 | 12, 13 | 9, 12 | 31.2, 32.2 | 12, 12 | 10, 13 | 6, 7 | 3, 8 | 15, 16 |
| VUMC-DIPG10 | H3 WT | X, X | 10, 11 | 13, 13 | 11, 12 | 30, 30 | 10, 13 | 12, 12 | 7, 9 | 8, 11 | 15, 19 |
| SU-pcGBM2 | H3 WT | X/Y | 10/11 | 11/ | 9/11 | 28/30.2 | 11/ | 11/12 | 9.3/ | 8/12 | 17/18 |
| SU-pSCG1 | H3F3A K27M | X/Y | 10/12 | 12/ | 11/12 | 28/29 | 11/12 | 10/ | 9.3/ | 8/11 | 16/18 |
| QCTB-R059 | H3F3A K27M | X/X | 12, 13 | 12/ | 11/ | 29, 31.2 | 12/ | 8, 11 | 9/ | 11, 13 | 13, 16 |

SU-DIPG6 and SU-DIPG13 have been previously referenced and are identical to SU-DIPG-VI and SU-DIPG-XIII, respectively.

Cell surface screening. Cell surface markers present on DIPG cell cultures were screened using a panel of monoclonal antibodies against human cell surface markers (Lyoplate, BD Biosciences). Low passage (<12) DIPG cultures expanded from tumor tissue collected at autopsy in serum-free, neurosphere forming conditions were allotted to 96 well plates and blocked with 1 μg of goat IgG per million cells to reduce nonspecific binding of secondary antibodies subsequently used in the assay. Cells were then incubated sequentially with primary and secondary antibodies with intermediate wash steps according to the manufacturer's instructions. Dead cells were then labeled with a Live/Dead violet stain (ThermoFisher), and following washes cells were fixed in 1% PFA for 10 minutes at room temperature. The following day, stained cells were analyzed by flow cytometry. Doublets and dead cells were excluded by gating, and the median fluorescence intensity of antibody labeling for each target on the panel was normalized to the median fluorescence intensity (MFI) for the matched isotype control.

Immunohistochemistry and light microscopy. Primary DIPG patient tumor samples were fixed overnight in 4% paraformaldehyde/PBS upon arrival, and then transferred to 30% sucrose until the tissue samples sank (2-3 days). Tissues were then transferred to cryomolds and embedded in OCT (TissueTek). 10 micron cryosections were generated on a cryostat (Leica), and endogenous peroxidase activity was neutralized (Bloxall, Vector Laboratories) prior to permeabilization (0.3% Triton X-100, TBS) and blocking (5% horse serum, Vector Laboratories). Sequential double immunohistochemistry was conducted for H3K27M (Abcam ab190631, 1:1000, 1 hr RT) and GD2 (14g2a, BD, 1:500, 1 hr at RT). H3K27M was developed with a polymer-based peroxidase secondary (ImmPRESS VR anti-rabbit IgG, Vector Laboratories, 30 minutes at RT) and DAB substrate (BD, 45 seconds at RT). Under these conditions, H3K27M+ cells could be routinely identified in multiple tissues confirmed to bear both H3F3A and HISTH1B3 mutations by Sanger sequencing. After quenching the DAB substrate development in TBS and staining with the 14g2a primary antibody, GD2 signal was developed using a polymer-based alkaline phosphatase secondary (ImmPRESS AP anti-mouse IgG, Vector Laboratories, 30 minutes at RT) and blue alkaline phosphatase substrate (Vector Blue AP substrate kit, Vector Laboratories, 150 seconds at RT). AP development was quenched in TBS, and samples were mounted and imaged (Zeiss AxioObserver). For hematoxylin-eosin staining, mice were deeply anesthetized by intraperitoneal injection of tribromoethanol and perfused transcardially with cold PBS, brains were removed and fixed overnight in 4% paraformaldehyde/PBS. Brains were then transferred to 70% ethanol and subsequently embedded in paraffin, sectioned, and stained with hematoxylin/eosin. H&E histology was then analyzed.

Immunofluorescence and confocal microscopy. Mice were deeply anesthetized with tribromoethanol (Avertin) before being perfused transcardially with cold PBS. Brains and other tissues of interest were then removed and fixed overnight in 4% PFA/PBS before being transferred to 30% sucrose and allowed to sink (2-3 days). Serial 40 micron coronal sections were then cut on a freezing microtome and floated in a tissue cryoprotectant solution (glycerol, ethylene glycol, phosphate buffer) before storage at −20° C. Serial sections were then stained overnight at 4C. Primary antibodies used were: rabbit anti-H3K27M (Abcam, 1:1000), rabbit anti-cleaved caspase-3 (Cell Signaling Technology, 9661, 1:250), mouse anti-NeuN (Millipore, MAB377, 1:500), and rabbit Iba1 (Wako, 019-19741, 1:500). Secondary antibodies raised in donkey and conjugated with AlexaFluor 594 or 647 were used at 4C overnight to detect primary labeling (Jackson ImmunoResearch, 1:500). Mounted samples were imaged by confocal microscopy (Zeiss LSM710), and acquired Z stacks through the tumor region were flattened by maximum intensity projection (ImageJ). To quantify tumor cell density, cells within the borders of infiltrating tumor in acquired micrographs were counted and normalized to the tumor area (ImageJ), and the sum of all cells was normalized to the total area investigated across 3-4 sections for each animal in a 1:12 series.

RT-qPCR. Cultures were plated in triplicate under standard growth conditions and harvested in Trizol 24 hours later. After DNAse treatment, extracted RNA was reverse transcribed (Maxima first strand, ThermoFisher) and utilized as template for qPCR reactions (Maxima SYBR green, ThermoFisher). Primers utilized are listed in Table 2, below.

US 12,582,675 B2

39

TABLE 2

Primers used for RT-PCR

| Gene | Primer | SEQ ID NO: | Primer | SEQ ID NO: |
|---|---|---|---|---|
| B4GALNT1 | ACTGGTCACT TACAGCAGCC | 1 | GCGGGTGTCT TATGCGGATA | 8 |
| B3GALT4 | GGTTTTGCAC AGCGAGGAAG | 2 | AGGCCACTGC TCCTCTGATA | 9 |
| ST3GAL5_1 | CACACCCTGA ACCAGTTCGA | 3 | TCAAGGTCAG ACAGTGGTGC | 10 |
| ST8SIA1 | AGAGCATGTG GTATGACGGG | 4 | ATCCCACCAT TTCCCACCAC | 11 |
| ST8SIA5 | ATTAAGAGAG GCCTCCAGTT TG | 5 | CCTCAGCTCC AGGCATCTTG | 12 |
| B4GALT6 | CCATACCTCC CCTGTCCAGA | 6 | CATGACCCCC TGGCTCAAT | 13 |
| HPRT1 | CTGGCGTCGT GATTAGTGAT | 7 | TCTCGAGCAA GACGTTCAGT | 14 |

No-template and RT-controls did not significantly amplify.

CAR construction, retroviral vector production and T cell transduction. GD2.BBz and CD19.BBz CAR retroviral vectors were constructed (see, e.g., Lynn et al., Blood, 2015. 125(22): p. 3466-76). GD2.BBz and CD19.BBz CAR-encoding retroviral supernatants were produced via transient transfection of the 293GP cell line (see, e.g., Haso et al., Blood, 2013. 121(7): p. 1165-74). Briefly, 293GP cells were transfected on poly-d-lysine coated plates via Lipofectamine 2000 (Life Technologies) with the plasmids encoding the CARs and the RD114 envelope protein. Supernatants were collected 48 and 72 hours after transfection. Isolated human T-cells were activated with anti-CD3/CD28 beads (Life Technologies) in a 3:1 bead:cell ratio with 40 IU/ml IL-2 for 3 days. Activated T cells were then retrovirally transduced on days 3 and 4 (see, e.g., Long et al., Nat Med, 2015. 21(6): p. 581-90) using Retronectin (Takara) coated plates, and cultured in 300 IU/ml IL-2. Anti-CD3/CD28 beads were removed on day 5. Media and IL-2 were changed every 2-3 days. Transduction efficiencies were checked by flow cytometry with the 1A7 anti-idiotype antibody (see, e.g., Sen et al., J Immunother, 1998. 21(1): p. 75-83) for the GD2.BBz CAR and with the FMC63 anti-idiotype antibody 136.20.1 (see, e.g., Jena et al., PLoS One, 2013. 8(3): p. e57838) or Protein L (Pierce) for the CD19.BBz CAR.

In vitro cytokine generation and cell killing. Standard luciferase based assays were carried out to evaluate CART cell cytolytic ability (see, e.g., Lynn et al., Blood, 2015. 125(22): p. 3466-76). Firefly luciferase expressing target tumor cells (10,000 per well) were co-incubated with CAR T cells for 24 hours at effector-to-target (E:T) ratios ranging from 10:1 to 1:1. The STEADY-GLO Luciferase Assay System (Promega) was used to measure residual luciferase activity from remaining targets, and lysis was calculated as follows: percent lysis=100−[[(average signal from T cell-treated wells)/(average signal from untreated target wells)]× 100].

Cytokine production by CAR T-cells in vitro was evaluated by co-incubation of CAR+ T-cells with target tumor cells at a 1:1 ratio (100,000 cells each), with CAR+ T-cell counts incorporating the transduction efficiency as assessed by anti idiotype staining and flow cytometry. The total number of T-cells used for the control CD19-4-1BBz CAR T-cells matched the number used for the GD2-4-1BBz CAR T-cells to ensure that the total number of T-cells remained consistent across groups. After 24 hours, supernatants were harvested and cytokine levels measured by ELISA for IL-2 and IFN-gamma (BioLegend).

T-cell proliferation. GD2-CAR T-cells on Day 15 of culture were labeled with Cell Trace Violet (ThermoFisher) according to manufacturer protocol. Labeled GD2-CAR T-cells were either incubated with no tumor, VUMC-DIPG10 (GD2 negative, H3K27M negative) or SU-DIPG13 (GD2 positive, H3K27M positive). After five days of incubation, cells were collected and analyzed by flow cytometry for proliferation. Analysis was performed on CAR+ T-cells only as identified by anti687 idiotype staining.

Figures 3A, 3B:
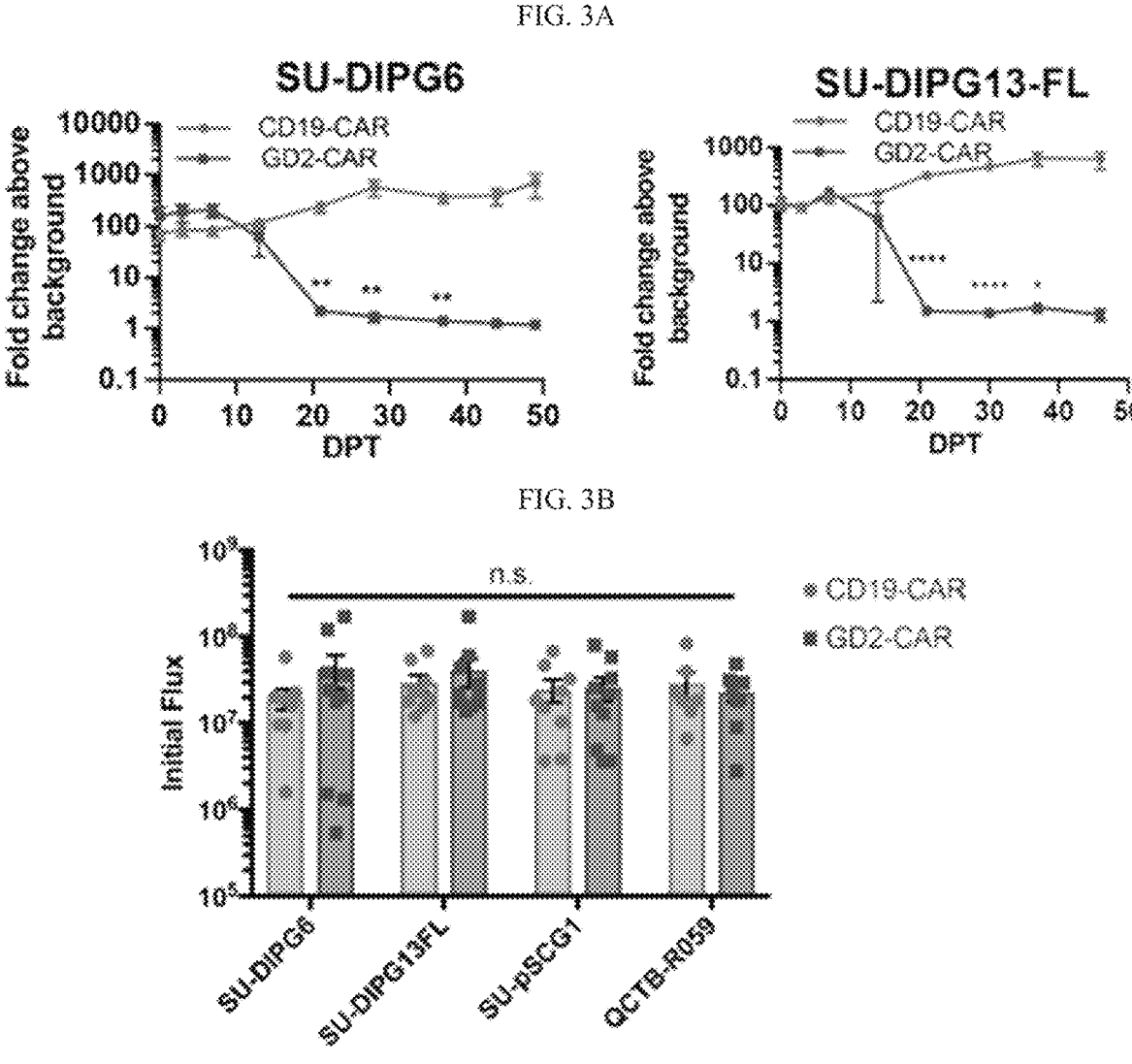
FIGS. 3A-3B show that a single intravenous dose of GD2-CAR T cells cleared luciferase-expressing patient-derived DIPG xenografts to background bioluminescence levels.

Orthotopic xenograft generation and treatment. Orthotopic DIPG xenografts were generated (see, e.g., Grasso et al., Nat Med, 2015. 21(6): p. 555-9). All in vivo experiments were approved by the Stanford University Institutional Care and Use Committee and performed in accordance with institutional guidelines. Animals were housed according to institutional guidelines with free access to food and water on a 12-hour light/dark cycle. Briefly, patient-derived DIPG cell cultures previously transduced with a lentivirus expressing eGFP and firefly luciferase driven by the CMV promoter were infused by stereotaxic injector (Stoelting) into the pons (coordinates lambda AP-3 mm, DV-3 mm) of cold anesthetized newborn (P0-2) NSG mice (Jax). Orthotopic pediatric spinal cord glioma xenografts were generated by stereotaxic injection of SU-pSCG1 transduced with a lentivirus expressing eGFP and firefly luciferase driven by the CAG promoter into the medulla of isoflurane anesthetized P35 NSG mice (coordinates lambda ML+0.7 mm, AP-3.5 mm, DV-4.5 mm, 600k cells). Orthotopic thalamic glioma xenografts were generated by stereotaxic injection of QCTB-R059 transduced with a lentivirus expressing eGFP and firefly luciferase driven by the CMV promoter into the thalamus of isoflurane-anesthetized P35 NSG mice (coordinates bregma ML+0.8 mm, AP−1 mm, DV −3.5 mm, 600k cells). Tumors were then allowed to develop for 60 days. Prior to treatment, tumor burden was assessed by in vivo luminescence imaging (IVIS Spectrum, PerkinElmer), and total flux was calculated by included software (Living Image, Perkin Elmer) as the radiance through standard circular ROIs centered on the animal's head. Paired background regions were quantified using circular ROIs over the animal's flank where no significant luminescence was detected above background. Animals were rank-ordered by tumor burden and distributed sequentially into GD2 or CD19-CAR treatment groups, such that populations of equivalent initial tumor burden underwent each arm of therapy. Initial burden assessed in this manner was equivalent across treatment groups and engrafted cell lines (see FIG. 3). SU-DIPG13P* cells were injected into the pons of isoflurane-anesthetized P35 NSG mice (coordinates lambda ML+1 mm, AP-0.8 mm, DV-5 mm, 600k cells) and allowed to develop for 14 days before T-cell administration. CAR T-cells with concentrations adjusted to deliver $1\times10^7$ transduced cells in 200 microliters of PBS (assessed by idiotype staining using flow cytometry, routinely >60%) were then administered by intravenous injection into the tail vein of animals. Where transduction efficiencies varied between GD2-CARs and CD19-CARs, the concentration of CD19-CAR cells was adjusted to match the total dose of human T-cells present in the GD2-CAR infusion. Tumor burden was monitored longitudinally by in vivo luminescence imaging. Due to the nature of GD2-CAR response, blinding in initial cohorts was deemed ineffective and subsequently not performed. All images were scaled to display minimum flux intensity as $5 \times 10^4$ and maximum as $5 \times 10^6$, then images of individual animals were arranged with like treated animals in the cohort for display in the FIGS. Trial endpoint at 50 days post treatment was determined in initial cohorts where substantial hair loss, reduced activity, and weight loss in both GD2-CAR and CD19-CAR groups that triggered morbidity criteria for euthanasia.

CRISPR/Cas9-mediated deletion of GD2 synthase. Deletion of GD2 synthase (B4GALNT1) in SU-DIPG13 cells was accomplished by electroporation of DIPG13 with Cas9: sgRNA ribonucleoprotein complexes as described (See Hendel et al., Nat Biotechnol 33, 985-989 (2015)). Briefly, guide RNAs targeting exon1 of B4GALNT1 (CGUCCCGGGUG-CUCGCGUAC (SEQ ID NO: 15) and CCGGCUACCUC-UUGCGCCGU (SEQ ID NO: 16), Synthego) were incubated with Cas9 nuclease to form ribonucleoprotein complexes and electroporated with an Amaxa 4-D nucleofector (SE Buffer, program DS-112). In parallel, a control gRNA targeting the AAVS1 locus46 (GGGGCCAC-UAGGGACAGGAU (SEQ ID NO: 17)) was electroporated with Cas9 nuclease as a ribonucleoprotein complex using identical parameters. GD2-negative cells electroporated with B4GALNT1-targeting gRNAs were isolated by FACS sorting, and deletion was confirmed by Sanger sequencing and TIDE analysis. (see Nucleic Acids Res 42, e168 (2014)).

Statistics and Reproducibility. Statistical tests were conducted using Prism (GraphPad) software unless otherwise indicated. Gaussian distribution was confirmed by the Shapiro-Wilk normality test. For parametric data, unpaired, two-tailed Student's t-tests and one-way ANOVA with Tukey's post hoc tests to further examine pairwise differences were used. For survival analysis, a log-rank (Mantel-Cox) test was used. A level of $P < 0.05$ was used to designate significant differences. On the basis of the variance of xenograft growth in control mice, at least 3 mice per treatment group were used to give 80% power to detect an effect size of 20% with a significance level of 0.05. For all animal experiments, the number of independent mice used is shown in the FIG. or listed in the brief description of the drawings. For each of the five patient-derived xenograft models used, at least two independent cohorts were tested (i.e. independent litters of mice on different days with independent batches of cells.) For cytokine and in vitro cell killing experiments, n=3 and experiments were repeated twice.

Example 2

Identification of the Overexpression of Disialoganglioside GD2 in Histone H3 K27M (H3K27M) Mutated Diffuse Intrinsic Pontine Glioma (DIPG)

In order to identify potential targets for immunotherapy (e.g., CAR T cell therapy) in DIPG, cell surface antigens (see FIG. 13) were screened in patient-derived DIPG cultures (See FIG. 1A). Significant overlap between independent patient-derived cultures (see FIG. 1B) indicated conservation of a core group of surface markers across DIPG patients. From these common targets, the disialoganglioside GD2 was identified as commonly expressed at high levels on each of the four patient-derived DIPG cultures screened. Hit validation by flow cytometry confirmed uniform and remarkably high levels of GD2 expression in all H3K27M DIPG cultures examined, including both those with the H3F3A K27M mutation and the less common HIST1H3B K27M mutation (see FIG. 1C, Wu et al., Nature Genetics, 2012. 44(3): p. 251-253; Khuong-Quang et al., Acta Neuropathol, 2012. 124(3): p. 439-47; and Schwartzentruber et al., Nature, 2012. 482(7384): p. 226-31). Intriguingly, GD2 expression was identified as being far lower in histone H3 WT pediatric high-grade gliomas (pHGG), including a case diagnosed as DIPG (See FIG. 1C).

Figure 1E:
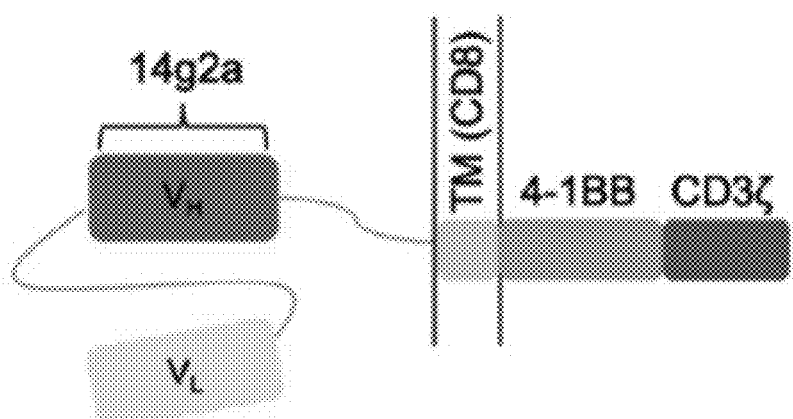
Figures 1F, 1G:
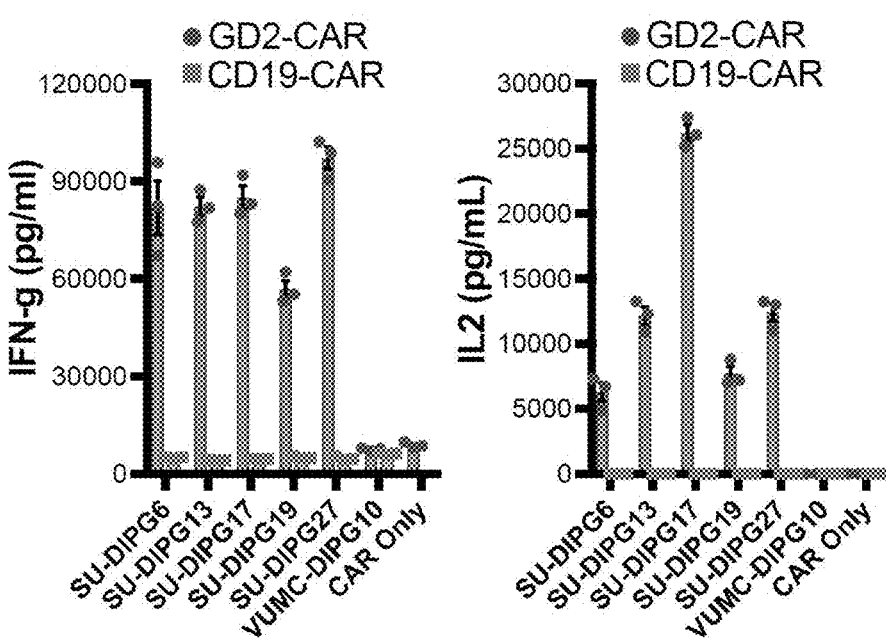
Figure 1H:
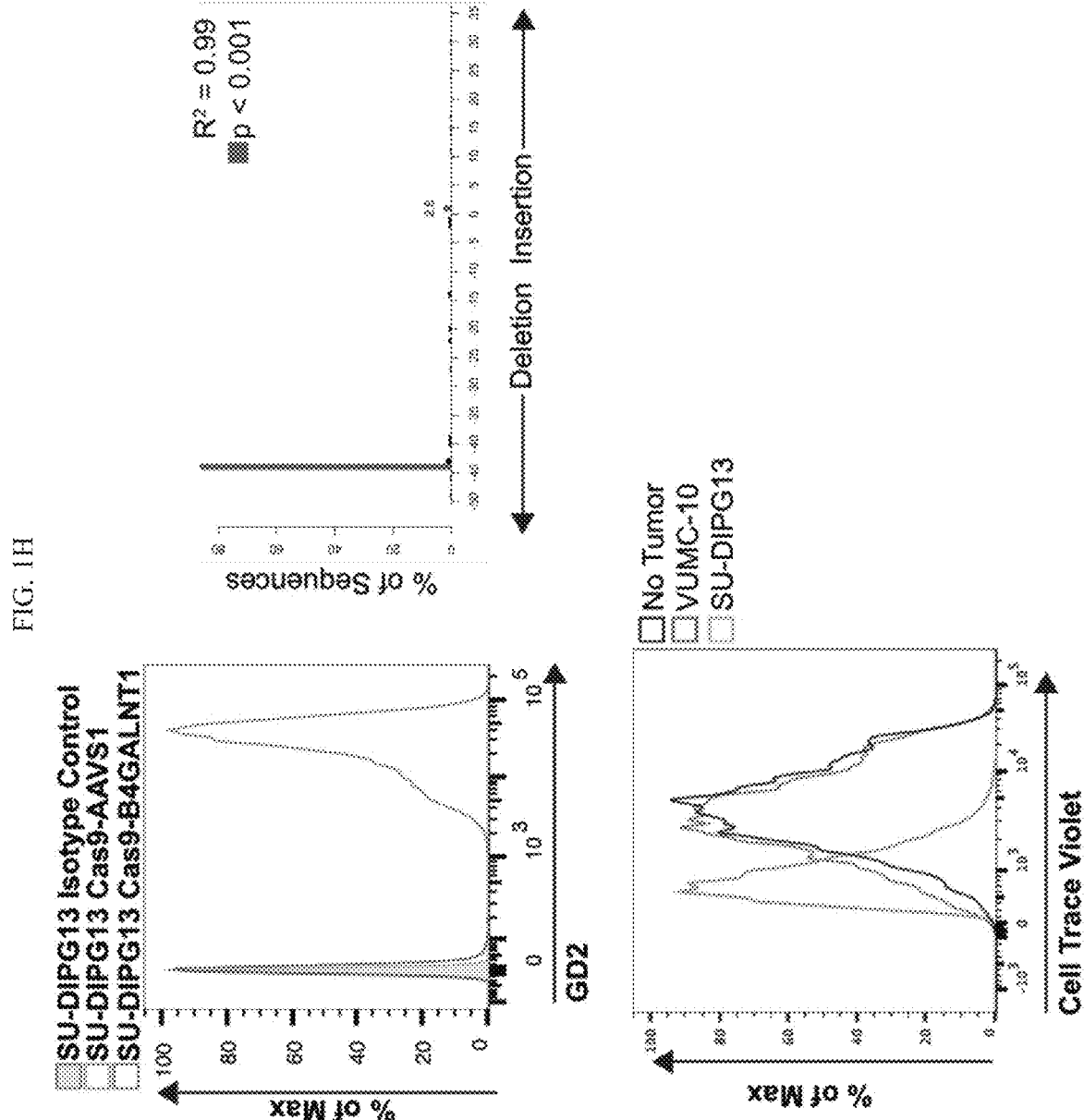
Figure 1I:
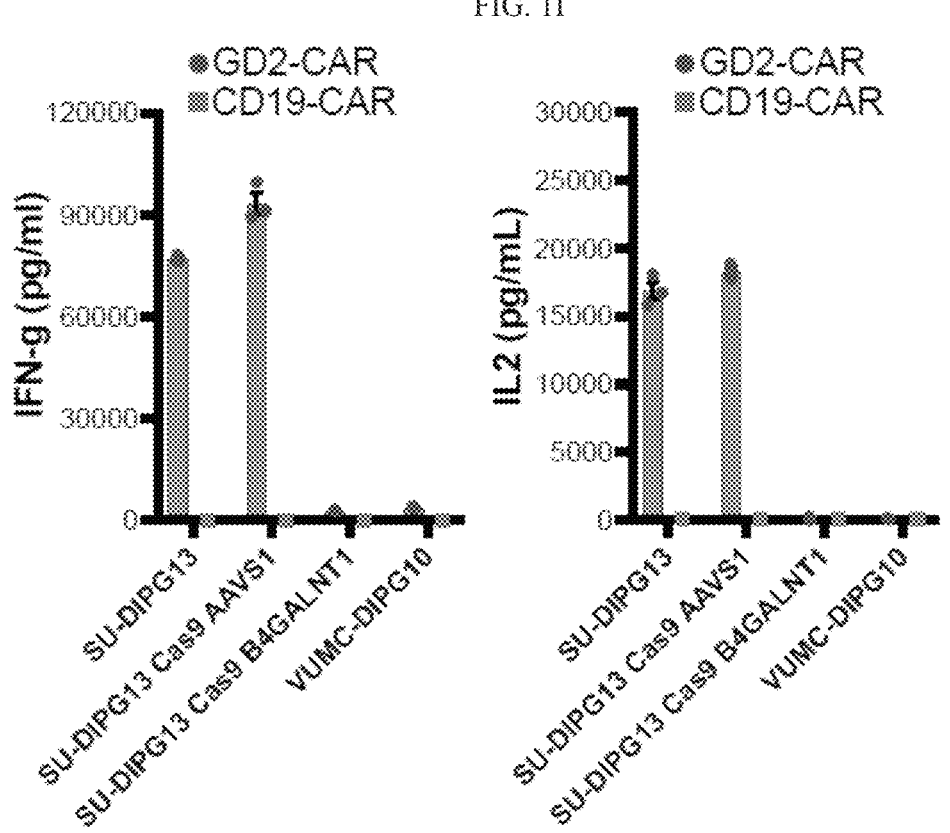
Figure 1J:
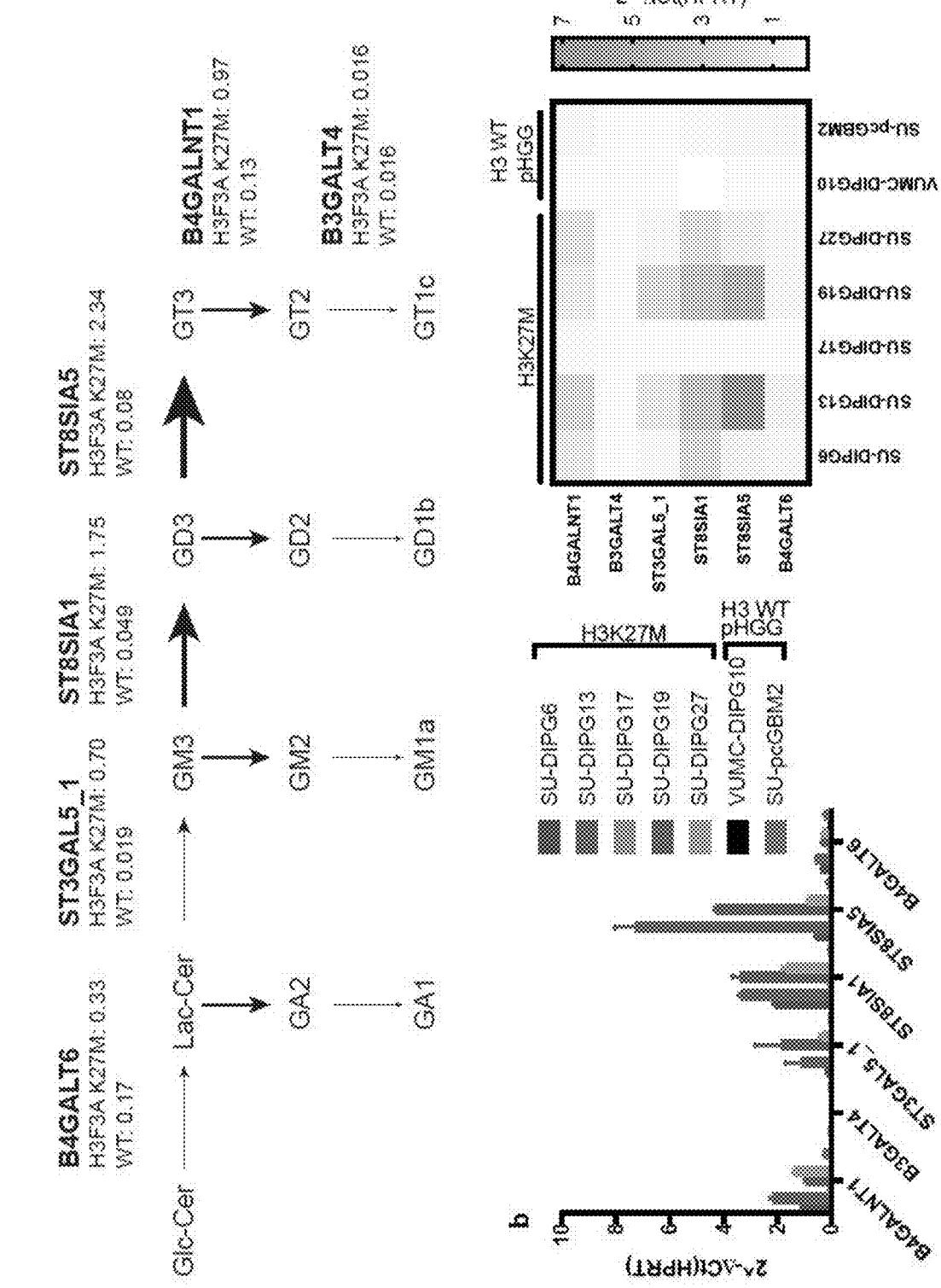

In order to assess whether transcriptional perturbations resulting from the H3K27M mutation might be linked to increased GD2 expression, gene expression of ganglioside synthesis enzymes was profiled in a panel of patient-derived DIPG and pHGG cultures and consistently higher expression of upstream ganglioside synthesis enzymes was found in cultures bearing the H3K27M mutation (see FIG. 1J). Double immunostaining of primary human DIPG tissue for H3K27M to identify infiltrating malignant cells and GD2 confirmed local expression of GD2 in the native tumor context (see FIG. 1D).

Example 3

GD2-Dependent Cell Killing of DIPG Cells with GD2-CAR T Cells

Human GD2-targeting CAR T cells were generated employing a 14g2a scFv and 4-1BBz costimulatory domain (see FIG. 1E and Long et al., Nature Medicine, 2015. 21(6): p. 581-590). Significant GD2-dependent cell killing (see FIG. 1F) and cytokine generation (see FIG. 1G) was observed upon exposure to patient derived DIPG cultures relative to control CD19-CAR T-cells incorporating 4-1BBz (CD19-CAR). Notably, GD2-directed CAR T cells did not produce significant cytokines or induce cell killing when exposed to the H3WT, GD2-negative VU-DIPG10 patient-derived DIPG culture, thereby demonstrating therapeutic specificity of GD2-CARs toward H3K27M DIPG.

To further confirm the targeting specificity of GD2-CAR T-cells, CRISPR-Cas9-mediated deletion of GD2 synthase (B4GALNT1) in patient-derived DIPG cells was used to generate GD2 knockout DIPG cells (see FIGS. 1H(a), 1H(b) and 1H(c)). Loss of GD2 antigen expression eliminated cytokine production by the GD2-CAR T-cells in comparison to untreated or DIPG cells electroporated with a control guide sequence targeting the AAVS1 locus (see FIG. 1I). These data indicate specific reactivity of GD2-CAR T-cells to H3K27M+ glioma cells.

Example 4

In Vivo Efficacy of GD2-Directed CAR T Cells Against DIPG

Figure 2A:
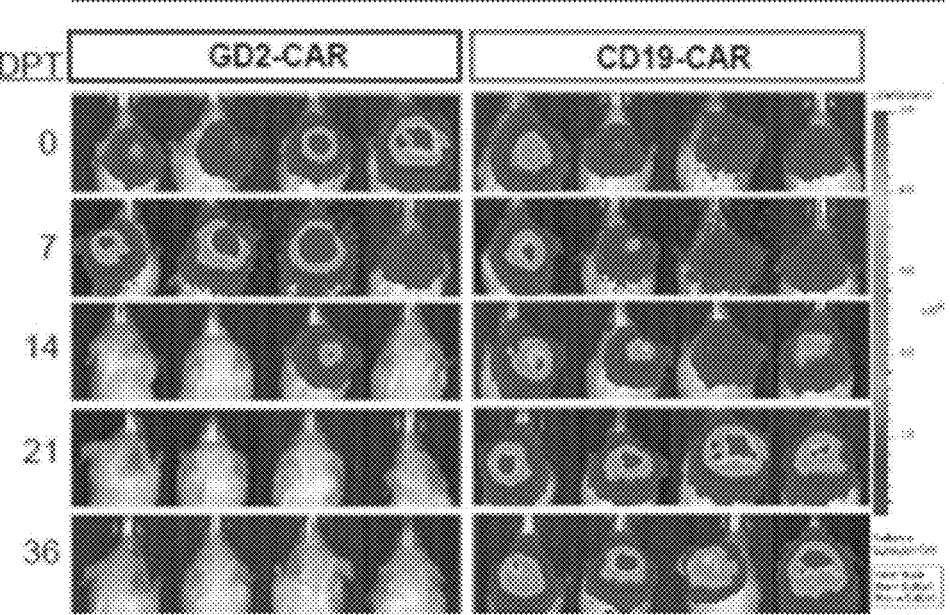
FIGS. 2A-2I show that GD2-targeting CAR immunotherapy achieved potent and lasting antitumor response in DIPG orthotopic xenografts.
Figures 2B, 2C:
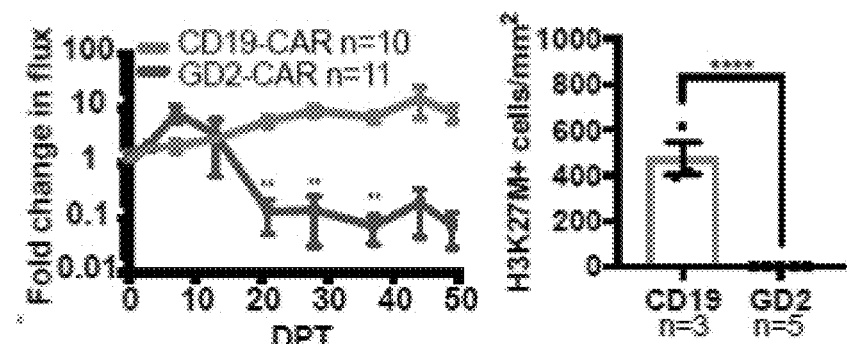
Figure 2D:
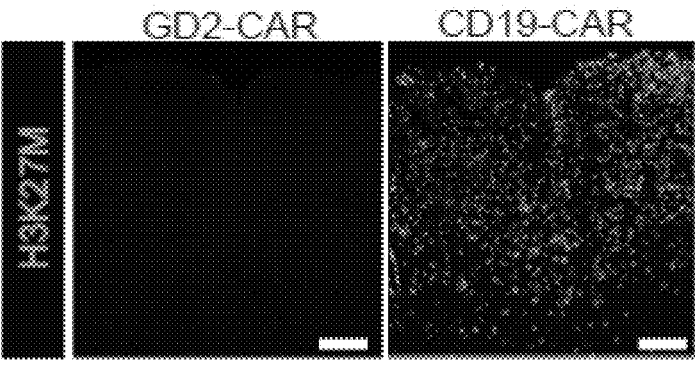
Figure 2E:
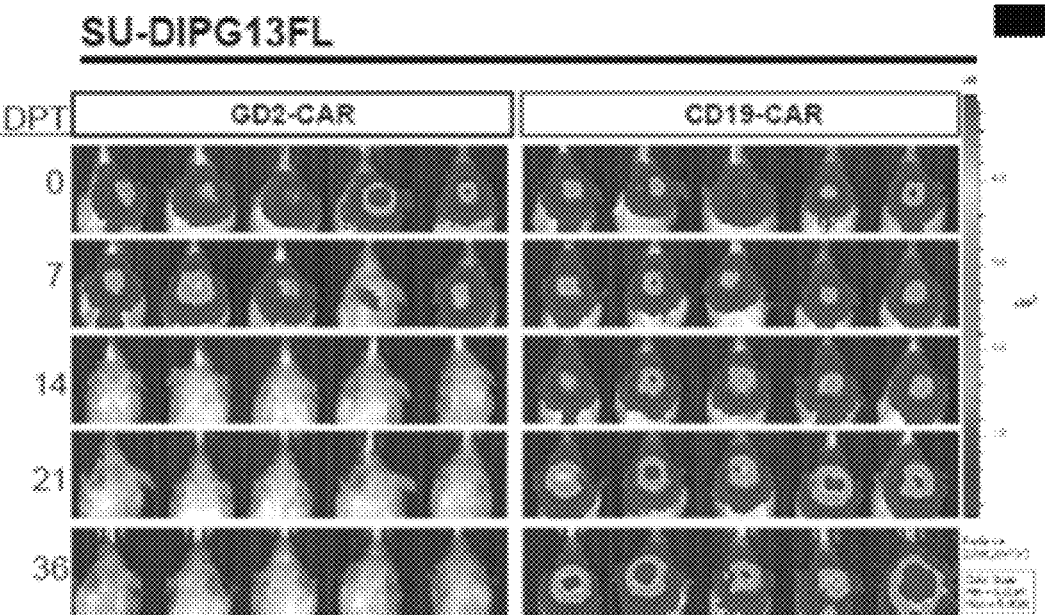
Figure 2F:
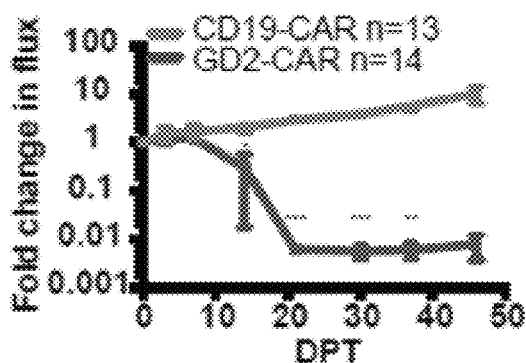
Figure 2G:
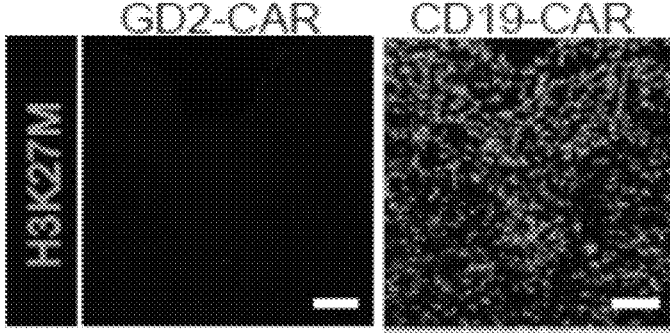
Figures 2H, 2I:
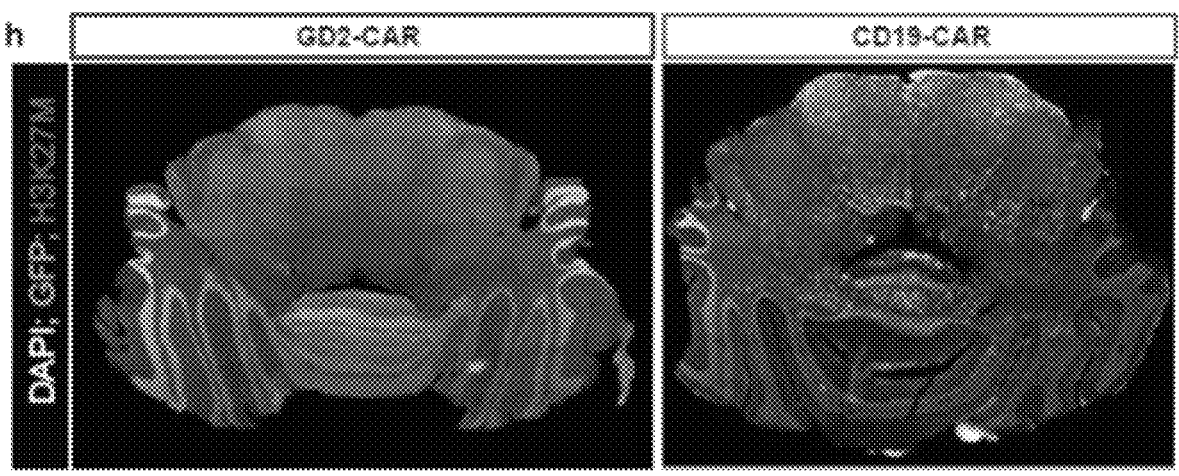

In order to evaluate the in vivo efficacy of GD2-directed CAR T cells against DIPG, orthotopic mouse xenografts of DIPG cultures derived from post-mortem patient tissue were prepared and then transduced with a luciferase-expressing construct to enable longitudinal monitoring of tumor burden. The xenograft models faithfully recapitulate the diffusely infiltrating histology of DIPG (see, e.g., Monje et al. *Proc Natl Acad Sci USA* 108, 4453-4458 (2011); and Qin et al., *Cell* 170, 845-859 e819 (2017). Mice were distributed by initial tumor burden into equivalent treatment and control groups before receiving $1 \times 10^7$ GD2-CAR or CD19-CAR T-cells by a single intravenous injection 7-8 weeks after establishment of pontine xenografts. Within 40 days post-treatment (DPT), marked reductions in tumor burden were observed across two independent GD2-CAR T-cell treated cohorts of mice bearing SU-DIPG6 xenografts (see FIG. 2A and Grasso et al., *Nat Med* 21, 555-559 (2015)). Similar results were observed in a second patient-derived xenograft model, SU-DIPG13FL30 (See FIG. 2E). All GD2-CAR treated animals demonstrated complete tumor clearance by bioluminescence imaging (See FIG. 3). By contrast, no mice in the CD19-CAR T-cell control groups exhibited significant tumor regression. At 50 DPT brains were harvested, and immunostaining for the mutant histone H3K27M—present in all engrafted tumor cells—revealed that GD2-CAR treated tumors had been largely eradicated (see FIGS. 2C,D, G,H,I).

Figure 4:
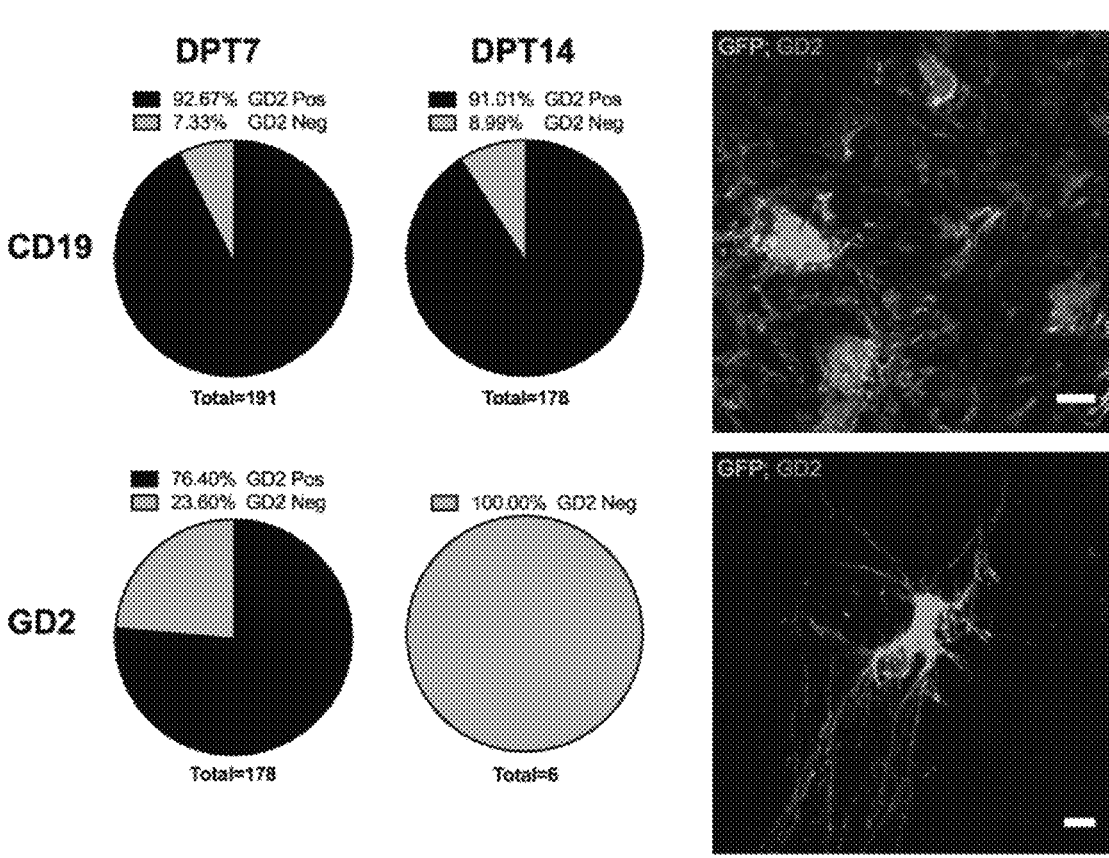
FIG. 4 shows selective pressure of GD2 CAR T cell therapy in DIPG xenografts. Immunofluorescent staining for GD2 (clone 14g2a) in CD19 or GD2-CAR T cell-treated SU-DIPG13FL xenografts demonstrated selective pressure of GD2-CAR T cell therapy during the acute phase of tumoricidal activity. By DPT14, when the vast majority of parenchymal tumor had been cleared in GD2 CART cell-treated animals, the small number of remaining GFP+ tumor cells did not co-stain for GD2. Scale bar represents 10 microns. Total n given for each chart indicates number of cells assessed across 2 animals for each CAR/timepoint combination.
Figure 5B:
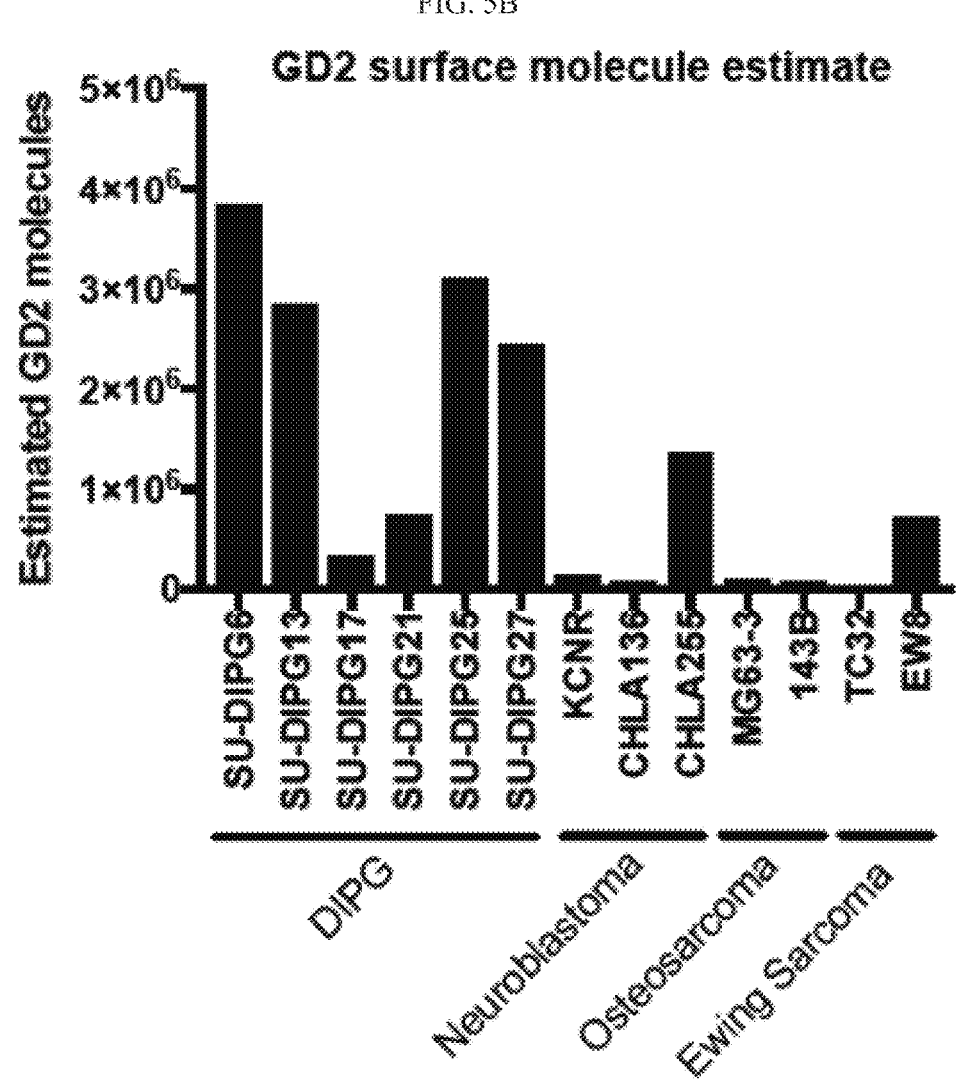

The small number of H3K27M+ tumor cells that remain after treatment were negative for GD2 by immunostaining (see FIG. 4). The data evidences that the potency of the GD2-CAR T cells was driven by the high expression of the target antigen in H3K27M mutant DIPG, which was observed to be consistently higher than that present on GD2+ neuroblastoma and sarcoma cell lines (see FIG. 5).

Figure 7:
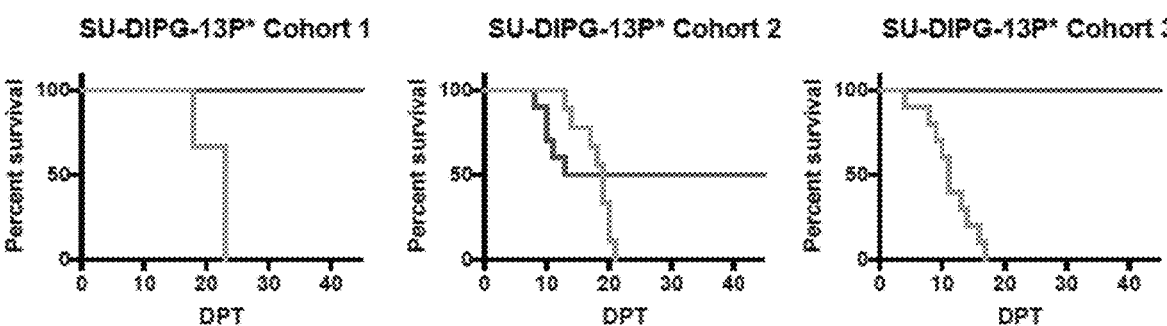
FIG. 7 shows the survival benefit of GD2 CAR T cell therapy assessed in three independent cohorts of SU-DIPG13P* xenografts. Combined cohort data and statistical analysis is presented. In 1/3 cohorts (Cohort 2), several deaths in GD2 CAR T cell-treated animals were observed acutely, from DPT8-13. Animals were as follows: Cohort 1 CD19-CAR, 5 GD2-CAR, Cohort 2 CD19-CAR, 10 GD2-CAR, Cohort 3 CD19-CAR, 9 GD2-CAR.

Most patient-derived orthotopic DIPG xenograft models require many months for lethality, limiting the ability to monitor survival benefit due to development of xenogeneic graft versus host disease (GVHD) after treatment with human T cells (see, Ali et al., PLoS One 7, e44219 (2012)). SU-DIPG-13P* was therefore used as it is a model that exhibits a dense pattern of growth histologically (see, Nagaraja et al., Cancer Cell 31, 635-652 e636 (2017)), and is consistently lethal within one month. Substantial improvement in survival was observed in GD2-CAR treated animals compared with CD19-CAR treated controls (see FIG. 6A). However, in one out of three independent cohorts, lethal toxicity occurred in several GD2-CAR T-cell treated animals, while all GD2-CAR T-cell treated animals in the other cohorts survived to endpoint (see FIG. 7). GD2-CAR treated animals that survived the initial phase of glioma clearance returned to a visibly healthy state indistinguishable from untreated immunodeficient mice until the onset of GVHD symptoms 4+ weeks after CAR administration that invariably triggered endpoint criteria (see FIG. 8). Histologic analysis of the brains of endpoint GD2-CAR treated animals revealed clearance of this high-burden tumor while surrounding neural tissues appeared grossly normal (see FIG. 6B)

In order to better understand the etiology of treatment-related toxicity in these DIPG xenograft models, the brains of treated SU-DIPG6 xenograft bearing mice were acutely examined at DPT14 (FIG. 6C). GD2-CAR treatment was accompanied by a widespread inflammatory infiltrate involving brain parenchyma, meninges and ventricles that was most prominent in the brainstem. Ventriculomegaly was observed, consistent with hydrocephalus. Histologically normal appearing neurons were observed to be present throughout the pons, hippocampus, and cortex of GD2-CAR T-cell-treated animals with no evidence of neuronal cell killing nor other tissue destruction in this model (See FIG. 6C). Thus, neuropathological evaluation indicated that the toxicity described above resulted from brainstem inflammation and hydrocephalus due to fourth ventricular compression during the tumor-clearing interval and not on-target, off-tumor toxicity of GD2-CAR T-cells.

Figure 9:
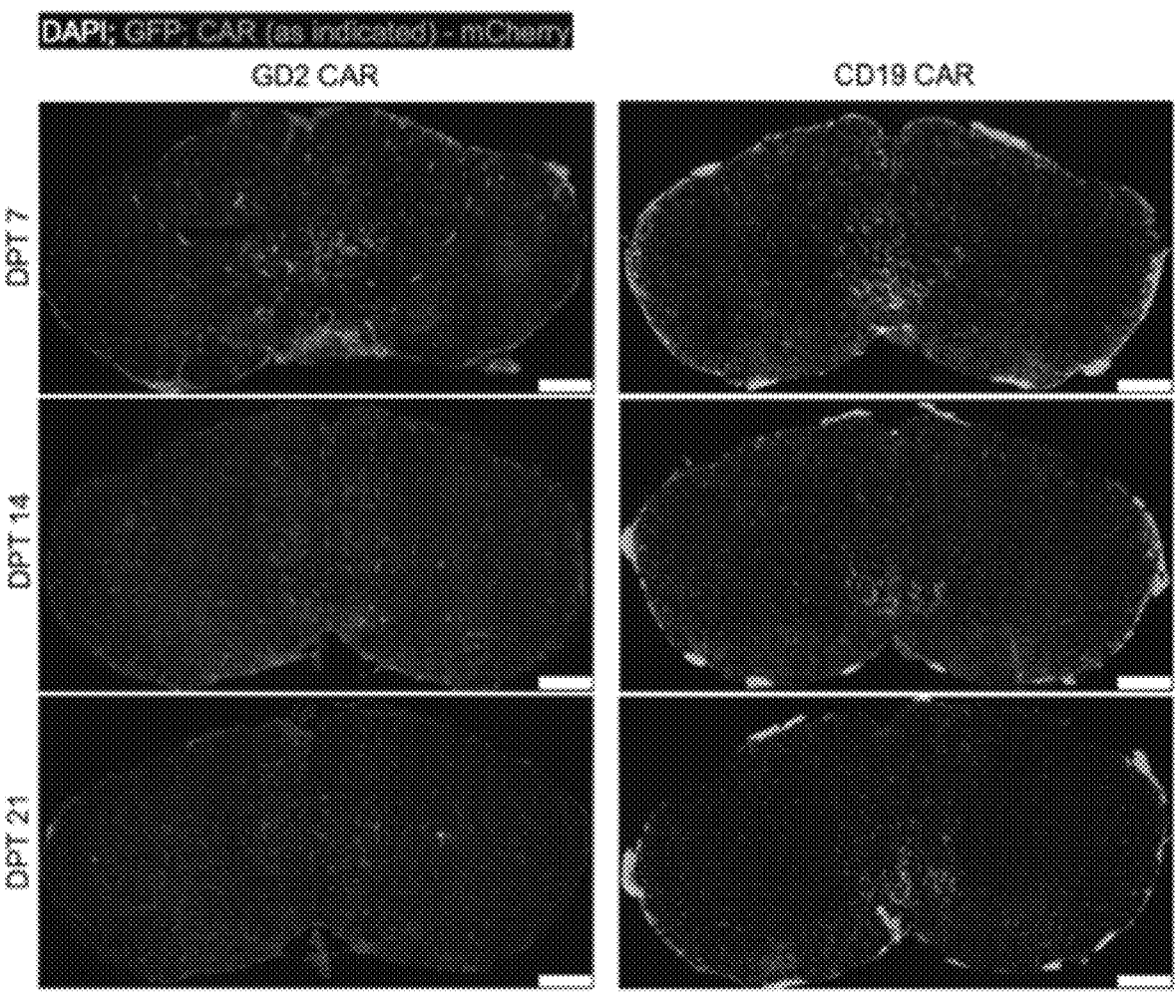
FIG. 9 shows that labeled GD2 CAR T cells invade tumor site during period of antitumor activity. Human T cells bearing a CAR fused at the Cterminus with mCherry were tracked in histological specimens of DIPG xenografts euthanized at the indicated timepoints. DIPG13-FL stably transduced with a lentiviral GFP-luciferase construct were engrafted into the pons of P2 NSG mice and treated with a single intravenous dose of $1\times10^7$ GD2-CAR-mCherry or CD19-CAR-mCherry T cells. Bioluminescence imaging was used to randomize animals with equivalent initial tumor burden into GD2- or CD19-CAR groups. Representative fluorescence micrographs of medullary tumor burden are shown. GD2-CAR-mCherry T cells infiltrate the tumor parenchyma as early as DPT7. By this time point, meningeal tumor has been cleared in the GD2-CARmCherry group but parenchymal tumor burden remains. By contrast, CD19-CARmCherry T cells do not achieve significant tumor clearing, although scattered CD19-CAR-mCherry cells can be identified within the tissue parenchyma. DPT7 and 14 images from GD2-CAR-mCherry animals are presented in FIG. 6H; they are shown again in FIG. 9 for comparison with matched CD19-CAR-mCherry images. Scale bar represents 500 um.

To visualize CAR T-cell infiltration into the parenchyma and tumor, GD2-4-1BBz-mCherry and CD19-4-1BBz-mCherry fusion constructs were generated (see FIG. 6D). By DPT7, GD2-CAR T-cells were extensively distributed throughout the leptomeninges of treated animals, leptomeningeal tumor has been largely eradicated, and few mCherry+ cells were present within the brain parenchyma (see FIG. 6H and FIG. 9). By DPT14, mCherry+GD2-CAR T-cells had widely infiltrated throughout the parenchyma and numerous foci of Iba1+ macrophages (see FIG. 6E) were present in the xenografted site, along with extensive apoptotic cleaved caspase 3+ cells (see FIG. 6F). Notably, very few cleaved caspase 3+ apoptotic cells were neurons as identified by NeuN double immunostaining (10 total apoptotic neurons identified across 4 mice (see FIG. 6G and FIG. 10). By DPT21, mCherry+GD2-CAR T-cells remained present throughout the CNS; whereas few CD19-CAR T-cells infiltrated the parenchyma (see FIG. 9). This indicated that intravenously administered GD2-CAR T-cells enter through the meningeal lymphatic system (see Louveau et al., Nature 523, 337-341 (2015)), then subsequently infiltrate brain parenchyma. Given that resolution of tumor clearance and ventriculomegaly temporally coincide in treated animals, The data also indicate that antigen specific antitumor activity, rather than on-target, off-tumor cell killing, likely precipitates neuroinflammation and edema during active tumoricidal activity that resulted in hydrocephalus.

Example 5

Figure 11A:
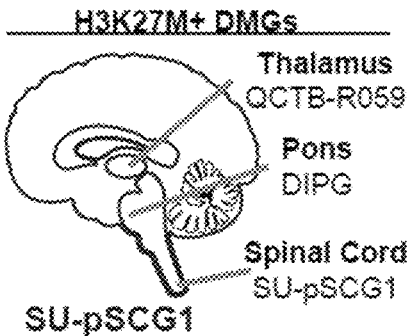
Figure 11B:
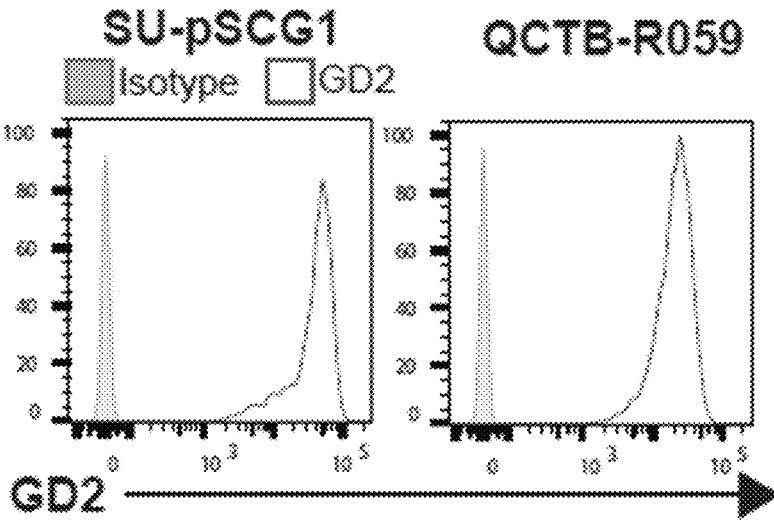
Figure 11C:
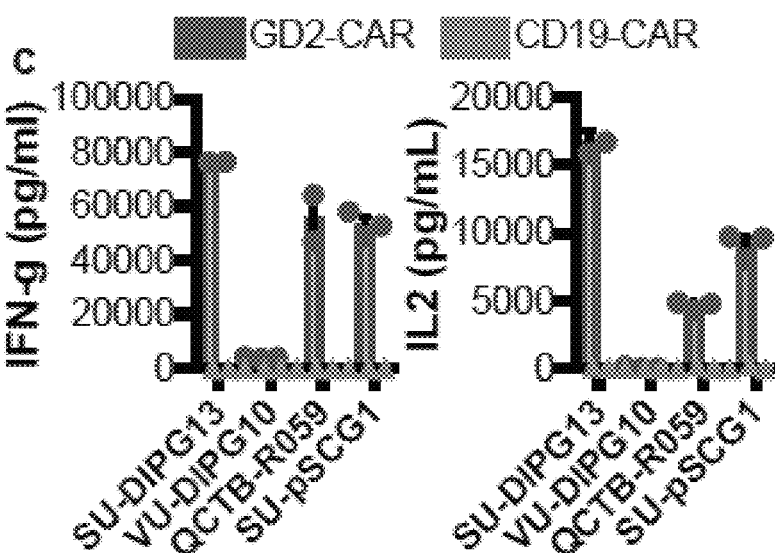
Figure 11D:
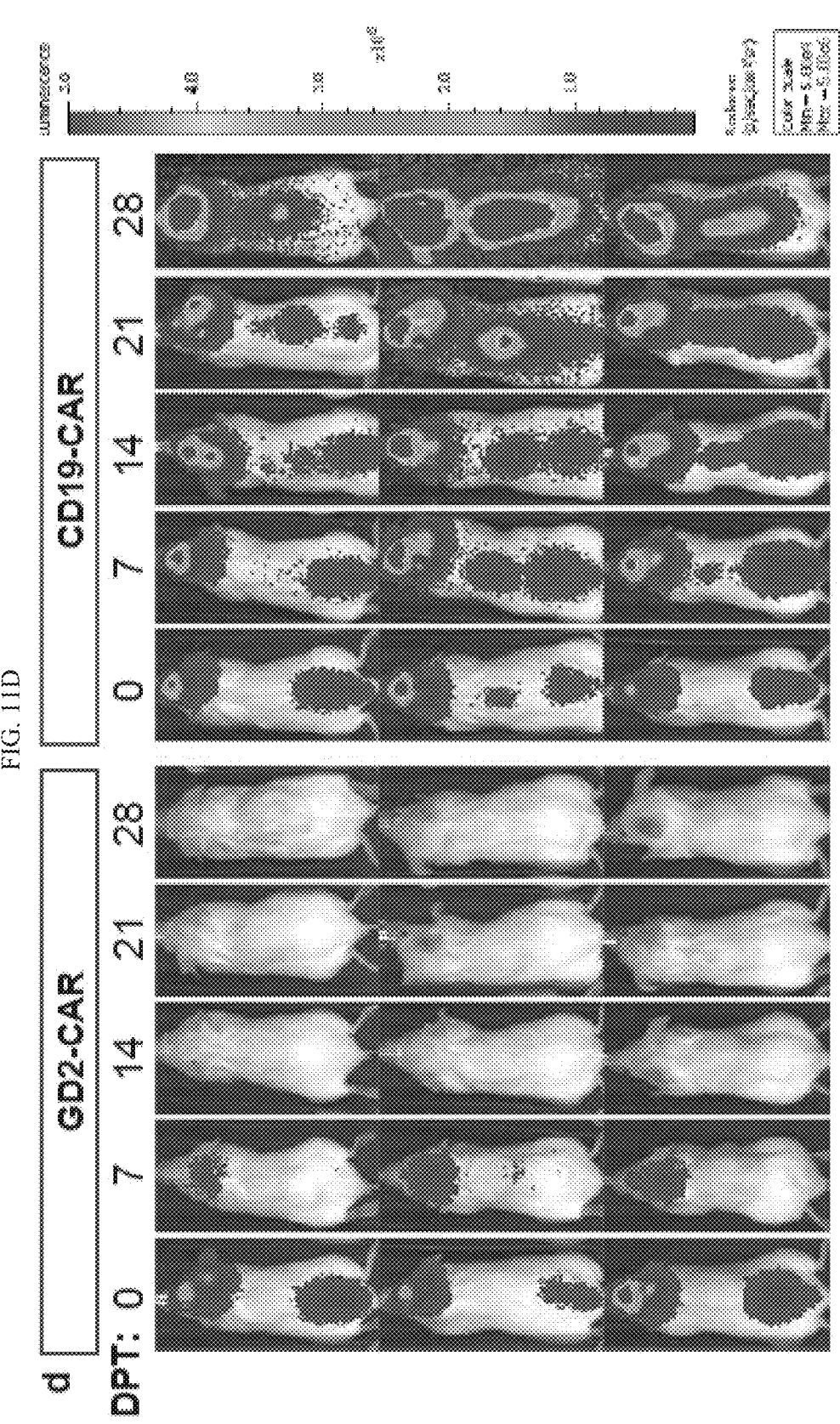

CAR T-Cell Therapy Effectively Clears Multiple Types of Midline H3K27M Mutant Pediatric Diffuse Midline Gliomas but is Associated with Toxicity in Thalamic Xenografts Recent WHO criteria place DIPG within a larger classification of diffuse midline gliomas (DMG) expressing the H3K27M mutation (see FIG. 11A, and Louis et al., Acta Neuropathol 131, 803-820 (2016)). In patient-derived cultures of pediatric H3K27M thalamic (QCTB-R059, derived from resection), and spinal cord (SU-pSCG1, derived postmortem) DMGs, GD2 is also highly and uniformly expressed (see FIG. 11B) and triggers IFNγ and IL-2 production by GD2-CAR T-cells (see FIG. 11C). In order to determine if neuroanatomical site of disease could impact outcomes of CAR T-cell therapy, and to explore in vivo GD2-CAR T-cell efficacy in these H3K27M DMGs, patient-derived orthotopic xenograft models of spinal cord (SUpSCG1) and thalamic (QCTB-R059) glioma were generated. When engrafted in the medulla to avoid the paralysis induced by injection into the spinal cord, widespread SUpSCG1 growth was observed throughout the CNS (see FIG. 11D). Systemic administration of GD2-CAR T-cells achieved potent and lasting tumor-clearing in the spinal cord glioma xenograft model, assessed both by longitudinal bioluminescence imaging (see FIGS. 11D and 11E) and endpoint histology, where approximately 16 residual H3K27M+ cells per animal remained across the sampled volume of 3 GD2-CAR T-cell treated animals (see FIGS. 11F and 11G) No mice from this cohort died during the tumor-clearing phase.

Figure 11H:
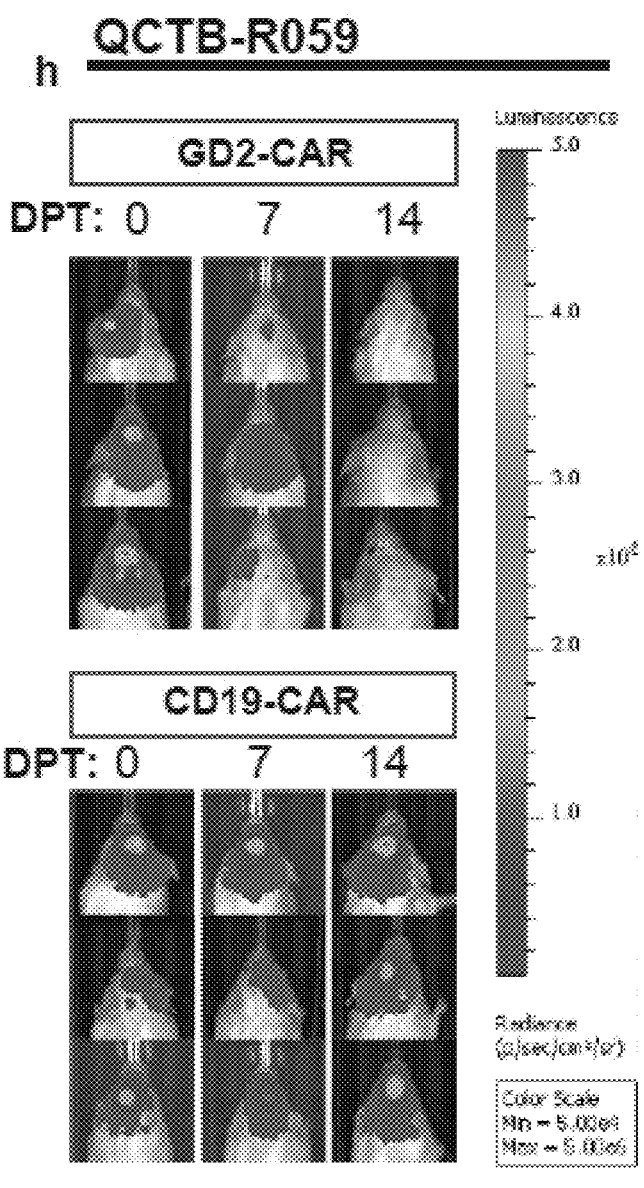
Figure 12:
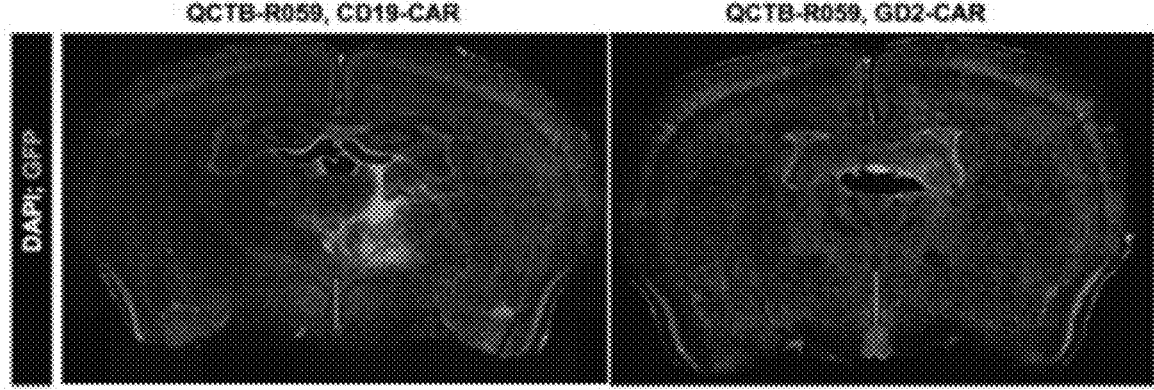
FIG. 12 shows GD2 CAR-T cell therapy achieves histological clearance of tumor burden in surviving QCTB-R059 thalamic H3K27M xenografts. Representative images from CD19 and GD2-CAR T cell treated animals demonstrate clearance of GFP-expressing tumor cells. No region of substantial residual tumor burden could be identified.

To evaluate efficacy in H3K27M thalamic glioma, QCTB-R059 cells were engrafted orthotopically in the thalamus (see FIG. 11H). Tumor clearance was observed in this model (see FIGS. 11H, 11I and FIG. 12) on a similar time scale as observed for DIPG and spinal cord tumors above. However substantial toxicity occurred in GD2-CAR T-cell treated animals during the period of maximal therapeutic effect (see FIG. 11K) The results were reminiscent of "pseudoprogression", well described following immunotherapy with checkpoint inhibitors (see Wolchok et al., Clin Cancer Res 15, 7412-7420 (2009)) and highlight a potential drawback of a robust immunotherapeutic response and subsequent neuroinflammation in neuroanatomical locations intolerant of swelling.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

What is claimed is:

1. A method of killing cancer cells in vitro comprising contacting the cancer cells with an effective amount of immune cells genetically modified to express a chimeric antigen receptor (CAR) specific for ganglioside GD2 (GD2), wherein the cancer cells have a histone H3 K27M (H3K27M) mutation.

2. The method of claim 1, wherein the cancer cells are isolated from a subject.

3. The method of claim 1, wherein the cancer cells are derived from a glioma.

4. The method of claim 3, wherein the glioma is diffuse intrinsic pontine glioma (DIPG) or diffuse midline glioma.

5. The method of claim 1, wherein the immune cells are T cells.

6. The method of claim 1, wherein the immune cells are natural killer (NK) T cells.

7. The method of claim 1, wherein the chimeric antigen receptor (CAR) specific for GD2 comprises an antigen binding domain of an antibody selected from the group consisting of 14G2a, ch14.18, hu14.18K322A, m3F8, hu3F8-IgG1, hu3F8-IgG4, HM3F8, and DMAb-20.

8. The method of claim 7, wherein the antigen binding domain is a single-chain variable fragment (scFv).

9. The method of claim 7, wherein the chimeric antigen receptor (CAR) specific for GD2 further comprises a T cell transmembrane domain, a T cell receptor signaling domain, and/or at least one co-stimulatory domain.

10. The method of claim 9, wherein the co-stimulatory domain comprises part or all of one or more of CD28, OX40/CD134, 4-1BB/CD137/TNFRSF9, FcERIγ, ICOS/CD278, ILRB/CD122, IL-2RG/CD132, and CD40.

11. The method of claim 1, wherein the chimeric antigen receptor (CAR) specific for GD2 comprises an antigen binding domain containing heavy and light chain variable regions (scFv) that bind with specificity to the GD2 epitope: GalNAcβ1-4 (NeuAcα2-8NeuAcα2-3) Gal.

12. The method of claim 1, wherein the CAR comprises the 14G2a scFv.

13. A method comprising:

a) obtaining a biological sample comprising cancer cells from a patient;

b) determining presence of an H3K27M mutation within the cancer cells; and c) contacting the cancer cells with immune cells genetically modified to express a chimeric antigen receptor (CAR) specific for ganglioside GD2 (GD2).

14. The method of claim 13, wherein the cancer is selected from the group consisting of diffuse intrinsic pontine glioma (DIPG) and diffuse midline glioma.

15. The method of claim 13, wherein the contacting kills the cancer cells.

16. The method of claim 13, wherein the contacting induces cytokine generation.

17. The method of claim 13, further comprising determining an effective amount of immune cells genetically modified to express a CAR specific for GD2 to achieve potent cell lysis.

18. The method of claim 1, further comprising determining the effective amount of immune cells genetically modified to express a CAR specific for GD2 to achieve potent cell lysis.

19. The method of claim 1, further comprising determining presence of an H3K27M mutation within the cancer cells.

* * * * *